US012624060B2

(12) United States Patent
Gawin et al.

(10) Patent No.: US 12,624,060 B2
(45) Date of Patent: May 12, 2026

(54) RUTHENIUM COMPLEXES, METHODS OF THEIR PREPARATION AND APPLICATION THEREOF IN OLEFIN CROSS METATHESIS

(71) Applicant: Apeiron Synthesis S.A., Wroclaw (PL)

(72) Inventors: Rafal Gawin, Warsaw (PL); Andrzej Jan Tracz, Wilczyce (PL); Patryk Krajczy, Glogowek (PL)

(73) Assignee: Apeiron Synthesis S.A., Wroclaw (PL)

( * ) Notice: Subject to any disclaimer, the term of this patent is extended or adjusted under 35 U.S.C. 154(b) by 538 days.

(21) Appl. No.: 18/041,880

(22) PCT Filed: Aug. 17, 2021

(86) PCT No.: PCT/EP2021/072809

§ 371 (c)(1),
(2) Date: Feb. 16, 2023

(87) PCT Pub. No.: WO2022/038121

PCT Pub. Date: Feb. 24, 2022

(65) Prior Publication Data

US 2023/0322830 A1 Oct. 12, 2023

(30) Foreign Application Priority Data

Aug. 17, 2020 (PL) ........................................ 434983

(51) Int. Cl.
*C07F 15/00* (2006.01)
*B01J 31/18* (2006.01)
*C07C 6/04* (2006.01)

(52) U.S. Cl.
CPC ....... *C07F 15/0046* (2013.01); *B01J 31/1805* (2013.01); *C07C 6/04* (2013.01); *B01J 2231/543* (2013.01); *B01J 2531/004* (2013.01); *B01J 2531/821* (2013.01); *C07C 2531/22* (2013.01)

(58) Field of Classification Search
CPC ...... C07F 15/0046; C07C 6/04; B01J 31/1805
See application file for complete search history.

(56) References Cited

FOREIGN PATENT DOCUMENTS

WO 2019202509 A1 10/2019
WO WO2020012370 A1 * 1/2020

OTHER PUBLICATIONS

European Patent Office, International Search Report, Application No. PCT/EP2021/072809, Mailed Dec. 2, 2021, 2 pages.

* cited by examiner

*Primary Examiner* — Adam C Milligan
*Assistant Examiner* — Karen Cheng
(74) *Attorney, Agent, or Firm* — ZIEGLER IP LAW GROUP, LLC.

(57) ABSTRACT

Novel ruthenium complexes of general formula 4

4

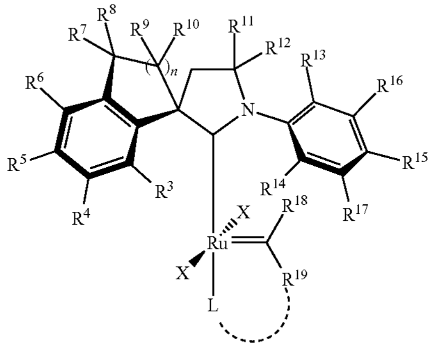

in which the substituents are defined herein. The present disclosure relates also to methods for preparing such compounds and use thereof as catalysts and/or (pre)catalysts in olefin cross metathesis.

13 Claims, No Drawings

RUTHENIUM COMPLEXES, METHODS OF THEIR PREPARATION AND APPLICATION THEREOF IN OLEFIN CROSS METATHESIS

FIELD OF THE INVENTION

The present invention, encompassed in the embodiments, relates to novel ruthenium complexes, methods for preparing such compounds and use thereof as catalysts and/or pre-catalysts in olefin cross metathesis, preferably cross-metathesis of olefins involving ethylene.

STATE OF THE ART

The cross-metathesis involving ethylene as one of the olefins (so-called ethenolysis) is a reaction of great industrial importance. It enables the transformation of olefins containing an internal C═C double bond into compounds with a terminal C═C bond. Among many applications thereof, particular attention should be paid to the possibility of its use in processing of renewable resources such as unsaturated, plant or animal oils and their derivatives. As a result of such processing, compounds with much higher added value are obtained, in particular 1-decene, and esters of 9-decanoic acid (e.g. 9-DAME), which are compounds having high industrial importance, as shown in the reaction below.

Scheme 1. Exemplary ethenolysis reaction of methyl oleate.

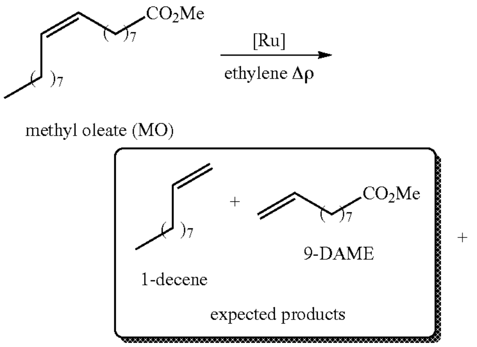

-continued

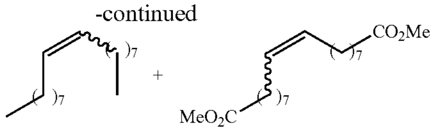

side products

Cross metathesis reactions involving ethylene typically require the use of catalysts, most often carbene ruthenium complexes. From the industrial point of view, the catalyst for this transformation should be characterized by the following features: a) it should enable the reaction to be carried out efficiently (high conversion) with the least amount of catalyst used (desirable by the industry due to the high cost of the catalyst); b) it should enable the reaction to be carried out in a selective manner in order to produce a minimum amount of side products containing internal C═C bond (formed as a result of secondary metathesis reactions of primary products—terminal olefins, or as a result of homo-metathesis of two substrate molecules). In practice, both aspects may be characterized as the highest possible effective turnover number of the catalyst (TON—turnover number).

There are many catalysts for olefin metathesis known in the art (Scheme 2). First generation catalysts (e.g. 1a, 1b) are characterized by good selectivity, but low efficiency in methyl oleate ethenolysis reactions. Second generation catalysts containing NHC carbene ligands with identical aryl substituents on nitrogen atoms (e.g. 2a, 2b) are characterized by both low efficiency and selectivity (Organometallics 2004, 23, 2027-2047; Organometallics 2008, 27, 563-566; Clean 2008, 36, 669-673), the disclosure of which is incorporated by reference herein in its entirety.

Scheme 2. Various catalyst types and TON obtained for ethenolysis reactions.

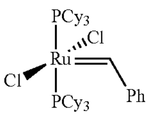

1a, 100 ppm: TON 5 400, sel. 93%

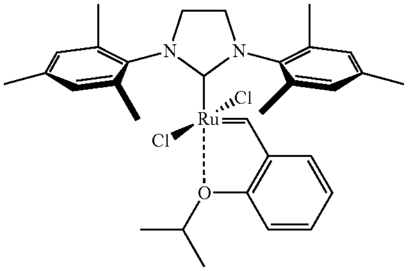

2a, 100 ppm: TON 3 200, sel. 47%

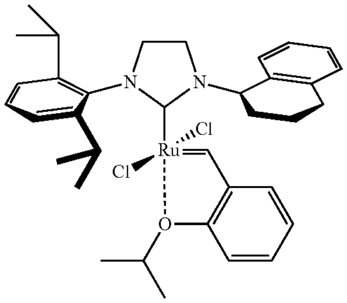

2c, 100 ppm: TON 5 070, sel. 87%

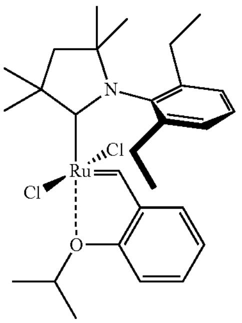

3a, 10 ppm: TON 35 000, sel. 83%

-continued

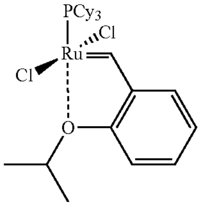

1b, 100 ppm: TON 4 800, sel. 94%

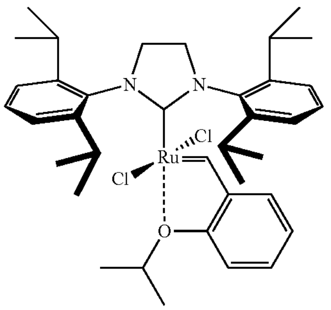

2b, 100 ppm: TON 3 900, sel. 56%

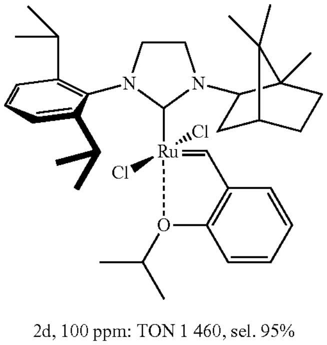

2d, 100 ppm: TON 1 460, sel. 95%

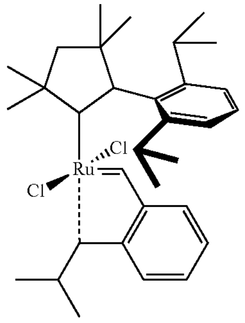

3b, 50 ppm: TON 11 400, sel. 93%

| 1st generation | NHC | NHC | CAAC |
|---|---|---|---|
| low TON values | low TON values | low TON values | higher TON values |
| high selectivity | low selectivity | high selectivity | high selectivity |

Less known second generation catalysts containing NHC ligands with mixed aryl and alkyl substituents on nitrogen atoms (e.g. 2c, 2d) offer selectivity and efficiency similar to first generation catalysts (J. Am. Chem. Soc. 2011, 133, 7490-) 7496), the disclosure of which is incorporated by reference herein in its entirety. Low efficiency of the first- and second-generation catalysts containing NHC ligands results from the instability of the propagating methylidene species.

Second generation catalysts containing CAAC (cyclic alkyl amino carbene, WO 2006/138166, the disclosure of which is incorporated by reference herein in its entirety) ligand e.g. 3a, 3b, allow higher TON values to be achieved than the TON values achieved using catalysts containing an NHC ligand, due to the much greater stability of the propagating methylidene species, which at the same time provides for high selectivity in ethenolysis reactions (Organometallics 2008, 27, 563-566).

There are many second generation ruthenium catalysts containing CAAC ligands substituted in various manners known in the art (Angew. Chem. Int. Ed. 2015, 54, 1919-1923; WO 2015/157736; Angew. Chem. Int. Ed. 2017, 56, 981-986; WO 2017/055945; WO 2019/202509); WO 2010/010290; WO 2017/185324; WO 2011/056881; WO 2020/109217), the disclosures of each of which are incorporated by reference herein in their entirety (Scheme 3, R represents a wide variety of different substituents).

Scheme 3. General formulas of known metathesis ruthenium catalysts comprising CAAC ligands

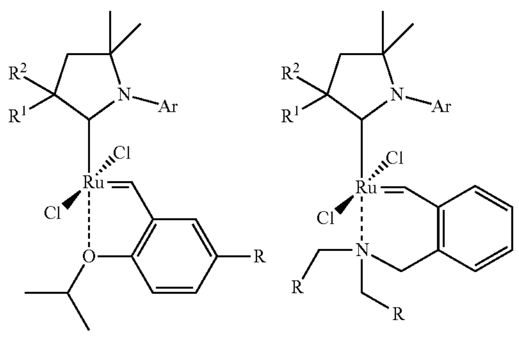

-continued

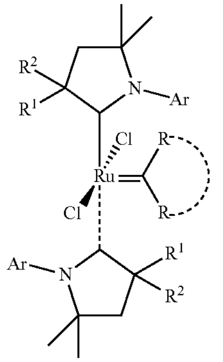

Ruthenium catalysts containing CAAC ligands in which $R^1$ and $R^2$ (according to Scheme 3) are alkyl, alkyl substituents substituted with other groups, aryl or aryl substituted with other groups are known in the art. In particular, embodiments where $R^1$ and $R^2$ form a cycloalkyl or heterocycloalkyl system together with the carbon atom to which they are attached also are known. There are no prior art solutions in which the substituents $R^1$ and $R^2$ together with the atom to which they are attached form a different type of cyclic system. There is also an aryl substituent on the nitrogen atom (Ar, according to Scheme 3).

Research has focused on the structure-activity relationship of several catalysts in an effort to select the most effective catalyst for ethenolysis (Angew. Chem. Int. Ed. 2015, 54, 1919-1923), the disclosure of which is incorporated by reference herein in its entirety. These studies also made it possible to observe several important effects that shape the current state of the art in the field of catalysts containing CAAC ligands and their applications in ethenolysis reactions. In the following considerations, wherever $R^1$ and $R^2$ are used, reference should be made to $R^1$ and $R^2$ according to Scheme 3 above.

A TON value of 60000 was obtained for catalyst 3b, in which $R^1$ and $R^2$ are methyl, whereas when $R^1$ and $R^2$ were combined into a cycloalkyl (cyclohexyl) system in catalyst 3c (the only structural change), a much lower TON value of 43000 was obtained (Scheme 4, a). A TON value of 73000 was obtained for catalyst 3d, in which $R^1$ and $R^2$ are ethyl, whereas when $R^1$ and $R^2$ were combined into a cycloalkyl (cyclohexyl) system in catalyst 3e, a TON value of only 47000 was observed. For catalyst 3a, in which $R^1$ and $R^2$ are methyl substituents the obtained value of TON was 120000, and when these substituents were combined (the only structural change) into a spatially expanded, substituted cycloalkyl (adamantyl) system in catalyst 3f, the ethenolysis reaction did not occur with any significance (less than 5% conversion was obtained).

In case of the catalysts, where one of the methyl substituents $R^1$ or $R^2$ was replaced with a phenyl substituent (Scheme 4, b), slightly higher TON values (see catalysts 3h and 3g as well as 3i and 3a) or the same TON values (see catalysts 3j and 3k) were obtained. The exception is catalyst 3l, where a significant increase in the TON value was obtained (compare with catalyst 3b).

-continued

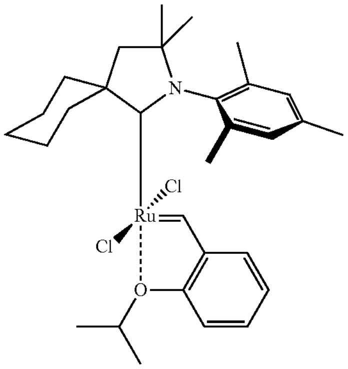

3e, 3 ppm: TON 47 000, sel. 78%

Scheme 4. Influence of $R^1$ and $R^2$ substituents on the TON value in ethenolysis reaction a)

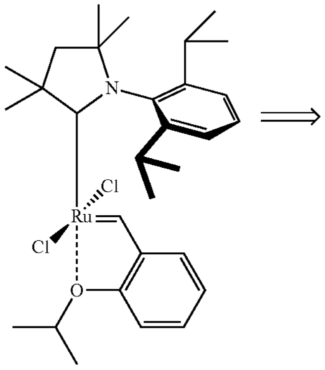

3b, 3 ppm: TON 60 000, sel. 97%

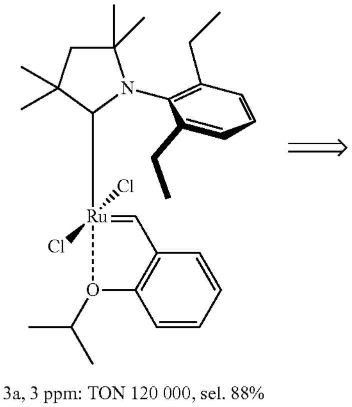

3a, 3 ppm: TON 120 000, sel. 88%

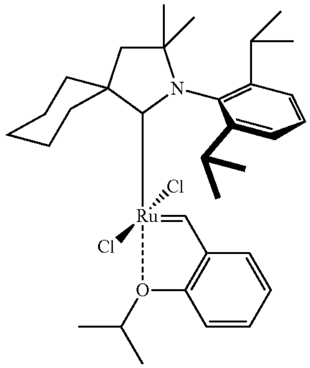

3c, 3 ppm: TON 43 000, sel. 97%

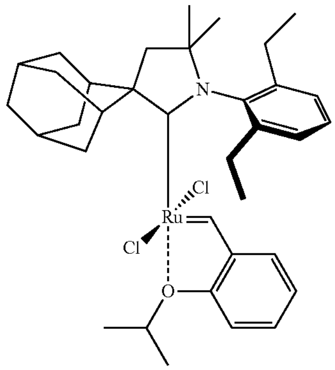

3f, no reaction
catalytically inactive (b)

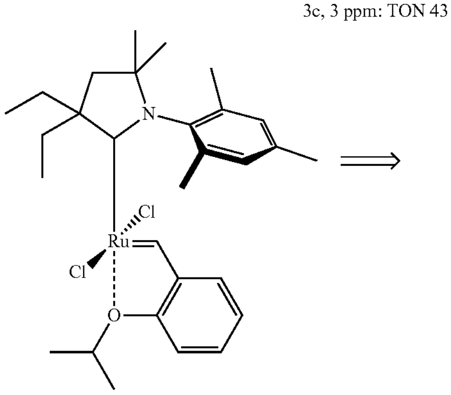

3d, 3 ppm: TON 73 000, sel. 86%

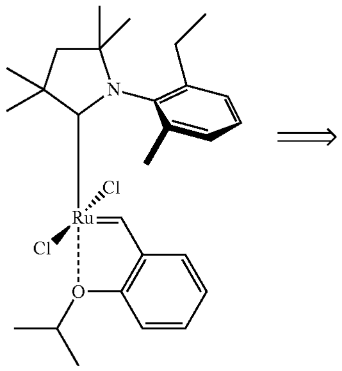

3g, 3 ppm: TON 110 000, sel. 86%

-continued

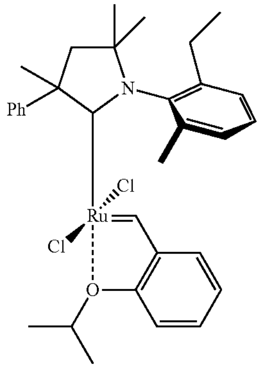

3h, 3 ppm: TON 130 000, sel. 85%

-continued

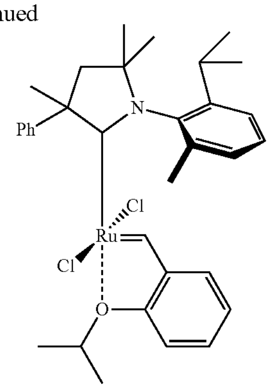

3k, 3 ppm: TON 180 000, sel. 94%

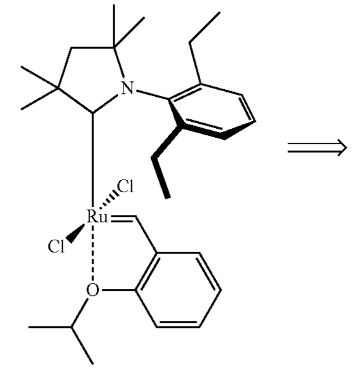

3a, 3 ppm: TON 120 000, sel. 88%

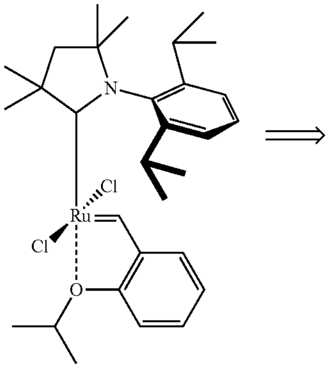

3b, 3 ppm: TON 60 000, sel. 97%

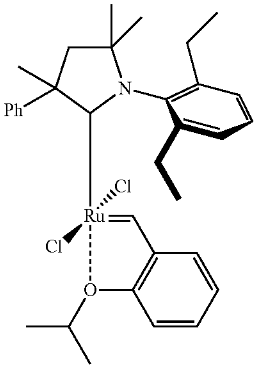

3i, 3 ppm: TON 140 000, sel. 88%

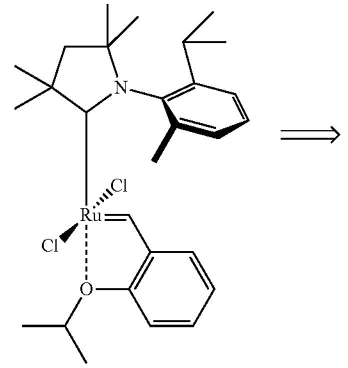

3j, 3 ppm: TON 180 000, sel. 92%

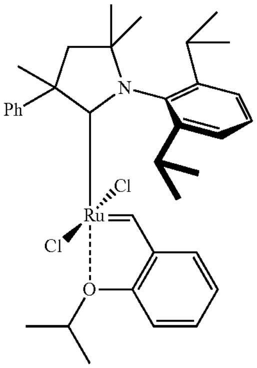

3l, 3 ppm: TON 150 000, sel. 98%

Other modifications of $R^1$ and $R^2$ substituents according to the prior art have not been reported to lead to significant changes in the TON values.

Both for the series of catalysts with methyl substituents in the $R^1$ and $R^2$ positions (Scheme 5, a)) and for the series of catalysts with one methyl and one phenyl substituent in $R^1$ and $R^2$ positions (Scheme 5, b)), an increase in the TON value was observed with increasing size of an aryl substituent on the nitrogen atom until the maximum is reached when the aryl in positions 2 and 6 is substituted with one large (isopropyl) and one small (methyl) substituent (catalysts 3j and 3k). A further increase in the size of the aryl substituent leads to a decrease in the TON value (catalysts 3b and 3l).

Scheme 5. Influence of the aryl substituents on nitrogen aton on the TON values in ethenolysis reaction
a)
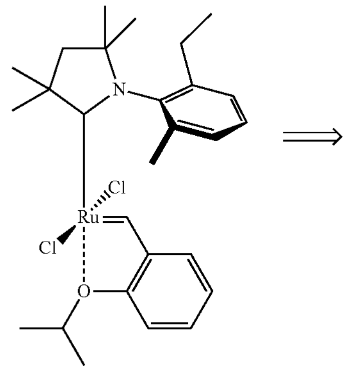
3g, 3 ppm: TON 110 000, sel. 86%
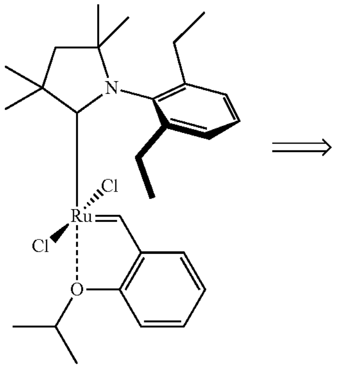
3a, 3 ppm: TON 120 000, sel. 88%
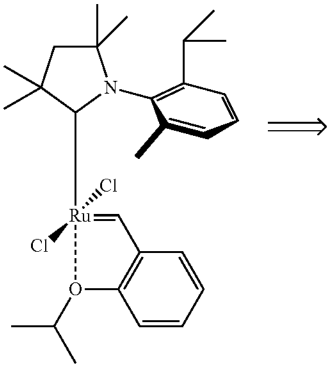
3j, 3 ppm: TON 180 000, sel. 92%
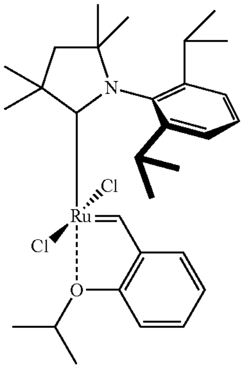
3b, 3 ppm: TON 60 000, sel. 97%
-continued
b)
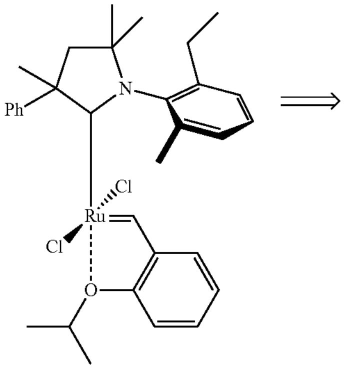
3h, 3 ppm: TON 130 000, sel. 85%
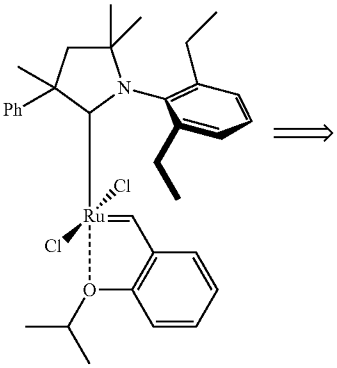
3i, 3 ppm: TON 140 000, sel. 88%
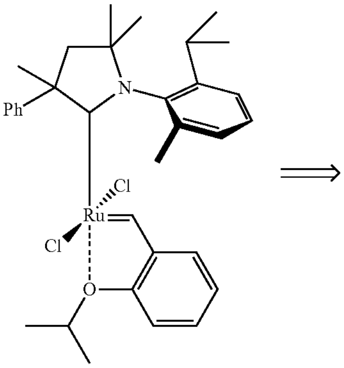
3k, 3 ppm: TON 180 000, sel. 94%
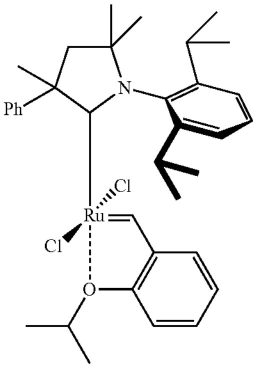
3l, 3 ppm: TON 150 000, sel. 98%
It should be noted that in case of catalysts 3j and 3k which appear to be the most effective catalysts for ethenolysis known and described in the prior art, the nature of $R^1$ and $R^2$ substituents is irrelevant—in both cases identical TON value of 180000 was obtained.

To summarize, according to the state of the art, the substituents $R^1$, $R^2$ are of secondary importance for the high efficiency of the catalysts in the ethenolysis reaction, and their modifications do not lead to a significant increase in TON values. According to the prior art, the size and nature of the aryl substituent on the nitrogen atom appears to be important for the efficiency of the catalyst. In addition, it should be noted that the known prior art TON values for ruthenium metathesis catalysts are closely related to the conditions under which the metathesis reaction was carried out. Due to the very low catalyst load (ppm) required to obtain a high TON value, the most important parameter is the purity of the reactants (this applies not only to ethenolysis, but also to any other olefin metathesis reaction).

It has been shown that the purity of methyl oleate has a great influence on the TON values obtained in the cross-metathesis reaction involving 2-butene (Green Chem. 2006, 8, 450-454, the disclosure of which is incorporated by reference herein in its entirety). Intensive purification of methyl oleate by 3-fold distillation yielded TON value of 470000 with the catalyst (2a), while 1-fold distillation yielded TON value of 174000. The reaction with the substrate untreated by distillation with the same catalyst yielded a TON value of only 1800.

It was shown that use of ethylene of different purities in the ethenolysis reaction also significantly influenced the obtained TON values. For the catalyst 3a, a TON value of 35000 (10 ppm catalyst) was obtained using 99.9% pure ethylene (Organometallics 2008, 27, 563-566, the disclosure of which is incorporated by reference herein in its entirety). The use of ethylene with a purity of 99.95% with the same catalyst provided a TON value of 67000 (Angew. Chem. Int. Ed. 2015, 54, 1919-1923). Ethylene of such high purity made it possible to further reduce the amount of catalyst 3a used to 3 ppm, which yielded a TON value of 120000. With catalyst 3j, a TON value of 180000 (3 ppm of the catalyst) and a TON value of 130000 (1 ppm of the catalyst) were obtained with the use of ethylene having purity of 99.95%, and the use of ethylene with a purity of 99.995% produced a TON value of 340000 (1 ppm of the catalyst).

The type of substrate used is also of importance for the obtained TON value. Methyl oleate is a convenient high purity (>99%) model compound, however, due to the difficulty of obtaining the compound of such purity, it is expensive and not available on a large scale. As a result, it is not typically considered as a suitable raw material desired by the industry. It has been shown in the prior art that use of raw materials much more desired by the industry, such as unsaturated vegetable oils and esters being the products of transesterification of these oils, results in obtaining TON values that are significantly lower than those obtained with pure methyl oleate.

In conclusion, in order to reliably refer to the results described in the prior art, comparisons of catalysts should be carried out under identical experimental conditions, using the same reagents and purification methods. The high TON values described in the prior art were often obtained under conditions that are too demanding for industrial applications, using expensive raw materials not available on a large scale, such as methyl oleate having purity >99%.

It has surprisingly been found that the ruthenium (pre) catalysts containing the CAAC ligand described by the general formula 4 are much more effective than the most effective catalysts for olefin cross-metathesis involving ethylene known in the art. In particular the catalysts described in the embodiments herein, make it possible to obtain very high TON values with use of raw materials desired by the industry and readily available on a multi-tonnage scale, such as unsaturated vegetable oils and esters derived from unsaturated vegetable oils.

Subject of the Invention

One embodiment is a compound of general Formula 4

4

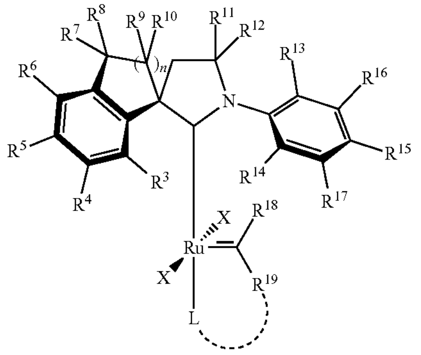

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2$R', —$CH_2$NR'R", —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', wherein R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, wherein R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'"), amide group (—CONR'"R""), formyl group (—CHO), ketone group (—COR'"), and hydroxamic group (—CON(OR'")(R"")), wherein R'" and R"" independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R" or R'" and R"" are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, X denotes halogen atom, and n is 1 or 2, wherein L and $R^{19}$ are optionally linked to each other.

In another embodiment, the compound of general formula 4 has the following substituents:

$R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ are selected from the group comprising hydrogen atom, alkyl group $C_1$-$C_6$, alkoxy group $C_1$-$C_6$, halogen atom, and aryl group $C_6$-$C_{10}$, $R^{18}$ denotes hydrogen atom, $R^{19}$ denotes aryl group $C_6$-$C_{10}$ optionally substituted with at least one alkyl group $C_1$-$C_6$ or —$NO_2$, or $R^{18}$ and $R^{19}$ are optionally linked to each other thereby forming an aromatic polycyclic system, L denotes a neutral ligand selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, aryl group $C_6$-$C_{20}$, heteroaryl group $C_4$-$C_{20}$, alkoxy group $C_1$-$C_6$, or aralkyl group $C_7$-$C_{24}$, or halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, and X denote halogen atom, wherein L and $R^{19}$ are optionally linked to each other.

In another embodiment, in compound of general formula 4:

$R^3$, $R^9$, $R^{10}$, $R^{15}$, $R^{16}$, $R^{17}$ and $R^{18}$ denote hydrogen atom, $R^4$ denotes hydrogen atom, alkyl group $C_1$-$C_6$, or alkoxy group $C_1$-$C_6$, $R^5$ denotes hydrogen atom or alkoxy group $C_1$-$C_6$, $R^6$ denotes hydrogen atom, alkoxy group $C_1$-$C_6$ or halogen atom, $R^7$ and $R^8$ denote hydrogen atom, alkyl group $C_1$-$C_6$, or aryl group $C_6$-$C_{10}$, $R^{11}$ and $R^{12}$ denote alkyl group $C_1$-$C_6$, $R^{13}$ denotes alkyl group $C_1$-$C_6$, $R^{14}$ denotes alkyl group $C_1$-$C_6$, $R^{19}$ denotes aryl group $C_6$-$C_{10}$ optionally substituted with at least one alkyl group $C_1$-$C_6$ or —$NO_2$, or $R^{18}$ and $R^{19}$ are optionally linked to each other, forming an aromatic polycyclic system, L denotes a neutral ligand selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, aryl group $C_6$-$C_{20}$, heteroaryl group $C_4$-$C_{20}$, alkoxy group $C_1$-$C_6$, or aralkyl group $C_7$-$C_{24}$ or halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, X denote halogen atom, and wherein L and $R^{19}$ are optionally linked to each other.

In yet another embodiment, in the compound of general formula 4:

$R^3$, $R^9$, $R^{10}$, $R^{15}$, $R^{16}$, $R^{17}$ and $R^{18}$ denote hydrogen atom, $R^4$ denotes hydrogen atom, methyl group or methoxy group, $R^5$ denotes hydrogen atom or methoxy group, $R^6$ denotes hydrogen atom, methoxy group or chlorine atom, $R^7$ and $R^8$ denote hydrogen atom, methyl group or phenyl group, $R^{11}$ and $R^{12}$ denote methyl group, $R^{13}$ denotes isopropyl group, $R^{14}$ denotes methyl group or isopropyl group, $R^{19}$ denotes benzyl group or phenyl group optionally substituted with isopropyl group or nitro group, or $R^{18}$ and $R^{19}$ together form phenylindenylidene group, L denotes a neutral ligand selected from the group comprising dibenzylamine, benzylmethylamine, isopropyl ether or benzyl ether, iodine atom, triphenylphosphine, dimethylsulfoxide, and pyridine, and X denotes chlorine atom, wherein L and $R^{19}$ are optionally linked to each other.

In another embodiment, the compound of general formula 4 is selected from the group comprising the following compounds:

-continued
4a
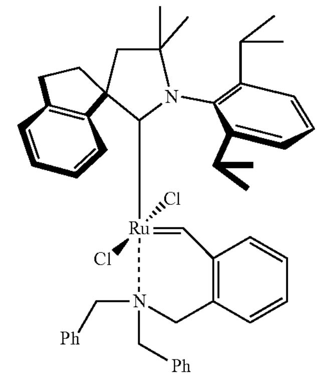
4e
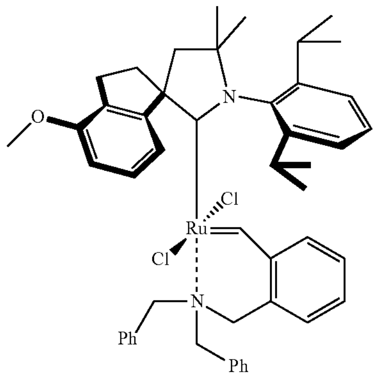
4b
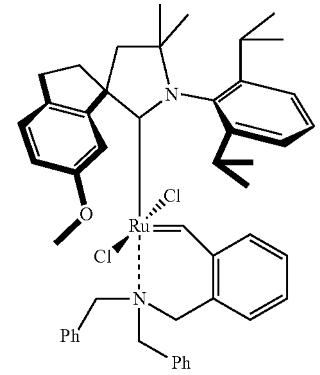
4f
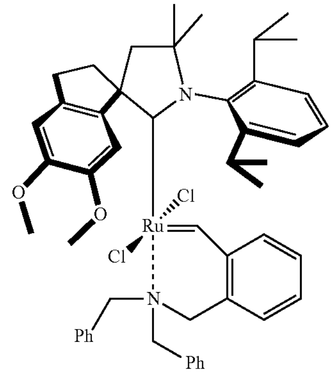
4c
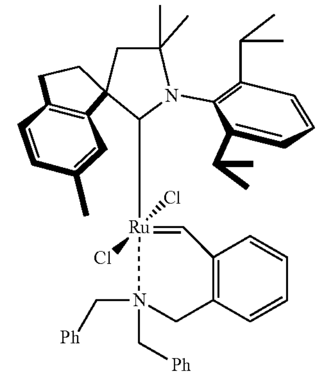
4g
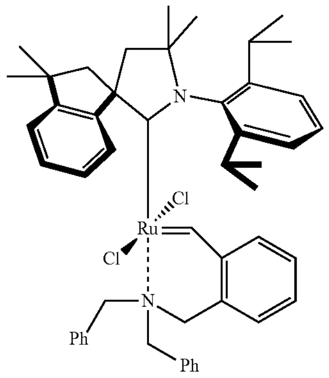
4d
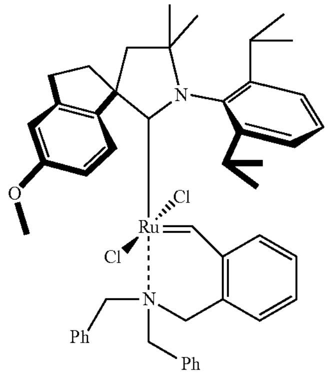
4h
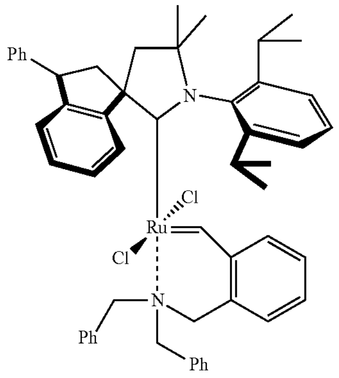

-continued
4i
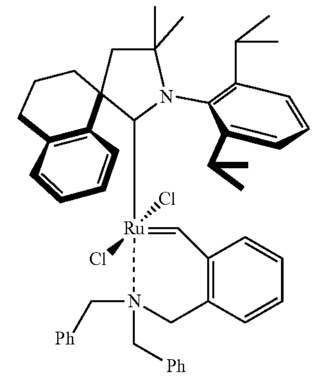
4j
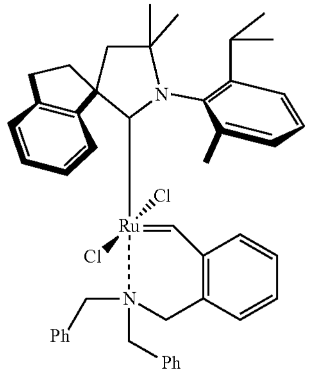
4aa
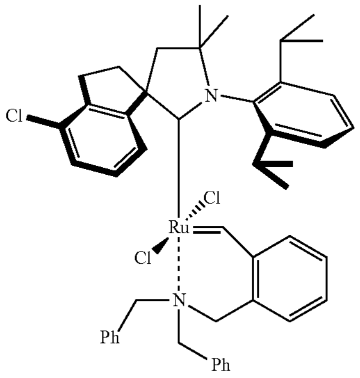
4k
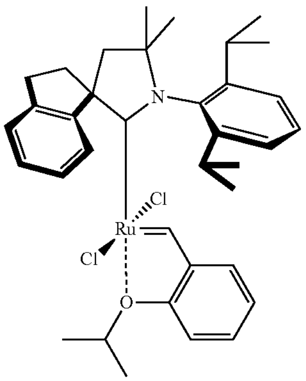
-continued
4l
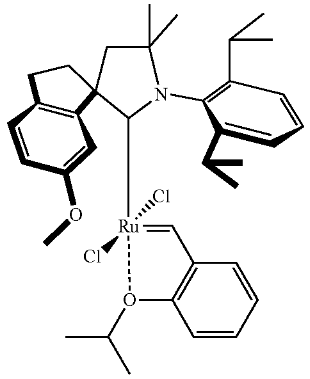
4m
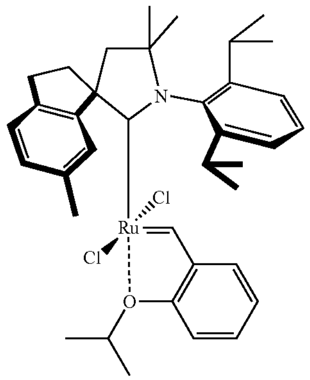
4n
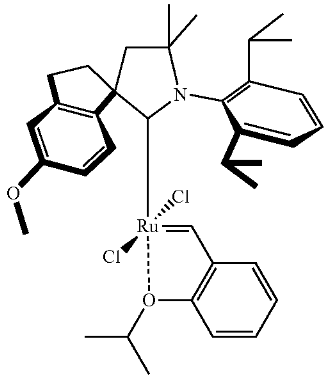
4o
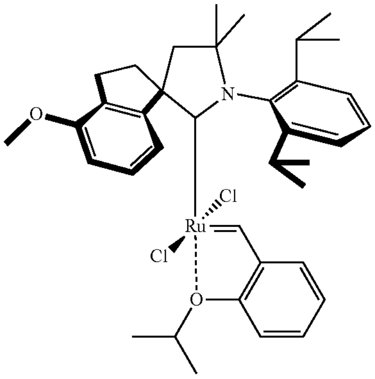

-continued
4p
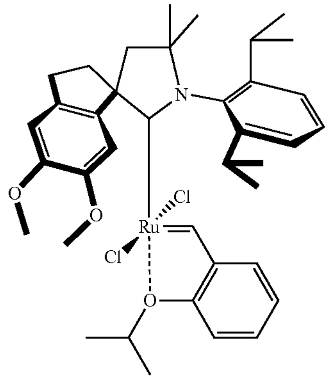
4q
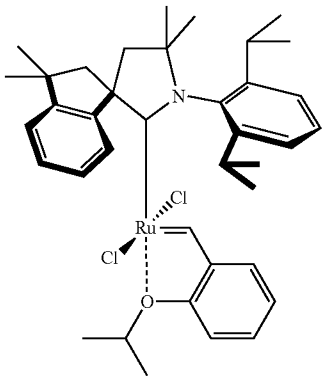
4r
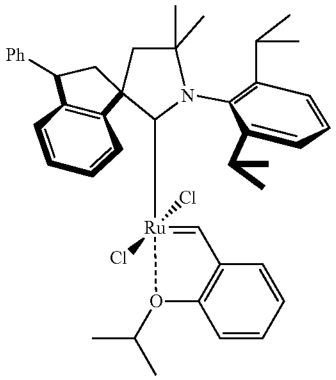
4s
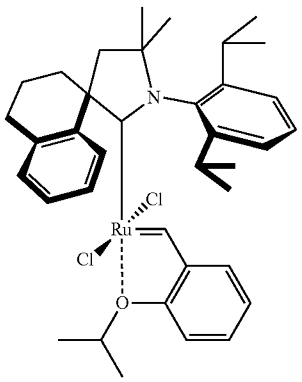
-continued
4t
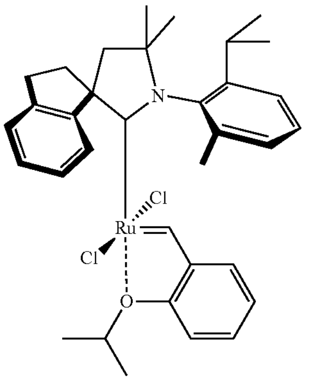
4ab
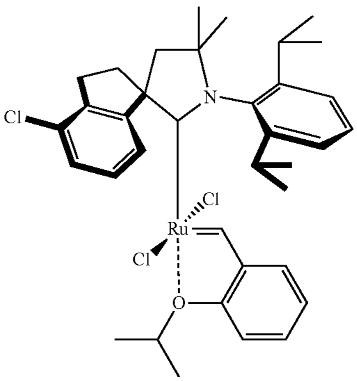
4u
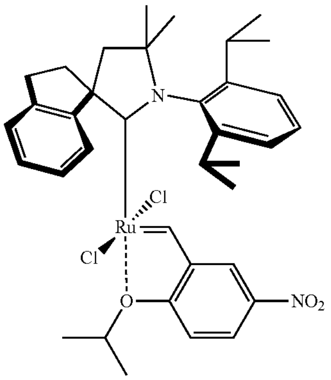
4v
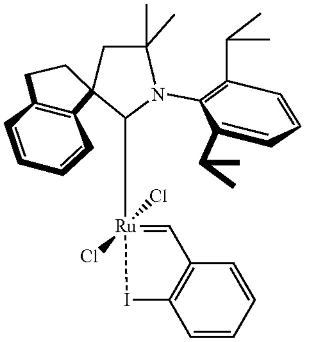

-continued

4w

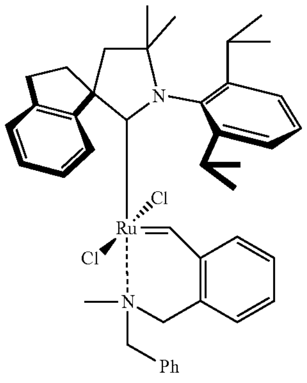

4x

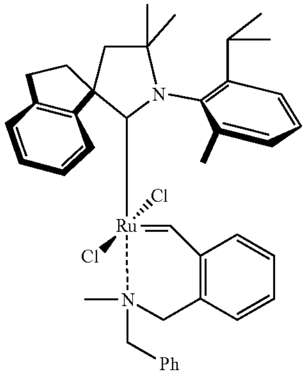

4ac

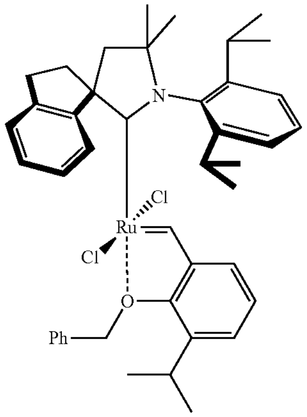

4y

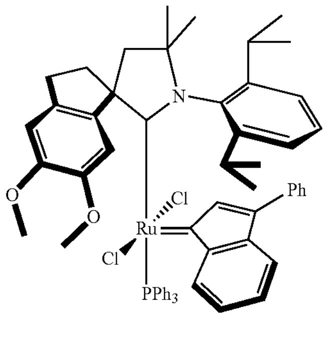

-continued

4z

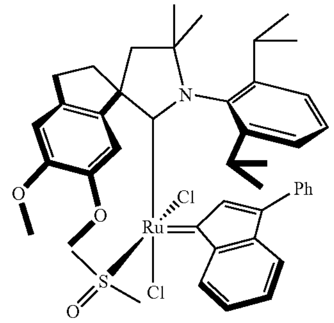

4ad

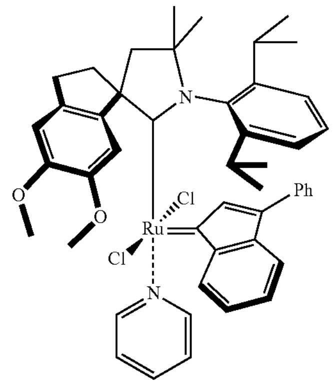

Another embodiment disclosed herein includes a method for preparing the compound of general formula 4,

4

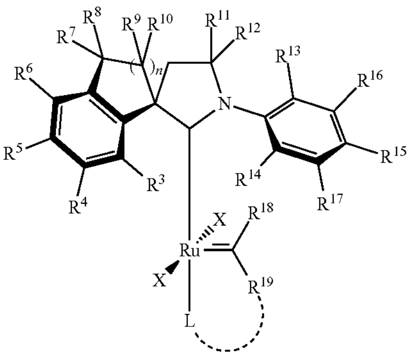

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2$R', —$CH_2$NR'R", —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', in which R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, in which R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'"), amide group (—CONR'"R""), formyl group (—CHO), ketone group (—COR'"), and hydroxamic group (—CON(OR'")(R"")), wherein R'" and R"" independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R" or R'" and R"" are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —$NR'_3$, —$PR'_3$, —$OR'_2$, —$SR'_2$, —S(O)$R'_2$, halogen atom, and optionally substituted pyridine ($C_5H_4NR'$), in which R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'"), amide group (—CONR'"R""), formyl group (—CHO), ketone group (—COR'"), and hydroxamic group (—CON(OR'")(R"")), in which R'" and R"" independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R'" and R"" are optionally linked to each other, X denotes halogen atom, and n is 1 or 2, wherein L and $R^{19}$ are optionally linked to each other, comprising:

(1) reacting a salt of general formula 9

9

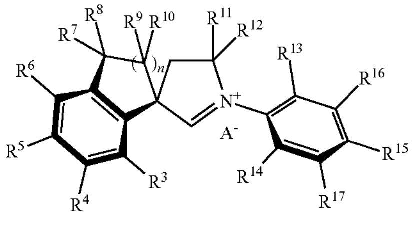

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other are an entity selected from the group comprising hydrogen atom, alkyl group $C_1$-$C_6$, cycloalkyl $C_3$-$C_7$, alkoxy group $C_1$-$C_6$, aryl group $C_6$-$C_{20}$, heteroaryl $C_4$-$C_{20}$, and halogen atom; wherein the entity is optionally substituted with at one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, A-denotes an anion selected from the group comprising halogen anion, $BF_4^-$, $PF_6^-$, $ClO_4^-$, $CF_3SO_2O$—, and $HCl_2^-$ with a base selected from group comprising potassium bis(trimethylsilyl)amide, lithium bis(trimethylsilyl)amide, sodium bis(trimethylsilyl)amide, and lithium diisopropylamide;

(2) subsequently contacting the reaction product of (1) with a complex of general formula 1

1

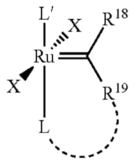

wherein $R^{18}$ denotes hydrogen atom, $R^{19}$ denotes a compound selected from the group comprising aryl group $C_6$-$C_{20}$, heteroaryl group $C_4$-$C_{20}$, aralkyl group $C_7$-$C_{24}$, and alkenyl group $C_2$-$C_6$ wherein $R^{19}$ optionally is substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2$R', —$CH_2$NR'R", —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', wherein R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, wherein R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'"), amide group (—CONR'"R""), formyl group (—CHO), ketone group (—COR'"), and hydroxamic group (—CON(OR'")(R"")), wherein R'" and R"" independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R'" and R"" are optionally linked to each other, or $R^{18}$ and $R^{19}$ are optionally linked to each other, forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$ and heteroaryloxy group $C_4$-$C_{24}$, L denotes a neutral ligand, connected with the ruthenium atom via coordination bond from the heteroatom that forms a part of a compound selected from the group comprising —$NR'_3$, —$PR'_3$, —$OR'_2$, —$SR'_2$, —S(O)$R'_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R''' and R'''' are optionally linked to each other, L' denotes the neutral ligand $P(R')_3$, wherein each substituent R' independently is selected from the group comprising alkyl group $C_1$-$C_{12}$, cycloalkyl group $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, and heteroaryloxy group $C_4$-$C_{24}$, wherein two substituents R' may be linked to each other thereby forming a heterocycloalkyl ring comprising a phosphorous atom as a ring atom, X denotes halogen atom, wherein L and $R^{19}$ are optionally linked to each other;

(3) optionally adding a compound of general formula 10

10

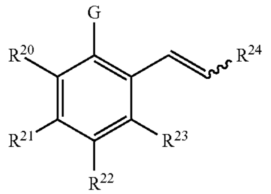

wherein $R^{20}$, $R^{21}$, $R^{22}$, $R^{23}$, $R^{24}$ independently are selected from the group comprising hydrogen atom, alkyl group $C_1$-$C_6$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, halogen atom, —$CH_2R'$, —SR', —S(O)R', —$SO_2R'$, —$SO_2NH_2$, —$SO_2NHR'$, —$SO_2NR'R''$, —NR'R", —$NO_2$, —CN, —COOH, —COOR', —CONR'R", —NR'C(O)R", —NHC(O)R', —NR'C(O)OR", —NHC(O)OR", —CHO, and —COR', wherein R' and R" independently denote alkyl $C_1$-$C_5$, aryl $C_6$-$C_{24}$, wherein R' and R" are optionally linked to each other, $R^{24}$ denotes hydrogen atom or alkyl group $C_1$-$C_6$, G denotes halogen atom or substituent selected from group —OR', —SR', —NR'R", —$CH_2NR'R''$ wherein R' and R" independently denote alkyl group $C_1$-$C_{25}$, cycloalkyl group $C_3$-$C_{12}$, alkoxy group $C_1$-$C_{25}$, aralkyl group $C_7$-$C_{24}$, aryl group $C_6$-$C_{20}$, heteroaryl group $C_4$-$C_{20}$, aryloxy group $C_6$-$C_{24}$, heteroaryloxy group $C_4$-$C_{24}$, which are optionally substituted with at least one alkyl $C_1$-$C_{12}$, alkoxy $C_1$-$C_{12}$, aryloxy $C_6$-$C_{24}$, heteroaryloxy $C_4$-$C_{24}$, halogen atom, ester group (—COOR'''), amide group (—CONR'''R''''), formyl group (—CHO), ketone group (—COR'''), hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R''' and R'''' are optionally linked to each other; and (4) optionally adding a copper (I) chloride or $ArSO_2Cl$, wherein Ar denotes aryl group $C_6$-$C_{20}$.

Another embodiment includes a method for preparing a compound of formula 4"

4"

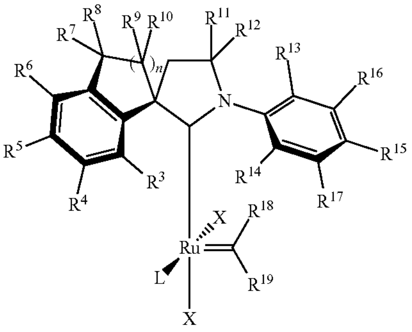

in which

L denotes R'S(O)R", wherein R' and R" independently are selected from the group comprising alkyl group $C_1$-$C_5$, cycloalkyl group $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, and heteroaryloxy group $C_4$-$C_{24}$, wherein R' and R" are optionally linked to each other, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2R'$, —$CH_2NR'R''$, —SR', —S(O)R', —$SO_2R'$, —$SO_2NH_2$, —$SO_2NHR'$, —$SO_2NR'R''$, —NR'R", —$NO_2$, —CN, —COOH, —COOR', —CONR'R", —NR'C(O)R", —NHC(O)R', —NR'C(O)OR", —NHC(O)OR", —CHO, and —COR', in which R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, in which R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'''), amide group (—CONR'''R''''), formyl group (—CHO), ketone group (—COR'''), and hydroxamic group (—CON(OR''')(R'''')), wherein R''' and R'''' independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R'' or R''' and R'''' are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —NR'$_3$, —PR'$_3$, —OR'$_2$, —SR'$_2$, —S(O)R'$_2$, halogen atom, and optionally substituted pyridine ($C_5H_4NR'$), in which R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), in which R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, X denotes halogen atom, and n is 1 or 2, wherein L and $R^{19}$ are optionally linked to each other, the method comprising:

reacting (1) a compound of formula 4'

4'

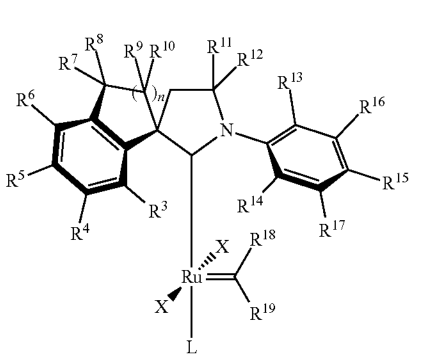

wherein

L denotes P(R')$_3$, wherein each substituent R' independently is selected from the group comprising alkyl group $C_1$-$C_{12}$, cycloalkyl group $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, and heteroaryloxy group $C_4$-$C_{24}$, wherein two substituents R' may be linked to each other, forming a heterocycloalkyl ring comprising a phosphorous atom as a ring atom, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, X, and n are as defined above for formula 4'', with (2)

R'S(O)R'', wherein R' and R'' independently are selected from the group comprising alkyl group $C_1$-$C_5$, cycloalkyl group $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, and heteroaryloxy group $C_4$-$C_{24}$, wherein R' and R'' are optionally linked to each other, wherein the reaction of (1) and (2) is carried out in the presence of $ArSO_2Cl$, wherein Ar denotes aryl group $C_6$-$C_{20}$.

The subject of the invention is also a method for preparing a compound of formula 4'

4'

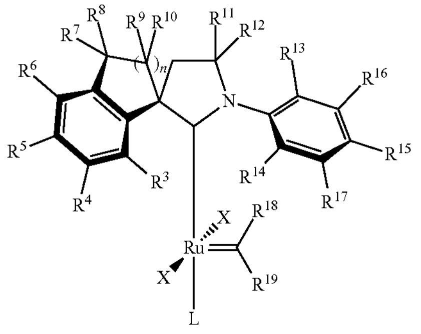

wherein

L denotes optionally substituted pyridine ($C_5H_4NR'$), wherein R' is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and aralkyl group $C_7$-$C_{24}$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2R'$, —$CH_2NR'R''$, —SR', —S(O)R', —$SO_2R'$, —$SO_2NH_2$, —$SO_2NHR'$, —$SO_2NR'R''$, —NR'R'', —$NO_2$, —CN, —COOH, —COOR', —CONR'R'', —NR'C(O)R'', —NHC(O)R', —NR'C(O)OR'', —NHC(O)OR'', —CHO, and —COR', in which R' and R'' independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, in which R' and R'' are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'''), amide group (—CONR'''R''''), formyl group (—CHO), ketone group (—COR'''), and hydroxamic group (—CON(OR''')(R'''')), wherein R''' and R'''' independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R'' or R''' and R'''' are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —$NR'_3$, —$PR'_3$, —$OR'_2$, —$SR'_2$, —S(O)$R'_2$, halogen atom, and optionally substituted pyridine ($C_5H_4NR'$), in which R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), in which R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, X denotes halogen atom, and n is 1 or 2, wherein L and $R^{19}$ are optionally linked to each other reacting (1) a compound of general formula 4'

4'

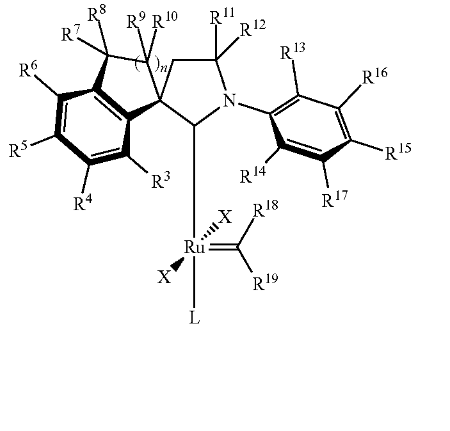

wherein

L denotes $P(R')_3$, wherein each substituent R' independently is selected from the group comprising alkyl group $C_1$-$C_{12}$, cycloalkyl group $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, and heteroaryloxy group $C_4$-$C_{24}$, wherein two substituents R' may be linked to each other thereby forming a heterocycloalkyl ring comprising a phosphorous atom as a ring atom, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, X, and n are as defined above for formula 4', with (2) the compound:

$C_5H_4NR'$, wherein R' is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, alkoxy group $C_1$-$C_6$, aryloxy group $C_6$-$C_{24}$, heteroaryloxy group $C_4$-$C_{24}$, and aralkyl group $C_7$-$C_{24}$, wherein the reaction of (1) and (2) optionally is carried out in the presence of $ArSO_2C_1$, wherein Ar denotes aryl group $C_6$-$C_{20}$.

The subject of the invention is also a method for preparing a compound of formula 4 wherein

4

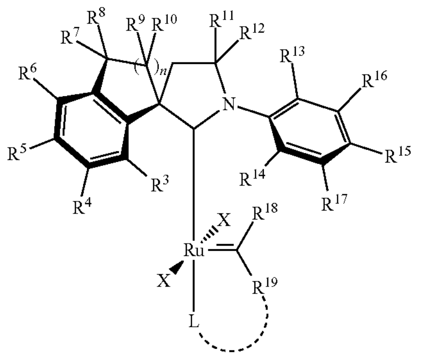

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2$R', —$CH_2$NR'R", —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', in which R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, in which R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'"), amide group (—CONR'"R""), formyl group (—CHO), ketone group (—COR'"), and hydroxamic group (—CON(OR'")(R"")), wherein R'" and R"" independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R" or R'" and R"" are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —NR'$_3$, —PR'$_3$, —OR'$_2$, —SR'$_2$, —S(O)R'$_2$, halogen atom, and optionally substituted pyridine ($C_5H_4$NR'), in which R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'"), amide group (—CONR'"R""), formyl group (—CHO), ketone group (—COR'"), and hydroxamic group (—CON(OR'")(R"")), in which R'" and R"" independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R'" and R"" are optionally linked to each other, X denotes halogen atom, and n is 1 or 2, wherein L and $R^{19}$ are optionally linked to each other, comprising reacting (1) compound of general formula 4", wherein L denotes R'S(O)R", wherein R' and R" independently denote alkyl group $C_1$-$C_5$, cycloalkyl $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, heteroaryloxy group $C_4$-$C_{24}$, wherein R' and R" are optionally linked to each other, and $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, X, n are as defined above for formula 4, with (2) a compound of general formula 10

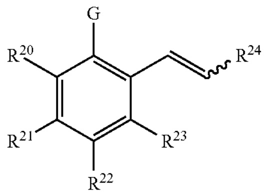

10 wherein $R^{20}$, $R^{21}$, $R^{22}$, $R^{23}$, $R^{24}$ independently are selected from the group comprising hydrogen atom, alkyl group $C_1$-$C_6$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, halogen atom, —$CH_2$R', —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', wherein R' and R" independently denote alkyl $C_1$-$C_5$, aryl $C_6$-$C_{24}$, wherein R' and R" are optionally linked to each other, $R^{24}$ denotes hydrogen atom or alkyl group $C_1$-$C_6$, G denotes a halogen atom or a substituent selected from the group comprising —OR', —SR', —NR'R", and —$CH_2$NR'R" wherein R' and R" independently are selected from the group comprising alkyl group $C_1$-$C_{25}$, cycloalkyl group $C_3$-$C_{12}$, alkoxy group $C_1$-$C_{25}$, aralkyl group $C_7$-$C_{24}$, aryl group $C_6$-$C_{20}$, heteroaryl group $C_4$-$C_{20}$, aryloxy group $C_6$-$C_{24}$, and heteroaryloxy group $C_4$-$C_{24}$, wherein R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, aralkyl $C_7$-$C_{24}$, halogen atom, ester group (—COOR'"), amide group (—CONR'"R""), formyl group (—CHO), ketone group (—COR'"), and hydroxamic group (—CON(OR'")(R"")), wherein R'" and R"" independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R'" and R"" are optionally linked to each other.

Embodiments described herein also include the use of a compound of general formula 4 as a (pre)catalyst and/or catalyst in an olefin cross metathesis.

In one embodiment, the olefin cross metathesis produces at least one compound comprising a terminal double bond C═C as a main product.

In another embodiment, one of the olefins contacted during the cross metathesis reaction is ethylene.

In yet another embodiment, the compound of general formula 4 is used in amount not exceeding 1 ppm, or in an amount of from about 0.1 to about 1 ppm.

In another embodiment, the reaction is carried out without solvent or is carried out in the presence of an organic solvent selected from group comprising toluene, benzene, mesitylene, dichloromethane, dichloroethane, ethyl acetate, methyl acetate, tert-butyl-methyl ether, cyclopentyl-methyl ether, tetrahydrofuran, 2-methyltetrahydrofuran, dimethyl carbonate, cyclohexane, and mixtures thereof.

The reaction also may be carried out at a temperature within the range of from about 20 to about 150° C. and at a pressure from about 1 to about 50 bar.

DETAILED DESCRIPTION OF THE INVENTION

In the first aspect, the invention relates to a compound of general formula 4.

4

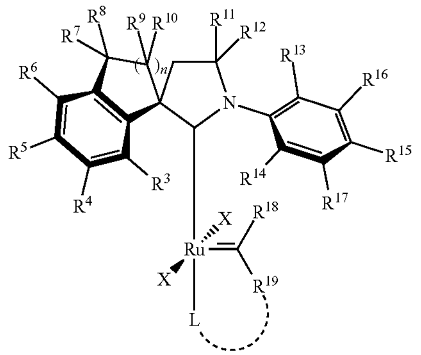

wherein the substituents thereof are defined above.

The specific embodiments of the compounds of general formula 4, are compounds of formulas 4', 4", $4_1$, $4_2$, $4_3$, $4_4$, $4_5$ and $4_6$:

4'

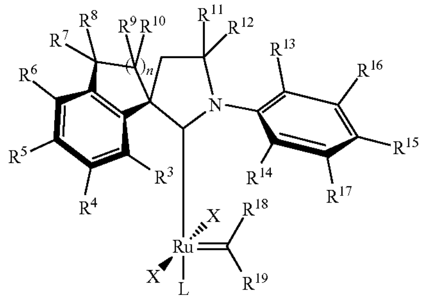

4"

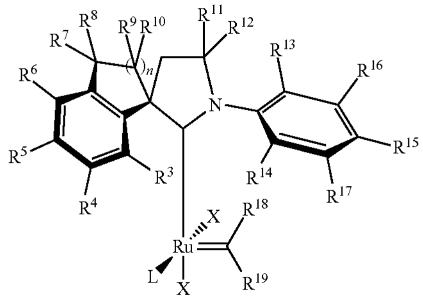

$4_1$

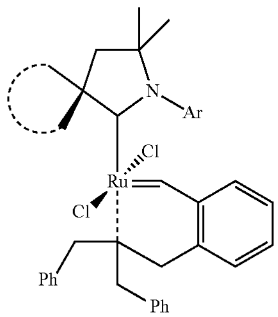

-continued $4_2$

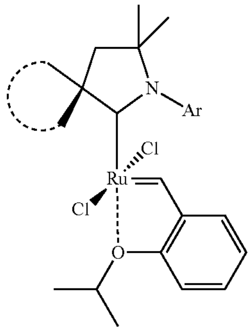

$4_3$

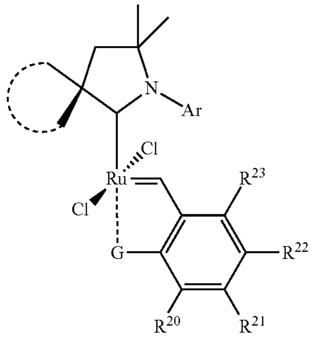

$4_4$

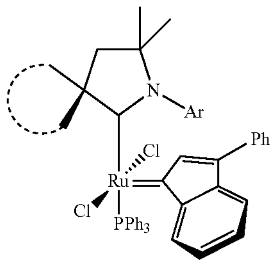

$4_5$

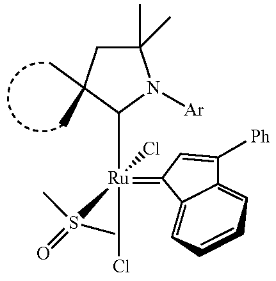

$4_6$

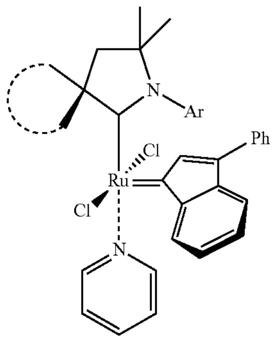

in which the dashed circle denotes a moiety defined as for the general formula 4.

According to the above substituent definitions, the substituent $R^{19}$ and the ligand L may be present in the compound of general formula 4 in linked or non-linked form. In an embodiment in which the substituent $R^{19}$ and the ligand L are linked to each other, they form one moiety bound to the carbon atom connected via a double bond with the ruthenium atom on one side, and with the ruthenium atom via a coordination bond on the other end. For example, in one embodiment, the substituent $R^{19}$ denotes a methylphenyl group, which is linked with the ligand L being dibenzylamine group via a bond between the methyl group and nitrogen atom.

In another embodiment, the substituent $R^{19}$ denotes phenyl group, which is linked with the ligand L being an isopropyl ether moiety with a bond between the phenyl group and the oxygen atom.

An additional embodiment relates to a method for preparing compounds of general formula 4. In the case of the compound of general formula 4, its synthesis includes:

the reaction of a salt of general formula 9:

9

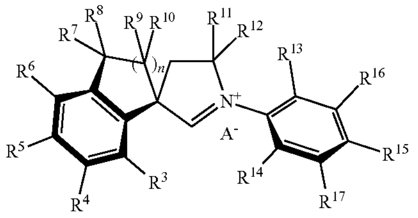

wherein the substituents thereof are defined above;

with an appropriate base selected from the group including potassium bis(trimethylsilyl)amide, lithium bis(trimethylsilyl)amide, sodium bis(trimethylsilyl)amide, lithium diisopropylamide.

As a result of the base action, the salt of general formula 9 is transformed into a cyclic alkylamine carbene (CAAC) of general formula 9':

9'

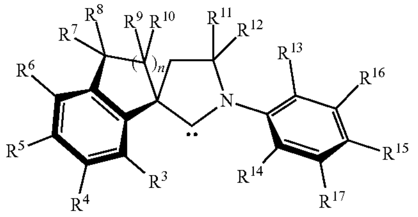

which is subsequently reacted with complex of general formula 1:

1

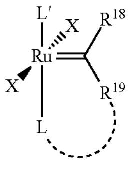

wherein the substituents thereof are defined above.

The reaction of a salt of general formula 9 with the base can be carried out in an aprotic solvent, preferably in solvents selected from aromatic or aliphatic hydrocarbons, and/or ethers, such solvents including toluene, benzene, heptane, cyclohexane, tert-buthyl-methyl ether, diethyl ether, tetrahydrofuran, 2-methyltetrahydrofuran; and most preferably in toluene.

The carbene of general formula 9' that can be prepared by reaction of the salt of general formula 9 with an appropriate base typically is not isolated from the reaction mixture. Rather, the carbene of general formula 9' typically is generated in situ and reacted with the complex of general formula 1 in one reaction vessel.

The process (both the reaction of the salt of general formula 9 with the base, as well as subsequent reaction of the carbene of general formula 9 with the complex of general formula 1) may be carried out at a temperature within the range of from about −100° C. to about +150° C., or from about 0 to about 100° C., or from about 20 to about 80° C.

Optionally, the abovementioned reaction can be carried out in presence of compound of general formula 10

10

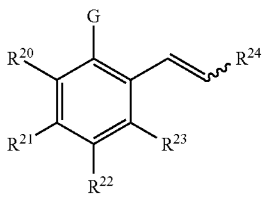

wherein the substituents thereof are defined above, and with optional addition of copper (I) chloride or $ArSO_2Cl$.

The structural moiety present in the compound of general formula 10 may be contained in the general formula 1, thus the addition of compound of general formula 10 is optional.

In general, the copper (1) chloride and $ArSO_2Cl$ are used in order to cleave off the neutral ligand L of the precursor of general formula 1, which causes the compound of general formula 10, after it is linked with ruthenium via a double bond (as a result of a stoichiometric olefin metathesis reaction), to coordinate the heteroatom of the G moiety to ruthenium.

More specific, copper (1) chloride removes the neutral ligands such as phosphines, phosphites, pyridines, from precursor 1 by forming respective complex compounds. In turn, arylsulfonic acid chlorides ($ArSO_2Cl$) e.g. toluenosulphonyl chloride, removes phosphine ligands from precursor 1 through oxidation to phosphine oxides.

In addition, cleaving off the neutral ligand L from precursor 1 may occur as a result of another process, e.g. cleaving off of phosphine or pyridine ligands by the action of acids or alkylating reagents, or as a result of spontaneous dissociation of neutral ligand L at elevated temperature.

The salt of general formula 9 can be obtained by any method known in the art from aldehydes obtained from the corresponding ketones, for example as shown in the following examples, as well as by hydroformylation of alkenes. Alternatively, synthesis of a compound of general formula 4' can be carried out by reacting a compound of general formula 4" with a compound of general formula 10.

In case of compounds of general formula 4", their synthesis typically includes a reaction of compound of general formula 4'

4'

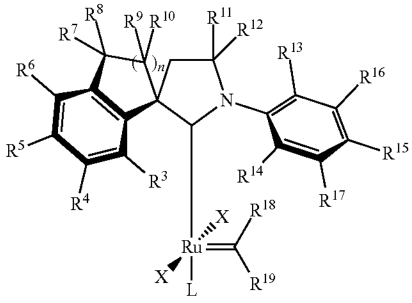

wherein the substituents thereof are defined above, with a compound of formula

R'S(O)R'', wherein the substituents thereof are defined above, in presence of $ArSO_2Cl$.

Alternatively, the synthesis of compounds of formula 4'

4'

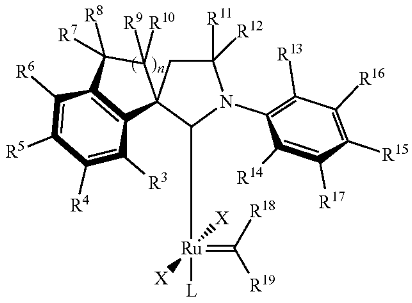

wherein

L denotes optionally substituted pyridine ($C_5H_4NR'$), and remaining substituents are defined above can be carried out by reacting a compound of formula 4'

4'

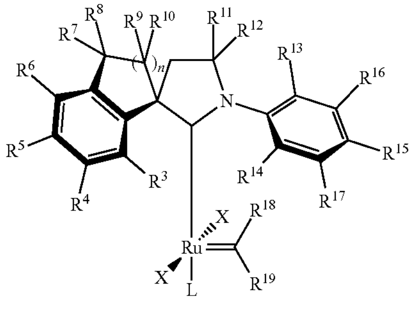

wherein

L denotes $P(R')_3$, and the remaining substituents are defined above with $C_5H_4NR'$, wherein R' is defined above, optionally in presence of $ArSO_2CL$.

Another embodiment relates to the use of compounds of general formula 4 as a (pre)catalyst and/or a catalyst in an olefin cross metathesis, for example in an olefin cross metathesis that results in obtaining at least one compound having a terminal double bond C═C as the main product.

Compounds of general formula 4 can be used as a (pre)catalyst and/or a catalyst in an amount typically not exceeding about 1 ppm, or from about 0.1 ppm to about 1 ppm, or in an amount of about 1 ppm, about 0.5 ppm, about 0.25 ppm, or about 0.1 ppm.

The cross metathesis reaction can be carried out at a temperature within the range of from about 20 to about 150° C., or from about 30-60° C., and at a pressure within the range of from about 1 to about 50 bar, or from about 1 to about 11 bar.

Terms used herein have the following meanings. Any term not defined herein has the meanings which are given and understood by one of ordinary skill in the art in the light of the skilled artisan's knowledge and understanding, the present disclosure, and the context of the specification. Unless otherwise stated, the following chemical term conventions are used in this "specification with the meanings indicated as in the definitions below.

The term "halogen atom" or "halogen" denotes an atom of an element selected from F, Cl, Br, I.

The term "alkyl" or "alkyl group" refers to saturated, linear or branched hydrocarbon substituent having cited number of carbon atoms, for example having 1-25, 1-12, 1-6 or 1-5 carbon atoms. Non-limiting examples of alkyl substituents include: -methyl, -ethyl, -n-propyl, -isopropyl, -n-butyl, -sec-butyl, -isobutyl, -tert-butyl, -n-pentyl, -isopentyl, -neopentyl, -1-methylbutyl, -2-methylbutyl, -3-methylbutyl, -1,1-dimethylpropyl, -1,2-dimethylpropyl, -n-hexyl, -1-methylpentyl, -2-methylpentyl, -3-methylpentyl, -4-methylpentyl, -1-ethylbutyl, -2-ethylbutyl, -3-ethylbutyl, -1,1-dimethylbutyl, -1,2-dimethylobutyl, -1,3-dimethyl-butyl, -2,2-dimethylbutyl, -2,3-dimethylbutyl, -3,3-dim-ethyl-butyl, -n-heptyl, -1-methylhexyl, -2-methylhexyl, -3-methylhexyl, -4-methylhexyl, -5-methylhexyl, -1,2-dim-ethylpentyl, -1,3-dimethylpentyl, -n-octyl, 1,2-dimethyl-hexyl, -1,3-dimethylhexyl, -3,3-dimethylhexyl, -n-nonyl, -1,2-di-methylheptyl, -1,3-dimethylheptyl, -3,3-dimethyl-heptyl, and -n-decyl., -

The term "cycloalkyl" or "cycloalkyl group" refers to a saturated mono- or polycyclic hydrocarbon substituent having indicated number of carbon atoms, for example 3-12 or 3-7 carbon atoms. Non-limiting examples of cycloalkyl substituents are: -cyclopropyl, -cyclobutyl, -cyclopentyl, -cyclohexyl-cycloheptyl, cyclooctyl, -cyclononyl, -cyclodecyl The term "alkoxy" or "alkoxy group" refers to the alkyl substituent as defined above, connected via oxygen atom.

The term "aryl" or "aryl group" refers to an aromatic mono- or polycyclic hydrocarbon substituent having indicated number of carbon atoms, for example 6-24, 7-24, 6-20 or 6-10 carbon atoms, which may be optionally substituted. Non-limiting examples of aryl substituents are phenyl, -tolyl, -xylyl, -naphthyl, -2,4,6-trimethylphenyl, -2-fluorophenyl, -4-fluorophenyl, -2,4,6-trifluorophenyl, -2,6-difluorophenyl, -4-nitrophenyl.

The term "aryloxy" or "aryloxy group" refers to the aryl substituent as defined above connected via oxygen atom. Non-limiting examples of aryloxy substituent are -benzyloxy, -indenoxy, -naphthoxy and the like The term "aralkyl" or "aralkyl group" refers to the alkyl substituent as defined above substituted with at least one aryl as defined above. Non-limiting examples of aralkyl substituents are: -benzyl, -diphenylmethyl, -triphenylmethyl and the like.

The term "alkenyl" or "alkenyl group" refers to a saturated linear or branched non-cyclic hydrocarbon substituent having indicated number of carbon atoms, for example, 2-25 or 2-6 carbon atoms, and containing at least one carbon-carbon double bond. Examples of alkenyl substituents are: -vinyl, -allyl, -1-butenyl, -2-butenyl, -isobutylenyl, -1-pentenyl, -2-pentenyl, -3-methyl-1-butenyl, -2-methyl-2-butenyl, -2,3-dimethyl- 2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl.

The term "cycloalkenyl" or "cycloalkenyl group" refers to a mono- or polycyclic hydrocarbon substituent having indicated number of carbon atoms, for example 3-25 carbon atoms, and containing at least one carbon-carbon double bond.

The term "neutral ligand" refers to an non-charged substituent capable of coordinating with a metallic center (ruthenium atom). Examples of such ligands include: amines, phosphines, phosphites, orthophosphates (III), alkyl and aryl phosphates, arsenates, ethers, alkyl and aryl sulfides, coordinated hydrocarbons, alkyl and aryl halides. Preferably, the neutral ligand is selected from the group including amine (—$NR'_3$), phosphine (—$PR'_3$), ether (—$OR'_2$), thioether (—$SR'_2$) sulfoxide —$S(O)R'_2$) and halogen atom or optionally substituted pyridine ($C_5H_4NR'$). Groups being the neutral ligand can be substituted or unsubstituted.

The term "heteroaryl" or "heteroaryl group" refers to an aromatic mono- or polycyclic hydrocarbon substituent having indicated number of carbon atoms, for example 4-20 carbon atoms, wherein at least one carbon atom has been replaced by a heteroatom selected from O, N and S. Examples of heteroaryl substituents include -furyl, -thienyl, -imidazolyl, -oxazolyl, -thiazolyl, -isoxazolyl, -triazolyl, -oxadiazolyl, -thiadiazolyl, -tetrazolyl, -pyridyl, -pyrimidyl, -triazinyl, -indolyl, -benzo[b]furyl, -benzo[b]thienyl, -indazolyl, -benzoimidazolyl, -azaindolyl, quinolyl, isoquinolyl, carbazolyl.

The term "heteroaryloxy" or "heteroaryloxy group" refers to the heteroaryl substituent as defined above, connected via oxygen atom.

The embodiments described herein are exemplified by the following examples, which will be understood as not limiting the scope of the embodiments.

EXAMPLES

Procedure for Preparing Substrates for Metathesis Reaction

Activated alumina (neutral, 2.5% wt) was added to a respective ester or a mixture of fatty acid esters, and then distilled in vacuo ($10^{-3}$ mbar) at a temperature within the range of from about 160 to about 180° C., with removal of about 10% vol. of heads and 5% vol. of tails.

Activated alumina (neutral, 2.5% wt.) and 2,6-di-tert-butyl-4-methylphenol (0.001 molar eq.) were added to the main distillation fraction. The mixture was stirred under high vacuum conditions ($p<10^{-2}$ mbar) for the purposes of degasification, and then heated to temperature of about 100° C. under argon (gentle flow through the bubbler) and stirred for 1 hour. After cooling down, the mixture was filtered by a thin layer of activated alumina (neutral). Activated alumina (neutral, 2.5% wt) was added to the filtrate and the mixture was stirred under high vacuum conditions ($p<10^{-2}$ mbar) for about 1 hour. The substrate prepared in such a manner, kept over alumina in darkness under argon, was characterized by a peroxide value of <0,1 meq$O_2$/kg.

General Procedure for Carrying Out the Ethenolysis Reaction

Ethylene with a purity of 99.995% was used to carry out the ethenolysis reaction. Appropriate ester or mixture of fatty acid esters (15.0 ml, 44.0 mmol) stored over alumina under argon was filtered through a syringe filter (0.2 μm) and degassed with stirring for 30 minutes under high vacuum conditions (p<10-2 mbar). The appropriate amount of the appropriate catalyst (1 ppm, 0.5 ppm, 0.25 ppm or 0.1 ppm) in dry toluene (0.2 ml) was added under argon, where 1 ppm corresponds to 0.000001 molar equivalent of catalyst per 1.0 molar equivalent of an unsaturated fatty acid ester molecule. The mixture was immediately placed in an autoclave equipped with a magnetic stirring device and the atmosphere was changed to ethylene (purging 3 times). Ethylene was introduced into the reactor at a pressure of 11 bar, and then the reactor was placed in an oil bath (on a magnetic stirrer, 700 rpm), and heated to a temperature of 43° C. (the temperature of the reaction mixture measured by a thermocouple inside the reactor was 40° C.). The reaction was carried out for 6 hours with continuous ethylene feed so that its pressure did not drop below 11 bar. After 6 hours the oil bath was removed, the reactor was cooled to room temperature, and the pressure was normalized to atmospheric pressure by removing excess ethylene from the reactor. A sample (about 0.05 ml) of the reaction mixture was collected and diluted with ethyl acetate to 1.5 ml, and a drop of ethyl vinyl ether was added. The solution thus obtained was analyzed using gas chromatography.

The conversion of the reaction was calculated using residual methyl stearate (in case of high oleic sunflower oil esters) or methyl palmitate (in case of rapeseed oil esters) as internal standards (in case of methyl oleate having purity >99% an addition of approximately 1% vol. of methyl stearate was applied). The selectivity and efficiency were calculated using response factors determined by gas chromatography analysis of weighted amounts of the substance standards.

In the following calculations, the GC area under the peak of the respective substances as read from chromatograms were converted to mole amounts using the determined response factors.

Conversion, selectivity, and yield were determined from the following formulas:

$$\text{Conversion }[\%] = 100\times\left(1-\frac{A_{C18}\times A_{IS}^{0}}{A_{C18}^{0}\times A_{IS}}\right)$$

$$n_x = \frac{A_x}{Rf_x\times M_x}$$

$$\text{Selectivity }[\%] = 100\times\frac{n_{9-DAME}}{\sum a_x n_x}$$

$$Yiield[\%] = \frac{\text{Conversion}\times\text{Selectivity}}{100}$$

$$TON = \frac{\text{Yield}\times n_{C18}^{0}/n_{cat}^{0}}{100}$$

$A_{C18}$, $A_{IS}$: GC area under the peak of the substrate (sum of C18: 1, C18: 2, C18: 3 esters) and internal standard (methyl stearate or palmitate) in the sample after the ethenolysis reaction, $A_{C18}^{0}$, $A_{IS}^{0}$: GC area under the peak of the substrate (sum of C18: 1, C18: 2, C18: 3 esters) and internal standard (methyl stearate or palmitate) in the sample before the ethenolysis reaction, $n_x$: number of moles of product x, $A_x$: GC area of product x, $Rf_x$: product response factor x, $a_x$: number of substrate molecules from which the product x is formed, $n_{C18}^0$, $n_{cat}^0$: initial number of moles of substrate (sum of C18:1, C18:2, C18:3 esters) and number of moles of catalyst, Example 1

Preparation of aldehydes 7—precursors of salts 9, from respective ketones 5.

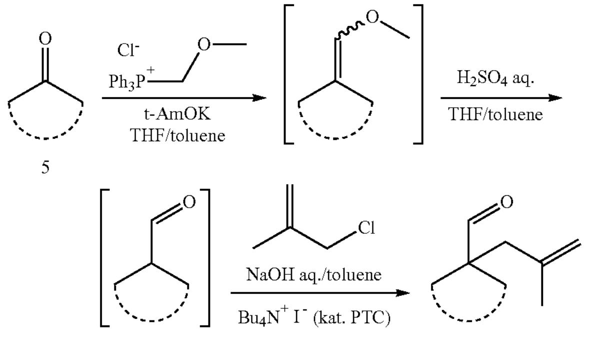

5 6 7

General Procedure:

A solution of potassium tert-amylate in toluene (1.7M, 176 mL, 300 mmol, 1.2 molar eq.) was added dropwise over 15 minutes under argon to a suspension of triphenyl-(methoxymethyl)-phosphonium chloride (103 g, 300 mmol, 1.2 molar eq.) in dry THF (225 mL), maintaining the reaction temperature in the range of 0-5° C. After the dropwise addition, the mixture was stirred for 1 hour at 0-5° C. A solution of the appropriate ketone 5 (250 mmol, 1.0 molar eq.) in dry THF (100 mL) was added dropwise over 30 minutes, keeping the temperature in the range 0-5° C. The mixture was stirred in the cooling bath overnight, allowing the reaction mixture to slowly warm to room temperature. The next day, the reaction mixture was warmed to 55° C. and an aqueous $H_2SO_4$ solution (5M, 60 mL, 300 mmol, 1.2 molar eq.) was added dropwise and stirred overnight at 55° C. The mixture was cooled to room temperature and neutralized with aqueous NaOH solution. The THF was removed in vacuo and the reaction mixture was diluted with toluene and water. The organic phase was separated and the aqueous phase was extracted with toluene (3×200 ml). The combined organic extracts were washed with water and dried over $Na_2SO_4$. After filtering off the drying agent, the solvents were removed in vacuo. $Et_2O$ (500 mL) was added to the residue and stirred vigorously in order to extract the product from the precipitated phosphine oxide.

The mixture was cooled at 0° C. for 2 hours and filtered off. The phosphine oxide was washed with cold $Et_2O$ (4×100 mL). The mixture was evaporated to dryness, and then it was dissolved in cyclohexane (200 mL) and filtered through a silica gel pad. Evaporation gave crude aldehyde 6 which was used in the next step without further purification.

The respective aldehyde 6 (whole amount from the previous step) was dissolved in toluene (50 ml) and then 3-chloro-2-methyl-1-propene (32.1 ml, 325 mmol, 1.3 molar eq.) was added. The obtained solution was added dropwise over 1 hour to a vigorously stirred (>1200 rpm) mixture of 35% aqueous NaOH solution (20 g, 500 mmol, 2.0 molar eq.), toluene (100 ml) and tetrabutylammonium iodide (0.65 g, 1.75 mmol 0.007 molar eq.) heated to 70° C. After the dropwise addition, the mixture was stirred vigorously overnight and then cooled to room temperature. The mixture was diluted with water and toluene and the phases were separated. The aqueous phase was extracted with toluene (3×100 ml). The combined organic phases were washed with water (3×50 ml) and dried over $Na_2SO_4$. After the drying agent was filtered off, the mixture was evaporated to dryness. The crude product was purified by distillation in vacuo to produce product 7 as an oil.

Because the intermediate aldehyde 6 was not isolated, the yields for compounds 7 reported are yields including all synthesis steps starting from ketone 5.

TABLE 1

Compounds of formula 7 obtained in Example 1

| Product: Structure/ Identifier/ Yield | Analytical data |
|---|---|
| 1. 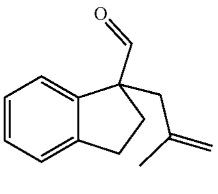 7a/61% | $^1$H NMR (601 MHz, $CDCl_3$) δ 9.61 (d, J = 0.7 Hz, 1H), 7.29-7.22 (m, 4H), 4.85 (p, J = 1.5 Hz, 1H), 4.72-4.70 (m, 1H), 3.02-2.98 (m, 2H), 2.96 (dd, J = 14.4, 1.1 Hz, 1H), 2.63 (ddd, J = 13.3, 7.5, 5.9 Hz, 1H), 2.46 (dd, J = 14.4, 1.0 Hz, 1H), 2.17-2.11 (m, 1H), 1.59 (dd, J = 1.4, 0.9 Hz, 3H). $^{13}$C NMR (151 MHz, $CDCl_3$) δ 200.5, 144.6, 142.1, 141.8, 128.2, 126.7, 125.2, 124.2, 114.7, 63.1, 43.0, 30.9, 30.2, 23.9. HR-MS (ESI) m/z calculated for C14H16ONa [M + Na]$^+$: 223.1093; found: 223.1092. |
| 2. 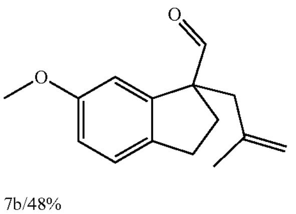 7b/48% | $^1$H NMR (601 MHz, $CDCl_3$) δ 9.58 (d, J = 0.6 Hz, 1H), 7.16-7.12 (m, 1H), 6.79 (dd, J = 8.2, 2.5 Hz, 1H), 6.74 (d, J = 2.4 Hz, 1H), 4.83 (p, J = 1.5 Hz, 1H), 4.70-4.68 (m, 1H), 3.79 (s, 3H), 2.93-2.88 (m, 3H), 2.60 (ddd, J = 13.3, 7.6, 5.8 Hz, 1H), 2.43 (dd, J = 14.3, 1.1Hz, 1H), 2.17-2.10 (m, 1H), 1.57 (dd, J = 1.3, 0.9 Hz, 3H). $^{13}$C NMR (151 MHz, $CDCl_3$) δ 200.6, 159.0, 143.5, 141.8, 136.5, 125.6, 114.8, 114.0, 109.7, 63.2, 55.5, 42.9, 30.9, 30.1, 23.9. HR-MS (ESI) m/z calculated for C15H19O2 [M + H]$^+$: 231.1380; found: 231.1382. |

TABLE 1-continued

Compounds of formula 7 obtained in Example 1

| Product:<br>Structure/<br>Identifier/<br>Yield | Analytical data |
|---|---|
| 3.<br>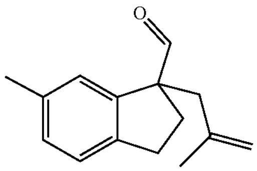 [SMILES: C=C(C)CC1(C=O)CCc2ccc(C)cc21]<br>7c/49% | $^1$H NMR (601 MHz, $CDCl_3$) δ 9.58 (d, J = 0.5 Hz, 1H), 7.14 (d, J = 7.7 Hz, 1H), 7.07-7.04 (m, 1H), 7.03-7.01 (m, 1H), 4.83 (p, J = 1.5 Hz, 1H), 4.70-4.68 (m, 1H), 2.97-2.90 (m, 3H), 2.60 (ddd, J = 13.3, 7.6, 5.7 Hz, 1H), 2.41 (dd, J = 14.4, 1.0 Hz, 1H), 2.36-2.34 (m, 3H), 2.15-2.08 (m, 1H), 1.57 (dd, J = 1.3, 0.9 Hz, 3H).<br>$^{13}$C NMR (151 MHz, $CDCl_3$) δ 200.7, 142.2, 141.9, 141.6, 136.4, 129.0, 124.8, 124.8, 114.6, 63.0, 43.0, 30.5 (2C), 23.9, 21.2.<br>HR-MS (ESI) m/z calculated for C15H19O $[M + H]^+$: 215.1430; found: 215.1424. |
| 4.<br>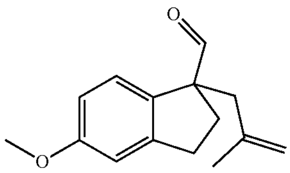 [SMILES: C=C(C)CC1(C=O)CCc2cc(OC)ccc21]<br>7d/19% | $^1$H NMR (601 MHz, $CDCl_3$) δ 9.54 (d, J = 0.6 Hz, 1H), 7.10 (d, J = 8.3 Hz, 1H), 6.81-6.77 (m, 2H), 4.82 (p, J = 1.5 Hz, 1H), 4.69-4.67 (m, 1H), 3.79 (s, 3H), 2.96-2.90 (3H), 2.60 (ddd, J = 13.2, 7.6, 5.7 Hz, 1H), 2.41 (dd, J = 14.3, 1.1 Hz, 1H), 2.14-2.07 (m, 1H), 1.57 (dd, J = 1.3, 0.9 Hz, 3H).<br>$^{13}$C NMR (151 MHz, $CDCl_3$) δ 200.4, 160.1, 146.4, 142.0, 134.0, 124.8, 114.6, 112.8, 110.5, 62.3, 55.4, 43.0, 31.1, 30.6, 23.9.<br>HR-MS (ESI) m/z calculated for C15H18O2Na $[M + Na]^+$: 253.1199; found: 253.1197. |
| 5.<br>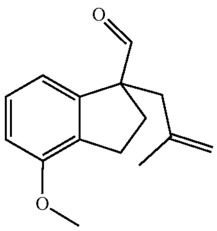 [SMILES: C=C(C)CC1(C=O)CCc2c(OC)cccc21]<br>7e/30% | $^1$H NMR (601 MHz, $CDCl_3$) δ 9.58 (d, J = 0.6 Hz, 1H), 7.23-7.20 (m, 1H), 6.84-6.82 (m, 1H), 6.77-6.75 (m, 1H), 4.82 (dt, J = 3.2, 1.4 Hz, 1H), 4.69-4.67 (m, 1H), 3.83 (s, 3H), 2.97-2.87 (m, 3H), 2.60 (ddd, J = 13.4, 8.4, 5.1 Hz, 1H), 2.44 (dd, J = 14.4, 1.1 Hz, 1H), 2.15-2.09 (m, 1H), 1.56-1.55 (m, 3H).<br>$^{13}$C NMR (151 MHz, $CDCl_3$) δ 200.6, 156.4, 143.9, 141.9, 132.2, 128.4, 116.4, 114.7, 109.6, 63.6, 55.2, 42.9, 30.0, 27.7, 23.9.<br>HR-MS (ESI) m/z calculated for C15H18O2Na $[M + Na]^+$: 253.1199; found: 253.1201. |
| 6.<br>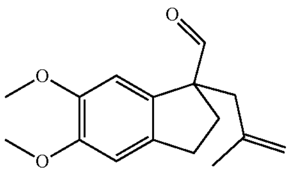 [SMILES: C=C(C)CC1(C=O)CCc2cc(OC)c(OC)cc21]<br>7f/15% | $^1$H NMR (601 MHz, $CDCl_3$) δ 9.55 (s, 1H), 6.77 (s, 1H), 6.68 (s, 1H), 4.82-4.80 (m, 1H), 4.69-4.66 (m, 1H), 3.86 (s, 3H), 3.85 (s, 3H), 2.94 2.90 (m, 2H), 2.88-2.84 (m, 1H), 2.56 (ddd, J = 13.4, 7.9, 5.7 Hz, 1H), 2.41 (dd, J = 14.3, 1.1 Hz, 1H), 2.18-2.11 (m, 1H), 1.54 (s, 3H).<br>$^{13}$C NMR (151 MHz, $CDCl_3$) δ 200.7, 149.5, 148.4, 142.0, 136.6, 133.3, 114.6, 108.0, 107.1, 62.9, 56.2, 55.9, 42.8, 30.9, 30.7, 23.9.<br>HR-MS (ESI) m/z calculated for C16H20O3Na $[M + Na]^+$: 283.1305; found: 283.1305. |
| 7.<br>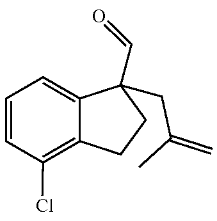 [SMILES: C=C(C)CC1(C=O)CCc2c(Cl)cccc21]<br>7g/80% | $^1$H NMR (601 MHz, $CDCl_3$) δ 9.58 (s, 1H), 7.25-7.23 (m, 1H), 7.20-7.17 (m , 1H), 7.13-7.10 (m, 1H), 4.84 (dt, J = 2.9, 1.3 Hz, 1H), 4.70-4.68 (m, 1H), 2.91-2.86 (m, 1H), 2.70-2.54 (m, 2H), 2.45 (dd, J = 14.4, 1.0 Hz, 1H), 2.15 (ddd, J = 13.4, 9.0, 7.3 Hz, 1H), 1.63 (br, 1H), 1.57-1.56 (m, 3H).<br>$^{13}$C NMR (151 MHz, $CDCl_3$) δ 200.0, 144.1, 142.8, 141.3, 134.6, 128.4, 128.3, 122.5, 115.1, 64.0, 43.1, 30.3, 29.5, 23.9.<br>HR-MS (ESI) m/z calculated for C14H16ClO $[M + H]^+$: 235.0884; found: 235.0884<br>HR-MS (ESI) m/z calculated for C14H15ClNaO $[M + Na]^+$: 257.0704; found: 257.0708 |

TABLE 1-continued

| Compounds of formula 7 obtained in Example 1 | |
|---|---|
| Product: Structure/ Identifier/ Yield | Analytical data |
| 8. 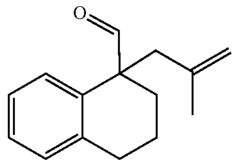 [SMILES: C=C(C)CC1(C=O)CCCc2ccccc21] 7h/76% | $^1H$ NMR (601 MHz, $CDCl_3$) δ 9.61 (s, 1H), 7.28-7.26 (m, 1H), 7.22-7.16 (m, 2H), 7.15-7.12 (m, 1H), 4.83-4.81 (m, 1H), 4.70-4.67 (m, 1H), 2.79-2.76 (m, 2H), 2.75-2.71 (m, 1H), 2.62-2.58 (m, 1H), 2.12-2.07 (m, 1H), 1.92-1.82 (m, 2H), 1.82-1.74 (m, 1H), 1.45 (dd, J = 1.4, 0.9 Hz, 3H). $^{13}C$ NMR (151 MHz, $CDCl_3$) δ 202.1, 141.8, 138.6, 134.6, 129.8, 128.5, 126.9, 126.2, 115.6, 52.5, 44.9, 30.0, 27.8, 24.0, 19.5. HR-MS (ESI) m/z calculated for C15H19O $[M + H]^+$: 215.1430; found: 215.1427. |
| 9. 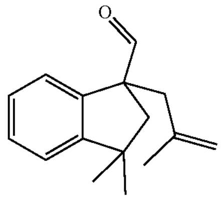 [SMILES: C=C(C)CC1(C=O)CC(C)(C)c2ccccc21] 7l/75% | $^1H$ NMR (601 MHz, $CDCl_3$) δ 9.66 (s, 1H), 7.31-7.28 (m, 1H), 7.25-7.23 (m, 1H), 7.23-7.20 (m, 1H), 7.20-7.17 (m, 1H), 4.86-4.83 (m, 1H), 4.69-4.66 (m, 1H), 3.00-2.96 (m, 1H), 2.56 (d, J = 13.7 Hz, 1H), 2.44 (dd, J = 14.6, 1.1 Hz, 1H), 2.06 (d, J = 13.8 Hz, 1H), 1.58-1.56 (m, 3H), 1.36 (s, 3H), 1.27 (s, 3H). $^{13}C$ NMR (151 MHz, $CDCl_3$) δ 201.4, 152.9, 141.8, 140.9, 128.5, 127.1, 124.3, 123.2, 115.0, 61.7, 44.8, 44.6, 43.3, 31.1, 31.0, 24.0. HR-MS (ESI) m/z calculated for C16H20NaO $[M + Na]^+$: 251.1406; found: 251.1419. |
| 10. 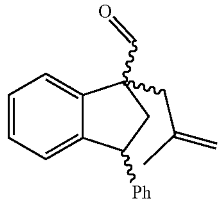 7j/42% | Diastereomer mixture A:B = 1:0.4, Due to the complexity of the NMR spectrum, only shifts of proton and carbon of CHO group are given $^1H$ NMR (601 MHz, $CDCl_3$) δ 9.74 (s, A), 9.62 (d, J = 1.0 Hz, B). $^{13}C$ NMR (151 MHz, $CDCl_3$) δ 201.7 (A), 199.6 (B). HR-MS (ESI) m/z calculated for C20H21O $[M + H]^+$: 277.1587; found: 277.1581. HR-MS (ESI) m/z calculated for C20H20NaO $[M + Na]^+$: 299.1406; found: 299.1405. |

Example 2

Using aldehydes 7 to prepare salts of general formula 9 (formula $9_1$)—precursors of ligand CAAC.
General Synthesis Procedure

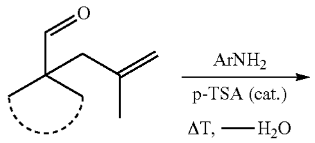

7

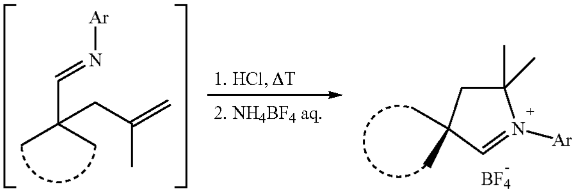

8 $9_1$

The respective aldehyde 7 (35 mmol, 1.4 molar eq.) was dissolved in toluene (75 ml) and the respective aniline $ArNH_2$ (25 mmol, 1.0 molar eq.) and p-toluenesulfonic acid monohydrate p-TSA (0.048 g, 0.250 mmol, 0.01 molar eq.) were added. The mixture was refluxed for 12 hours azeotropically collecting the water evolved in the reaction (flask equipped with a Dean-Stark trap and reflux condenser). The reaction mixture was cooled. The resulting imine 8 was used in the next step without isolation.

A solution of HCl in dry dioxane (4M, 15.6 ml, 62.5 mmol, 2.5 molar eq.) was added under argon to the reaction mixture from the previous step. The mixture was heated overnight at 85° C. The mixture was cooled to room temperature. The solvents were evaporated in vacuo. The residue was dissolved in water (200 ml) and washed with tert-butyl methyl ether (3×25 ml). A solution of $NH_4BF_4$ (5.24 g, 50.0 mmol, 2.0 molar eq.) in water (50 mL) was added dropwise while stirring vigorously. The precipitated crude product was filtered off, washed intensively with water and dried overnight in air. Ethyl acetate (25 ml) was added and mixture was brought to boil. The mixture was cooled to room temperature, filtered and washed with ethyl acetate (3×10 ml). The mixture was dried in vacuo to yield the corresponding salt of formula $9_1$ as a white to beige (9a-9e, 9g-9k) or yellow (9f) crystalline solid.

TABLE 2

Compounds of general formula 9 obtained in Example 2

| Product:<br>Structure/<br>Identifier/<br>Yield | Analytical data |
|---|---|
| 1.<br>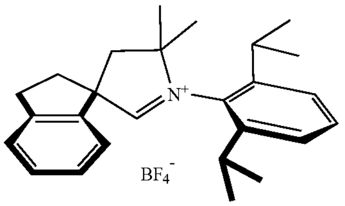<br>9a/90% | $^{1}H$ NMR (601 MHz, $CDCl_3$) δ 8.79 (s, 1H), 7.55 (t, J = 7.8 Hz, 1H), 7.42-7.31 (m, 5H), 7.16 (d, J = 7.2 Hz, 1H), 3.45 (ddd, J = 15.8, 8.6, 6.8 Hz, 1H), 3.26 (ddd, J = 16.3, 8.6, 5.4 Hz, 1H), 3.04 (ddd, J = 13.3, 8.8, 5.4 Hz, 1H), 2.96-2.91 (m, 1H), 2.83 (d, J = 14.1 Hz, 1H), 2.81-2.76 (m, 2H), 2.65 (ddd, J = 13.4, 8.7, 6.5 Hz, 1H), 1.75 (s, 3H), 1.62 (s, 3H), 1.45 (d, J = 6.7 Hz, 3H), 1.40 (d, J = 6.6 Hz, 3H), 1.26 (d, J = 6.7 Hz, 3H), 1.07 (d, J = 6.7 Hz, 3H).<br>$^{13}C$ NMR (151 MHz, $CDCl_3$) δ 186.7, 145.1, 144.7, 144.2, 140.4, 132.1, 129.9, 127.9, 126.2, 126.0, 125.1, 123.1, 83.6, 62.6, 49.3, 38.4, 31.6, 30.3, 29.7, 28.6, 27.3, 26.3, 26.2, 22.9, 21.9.<br>HR-MS (ESI) m/z calculated for C26H34N $[M - BF_4]^+$: 360.2686; found: 360.2684. |
| 2.<br>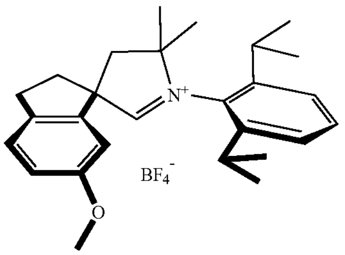<br>9b/69% | $^{1}H$ NMR (601 MHz, DMSO-$d_6$) δ 9.69 (s, 1H), 7.65-7.60 (m, 1H), 7.55-7.50 (m, 2H), 7.34 (d, J = 8.3 Hz, 1H), 7.02 (d, J = 2.3 Hz, 1H), 6.99 (dd, J = 8.3, 2.4 Hz, 1H), 3.81 (s, 3H), 3.20-3.13 (m, 1H), 3.12-3.05 (m, 1H), 2.98-2.84 (m, 3H), 2.79-2.69 (m, 3H), 1.64 (s, 3H), 1.58 (s, 3H), 1.39 (d, J = 6.6 Hz, 3H), 1.35 (d, J = 6.6 Hz, 3H), 1.13 (d, J = 6.7 Hz, 3H), 1.01 (d, J = 6.7 Hz, 3H).<br>$^{13}C$ NMR (151 MHz, DMSO-$d_6$) δ 188.2, 159.3, 144.3, 143.9, 142.6, 136.0, 131.8, 128.9, 126.0, 125.6, 125.1, 115.4, 109.7, 83.7, 62.2, 55.5, 46.7, 37.7, 30.3, 29.4, 28.8, 27.5, 25.8, 25.7, 25.6, 22.1, 21.4.<br>HR-MS (ESI) m/z calculated for C27H36NO $[M - BF_4]^+$: 390.2791; found: 390.2786. |
| 3.<br>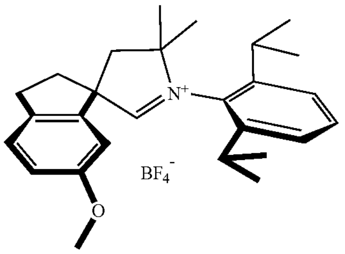<br>9c/71% | $^{1}H$ NMR (601 MHz, $CDCl_3$) δ 8.63 (s, 1H), 7.52 (t, J = 7.8 Hz, 1H), 7.34 (ddd, J = 14.3, 7.8, 1.4 Hz, 2H), 7.21-7.17 (m, 1H), 7.14-7.10 (m, 1H), 6.92 (s, 1H), 3.32-3.23 (m, 1H), 3.18-3.10 (m, 1H), 2.95-2.87 (m, 2H), 2.83-2.70 (m, 3H), 2.59 (ddd, J = 13.2, 8.6, 6.3 Hz, 1H), 2.34 (s, 3H), 1.70 (s, 3H), 1.59 (s, 3H), 1.43 (d, J = 6.7 Hz, 3H), 1.35 (d, J = 6.6 Hz, 3H), 1.18 (d, J = 6.7 Hz, 3H), 1.03 (d, J = 6.7 Hz, 3H).<br>$^{13}C$ NMR (151 MHz, $CDCl_3$) δ 186.4, 144.4, 144.2, 141.7, 140.6, 137.5, 132.0, 130.5, 128.9, 125.8, 125.5, 125.0, 123.8, 83.9, 62.4, 48.9, 38.2, 31.1, 30.1, 29.5, 28.5, 27.0, 26.9, 26.1, 26.0, 22.8, 21.8, 21.2.<br>HR-MS (ESI) m/z calculated for C27H36N $[M - BF_4]^+$: 374.2842; found: 374.2846. |
| 4.<br>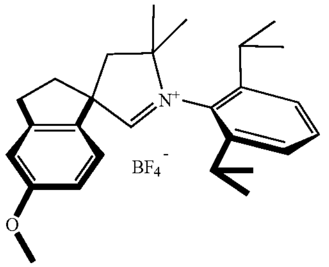<br>9d/54% | $^{1}H$ NMR (601 MHz, $CDCl_3$) δ 8.67 (s, 1H), 7.53 (t, J = 7.8 Hz, 1H), 7.38 (dd, J = 7.9, 1.4 Hz, 1H), 7.34 (dd, J = 7.7, 1.4 Hz, 1H), 7.07 (d, J = 8.3 Hz, 1H), 6.89-6.83 (m, 2H), 3.80 (s, 3H), 3.41-3.34 (m, 1H), 3.22-3.14 (m, 1H), 3.00 (ddd, J = 13.5, 8.7, 4.8 Hz, 1H), 2.90-2.86 (m, 1H), 2.83-2.79 (m, 1H), 2.79-2.72 (m, 2H), 2.63 [ddd, J = 13.4, 8.8, 7.2 Hz, 1H), 1.72 (s, 3H), 1.59 (s, 3H), 1.43 (d, J = 6.7 Hz, 3H), 1.38 (d, J = 6.6 Hz, 3H), 1.23 (d, J = 6.7 Hz, 3H), 1.04 (d, J = 6.8 Hz, 3H).<br>$^{13}C$ NMR (151 MHz, $CDCl_3$) δ 186.3, 161.1, 146.8, 144.5, 144.3, 132.2, 132.0, 128.8, 125.8, 125.0, 124.1, 114.2, 110.9, 83.6, 61.8, 55.5, 49.0, 38.7, 31.6, 30.1, 29.6, 28.4, 27.1, 26.2, 26.1, 22.8, 21.8.<br>HR-MS (ESI) m/z calculated for C27H36NO $[M - BF_4]^+$: 390.2791; found: 390.2795. |

TABLE 2-continued

Compounds of general formula 9 obtained in Example 2

| Product: Structure/ Identifier/ Yield | Analytical data |
|---|---|
| 5.<br>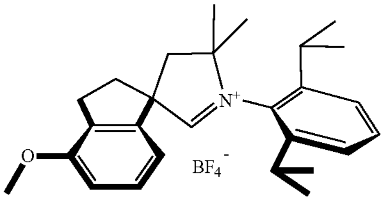<br>9e/81% | $^1$H NMR (601 MHz, DMSO-$d_6$) δ 9.65 (s, 1H), 7.62 (t, J = 7.8 Hz, 1H), 7.52 (ddd, J = 9.2, 7.9, 1.3 Hz, 2H), 7.41 (t, J = 7.9 Hz, 1H), 7.09 (d, J = 7.6 Hz, 1H), 7.05 (d, J = 8.1 Hz, 1H), 3.84 (s, 3H), 3.17-3.10 (m, 1H), 3.10-3.03 (m, 1H), 2.91-2.84 (m, 3H), 2.80-2.74 (m, 1H), 2.74-2.69 (m, 2H), 1.64 (s, 3H), 1.57 (s, 3H), 1.39 (d, J = 6.6 Hz, 3H), 1.35 (d, J = 6.6 Hz, 3H), 1.12 (d, J = 6.7 Hz, 3H), 0.98 (d, J = 6.7 Hz, 3H).<br>$^{13}$C NMR (151 MHz, DMSO-$d_6$) δ 187.7, 156.0, 144.3, 143.9, 142.7, 131.8, 131.7, 129.6, 128.8, 125.5, 125.1, 116.3, 111.2, 83.6, 62.4, 55.4, 47.2, 37.0, 29.4, 28.8, 28.2, 27.4, 26.0, 25.7, 25.6, 22.0, 21.3.<br>HR-MS (ESI) m/z calculated for C27H36NO $[M - BF_4]^+$: 390.2791; found: 390.2792. |
| 6.<br>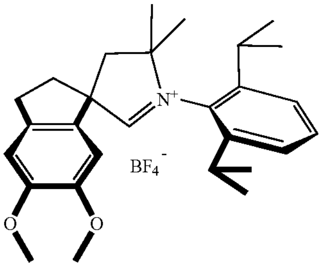<br>9f/60% | $^1$H NMR (601 MHz, $CDCl_3$) δ 8.60 (s, 1H), 7.53 (t, J = 7.8 Hz, 1H), 7.35 (ddd, J = 15.9, 7.9, 1.4 Hz, 2H), 6.85 (s, 1H), 6.73 (s, 1H), 3.88 (s, 3H), 3.86 (s, 3H), 3.31-3.22 (m, 1H), 3.18-3.10 (m, 1H), 2.96-2.90 (m, 2H), 2.86-2.71 (m, 3H), 2.62 (ddd, J = 13.3, 8.7, 6.9 Hz, 1H), 1.70 (s, 3H), 1.62 (s, 3H), 1.42 (d, J = 6.7 Hz, 3H), 1.37 (d, J = 6.6 Hz, 3H), 1.20 (d, J = 6.7 Hz, 3H), 1.04 (d, J = 6.8 Hz, 3H).<br>$^{13}$C NMR (151 MHz, $CDCl_3$) δ 186.6, 150.8, 149.4, 144.4, 144.3, 137.3, 132.1, 131.2, 128.9, 125.8, 125.1, 108.4, 106.5, 83.9, 62.6, 56.4, 56.0, 48.4, 38.8, 31.5, 30.2, 29.6, 28.5, 26.9, 26.3, 26.2, 22.8, 21.9.<br>HR-MS (ESI) m/z calculated for C28H38NO2 $[M - BF_4]^+$: 420.2897; found: 420.2897. |
| 7.<br>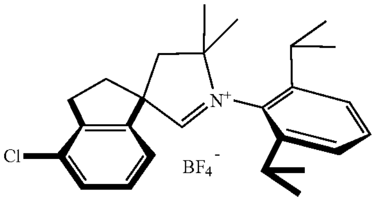<br>9g/68% | $^1$H NMR (601 MHz, $CDCl_3$) δ 9.18 (s, 1H), 7.53 (t, J = 7.8 Hz, 1H), 7.37 (dd, J = 7.9, 1.2 Hz, 1H), 7.34 (dd, J = 7.8, 1.3 Hz, 1H), 7.33-7.30 (m, 1H), 7.28 (t, J = 7.7 Hz, 1H), 7.07 (d, J = 7.2 Hz, 1H), 3.41 (ddd, J = 16.4, 9.0, 5.8 Hz, 1H), 3.23 (ddd, J = 16.9, 8.6, 5.9 Hz, 1H), 3.06-2.98 (m, 1H), 2.95 (d, J = 14.2 Hz, 1H), 2.79-2.69 (m, 3H), 2.63 (ddd, J = 13.4, 8.7, 5.8 Hz, 1H), 1.71 (s, 3H), 1.58 (s, 3H), 1.43 (d, J = 6.7 Hz, 3H), 1.37 (d, J = 6.6 Hz, 3H), 1.23 (d, J = 6.7 Hz, 3H), 1.08 (d, J = 6.8 Hz, 3H).<br>$^{13}$C NMR (151 MHz, $CDCl_3$) 8 187.7, 144.7, 144.2, 143.4, 142.8, 132.2, 132.0, 129.8, 129.4, 129.0, 126.0, 125.0, 121.6, 83.3, 63.4, 49.7, 37.9, 31.4, 30.4, 29.8, 28.6, 27.3, 26.6, 26.3, 23.0, 21.9.<br>HR-MS (ESI) m/z calculated for C26H33CIN $[M - BF_4]^+$: 394.2296; found: 394.2299 |
| 8.<br>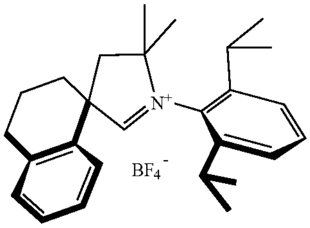<br>9h/89% | $^1$H NMR (601 MHz, $CDCl_3$) δ 8.75 (s, 1H), 7.56 (t, J = 7.8 Hz, 1H), 7.39 (d, J = 7.9 Hz, 2H), 7.28-7.24 (m, 2H), 7.23-7.19 (m, 1H), 6.92-6.88 (m, 1H), 3.05 (d, J = 14.2 Hz, 1H), 3.03-2.98 (m, 1H), 2.97-2.90 (m, 1H), 2.90-2.84 (m, 1H), 2.73 (sept, J = 6.7 Hz, 1H), 2.64 (dd, J = 14.3, 1.3 Hz, 1H), 2.50-2.42 (m, 1H), 2.27-2.16 (m, 2H), 2.00-1.90 (m, 1H), 1.70 (s, 3H), 1.66 (s, 3H), 1.47 (d, J = 6.7 Hz, 3H), 1.37 (d, J = 6.6 Hz, 3H), 1.18 (d, J = 6.8 Hz, 3H), 1.17 (d, J = 6.8 Hz, 3H).<br>$^{13}$C NMR (151 MHz, $CDCl_3$) δ 187.9, 144.8, 144.2, 137.4, 133.6, 132.2, 130.9, 128.9, 128.8, 127.6, 127.3, 125.8, 125.2, 83.9, 56.0, 50.8, 32.7, 30.7, 29.6, 28.6 (2C), 28.4, 26.2, 22.4, 21.8, 18.8.<br>HR-MS (ESI) m/z calculated for C27H36N $[M - BF_4]^+$: 374.2842; found: 374.2842. |
| 9.<br>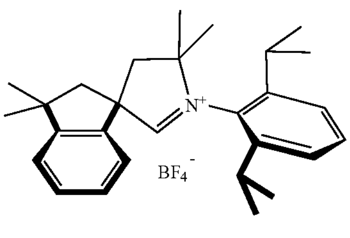<br>9i/65% | $^1$H NMR (601 MHz, $CDCl_3$) δ 8.62 (s, 1H), 7.56 (t, J = 7.8 Hz, 1H), 7.41-7.36 (m, 3H), 7.36-7.32 (m, 1H), 7.29-7.26 (m, 1H), 7.13 (d, J = 7.4 Hz, 1H), 3.02 (d, J = 14.1 Hz, 1H), 2.92-2.86 (m, 1H), 2.84 (d, J = 14.2 Hz, 1H), 2.82 (d, J = 13.5 Hz, 1H), 2.73 (sept, J = 6.7 Hz, 1H), 2.55 (d, J = 13.5 Hz, 1H), 1.71 (s 3H), 1.62 (s, 3H), 1.46 (d, J = 6.7 Hz, 3H), 1.44 (s, 3H), 1.42 (s, 3H), 1.39 (d, J = 6.6 Hz, 3H), 1.19 (d, J = 6.8 Hz, 3H), 1.14 (d, J = 6.8 Hz, 3H).<br>$^{13}$C NMR (151 MHz, $CDCl_3$) δ 186.4, 152.8, 144.4, 144.2, 139.4, 132.2, 130.2, 128.8, 128.5, 125.8, 125.2, 123.7, 123.5, 84.2, 61.0, 52.1, 50.7, 45.4, 31.1, 30.4, 29.6, 29.2, 28.2, 27.2, 26.3, 26.2, 22.6, 21.8.<br>HR-MS (ESI) m/z calculated for C28H38N $[M - BF_4]^+$: 388.2999; found: 388.3001. |

TABLE 2-continued

| Compounds of general formula 9 obtained in Example 2 | |
|---|---|
| Product:<br>Structure/<br>Identifier/<br>Yield | Analytical data |
| 10.<br>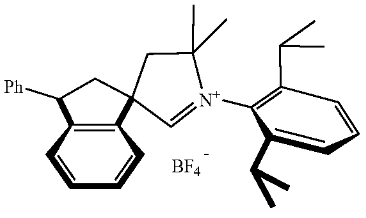<br>9j/20% | Main diastereoisomer:<br>$^{1}H$ NMR (601 MHz, $CDCl_3$) δ 8.72 (s, 1H), 7.55 (t, J = 7.8 Hz, 1H), 7.43-7.33 (m, 4H), 7.33-7.26 (m, 4H), 7.25-7.21 (m, 2H), 7.10 (d, J = 7.3 Hz, 1H), 4.78 (t, J = 7.8 Hz, 1H), 3.18 (d, J = 14.1 Hz, 1H), 3.09 (dd, J = 12.8, 7.2 Hz, 1H), 2.94-2.85 (m, 2H), 2.70 (d, J = 14.2 Hz, 1H), 2.64-2.54 (m, 1H), 1.70 (s, 3H), 1.61 (s, 3H), 1.47 (d, J = 6.7 Hz, 3H), 1.31 (d, J = 6.6 Hz, 3H), 1.19 (d, J = 6.8 Hz, 3H), 0.97 (d, J = 6.7 Hz, 3H).<br>$^{13}C$ NMR (151 MHz, $CDCl_3$) δ 186.3, 146.3, 144.3, 144.2, 142.1, 141.9, 132.2, 130.0, 129.0, 128.8, 128.4, 127.3, 126.4, 125.8, 125.1, 123.2, 84.3, 61.8, 50.1, 48.0 (2C), 30.5, 29.5, 28.1, 27.4, 26.3, 26.2, 22.5, 21.8.<br>HR-MS (ESI) m/z calculated for C32H38N $[M - BF_4]^+$: 436.2999; found: 436.3022. |
| 11.<br>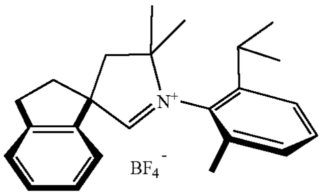<br>9k/74% | Isomers A:B mixture = 1:0.86<br>Isomer A:<br>$^{1}H$ NMR (601 MHz, $CDCl_3$) δ 8.78 (s, 1H), 7.45-7.40 (m, 1H), 7.36-7.27 (m, 4H), 7.24-7.21 (m, 1H), 7.12 (d, J = 7.0 Hz, 1H), 3.39 (dt, J = 15.6, 7.7 Hz, 1H), 3.23-3.07 (m, 1H), 2.87 (d, J = 14.1 Hz, 1H), 2.80 (s, 2H), 2.77-2.71 (m, 1H), 2.52 (dt, J = 13.2, 7.7 Hz, 1H), 2.37 (s, 3H), 1.69 (s, 3H), 1.58 (s, 3H), 1.41 (d, J = 6.6 Hz, 3H), 0.97 (d, J = 6.8 Hz, 3H).<br>Isomer B: $^{1}H$ NMR (601 MHz, $CDCl_3$) δ 8.69 (s, 1H), 7.45-7.40 (m, 1H), 7.36-7.27 (m, 5H), 7.24-7.21 (m, 1H), 3.32 (dt, J = 16.1, 7.9 Hz, 1H), 3.22-3.07 (m, 2H), 2.92-2.87 (m, 1H), 2.80 (s, 1H), 2.77-2.71 (m, 1H), 2.59 (dt, J = 13.4, 7.8 Hz, 1H), 2.32 (s, 3H), 1.68 (s, 3H), 1.63 (s, 3H), 1.37 (d, J = 6.8 Hz, 3H), 1.15 (d, J = 6.7 Hz, 3H).<br>$^{13}C$ NMR (151 MHz, $CDCl_3$) δ 186.9 (A), 186.5 (B), 145.1 (A), 144.7 (B 2C), 144.2 (A), 140.4 (A), 140.2(B), 134.0 (A), 133.4 (B), 131.5, 131.4, 130.7 (A), 130.6 (B), 130.4, 129.8, 129.7, 129.7, 127.9, 127.7, 126.1, 125.9, 125.6, 124.6, 123.8, 123.1 (A), 84.0 (B), 83.5 (A), 62.6 (B), 62.5 (A), 49.4 (A), 48.8 (B), 38.8 (B), 38.3 (A), 31.5 (A), 31.4 (B), 30.0 (A), 29.5 (B), 29.2 (A), 28.1 (B), 27.8 (B), 26.9 (A), 26.1 (B), 26.0 (A), 22.6 (B), 21.7 (A), 19.9 (B), 19.5 (A).<br>HR-MS (ESI) m/z calculated for C24H30N $[M - BF_4]^+$: 332.2373; found: 332.2372. |

Example 3

Preparation of (pre)catalysts of general formula 4 (variants of formula $4_1$), starting from precursor 1c

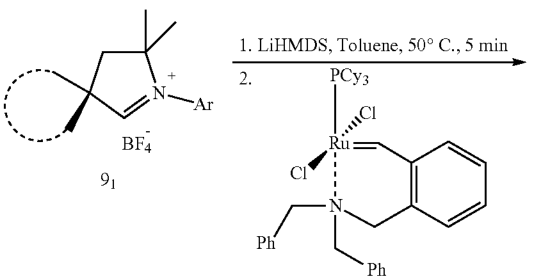

$9_1$ 1c

-continued

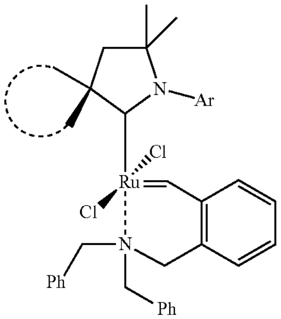

$4_1$

General Synthesis Procedure

Dry, deoxygenated toluene (8 mL) was added under argon to the corresponding salt of formula $9_1$—CAAC precursor (2.0 mmol, 2 molar eq.). The mixture was heated to 50° C. and a solution of LiHMDS in toluene (1 M, 2.0 mL, 2.0 mmol, 2 molar eq.) was added. After 5 minutes, complex 1c (0.752 g, 1.0 mmol, 1 molar eq.) was added in a solid form. The reaction was carried out at 50° C. for 30 minutes. In the case of the synthesis of (pre)catalyst 4j, CuCl (3.5 mmol, 3.5 molar eq.) was added to the reaction mixture and the reaction continued for 10 minutes. The reaction mixture was cooled to room temperature. From this moment, all operations were carried out without a protective argon atmosphere. The reaction mixture was filtered through a Celite pad, which was then washed with toluene. The solvent was evaporated, and the residue was dissolved in $CH_2Cl_2$ and excess n-heptane was added (in the case of (pre)catalysts: 4a, 4b, 4c, 4d, 4g, 4f, 4i, 4aa, 3n) or excess methanol (in the case of (pre)catalysts: 4h, 4e, 4j, 3o, 3m). $CH_2Cl_2$ was slowly removed in vacuo. Initially precipitating impurities were removed by filtration. After removing all impurities, the product began to crystallize. The obtained crystalline product was filtered off and washed with n-heptane (in the case of (pre)catalysts: 4a, 4b, 4c, 4d, 4g, 4f, 4i, 4aa, 3n) or with methanol (in the case of (pre)catalysts: 4h, 4e, 4j, 3o, 3m). It was dried under high vacuum to produce a green crystalline solid as the respective (pre)catalysts of general formula 4 (variants of formula $4_1$).

TABLE 3

Compounds of general formula 4 obtained in Example 3

| Product: Structure/ Identifier/ Yield | Analytical data |
| --- | --- |
| 1. 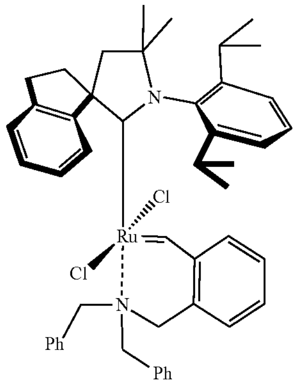 4a/93% | $^1$H NMR (601 MHz, $CD_2Cl_2$) δ 18.34 (s, 1H), 8.80-6.00 (m, 21H), 4.40-2.10 (m, 13H), 1.75-0.90 (m, 16H), 0.65-0.05 (m, 3H). $^{13}$C NMR (151 MHz, $CD_2Cl_2$) δ 314.4, 313.2, 269.3, 267.8, 149.2, 148.9, 148.8, 148.6, 142.5, 142.0, 136.8, 136.1, 135.7, 134.6, 133.5, 133.1, 132.6, 131.4, 129.8, 129.5, 129.1, 128.7, 128.5, 128.2, 127.4, 126.6, 126.2, 125.4, 124.6, 79.0, 72.7, 61.0, 60.6, 58.4, 57.4, 53.5, 40.1, 38.7, 34.3, 31.8, 29.8, 29.6, 28.7, 28.2, 27.4, 26.7, 25.3, 24.9. HR-MS (ESI) m/z calculated for C48H54ClN2Ru [M − Cl]$^+$: 795.3023; found: 795.3027. HR-MS (ESI) m/z calculated for 48H54Cl2N2NaRu [M + Na]$^+$: 853.2607; found: 853.2616. |
| 2. 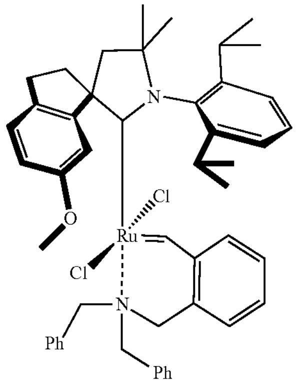 4b/80% | $^1$H NMR (601 MHz, $CD_2Cl_2$) δ 18.36 (s, 1H), 8.70-6.00 (m, 20H), 4.40-2.10 (m, 16H), 1.70-1.00 (m, 16H), 0.60-0.05 (m, 3H). $^{13}$C NMR (151 MHz, $CD_2Cl_2$) δ 314.7, 269.5, 158.3, 149.3, 148.8, 143.4, 140.4, 136.9, 136.0, 135.7, 134.7, 133.0, 132.5, 131.4, 129.8, 129.5, 129.2, 128.7, 128.6, 128.3, 127.4, 126.6, 126.1, 125.0, 117.4, 116.7, 116.1, 79.1, 73.0, 60.8, 58.5, 57.6, 56.4, 52.9, 38.9, 33.2, 32.0, 29.9, 29.6, 28.8, 28.2, 27.3, 26.6, 25.3, 24.8. HR-MS (ESI) m/z calculated for C49H56ClN2ORu [M − Cl]$^+$: 825.3129; found: 825.3137. HR-MS (ESI) m/z calculated for C49H56Cl2N2NaORu [M + Na]$^+$: 883.2713; found: 888.2722. |

TABLE 3-continued

| Compounds of general formula 4 obtained in Example 3 | |
|---|---|
| Product: Structure/ Identifier/ Yield | Analytical data |
| 3. 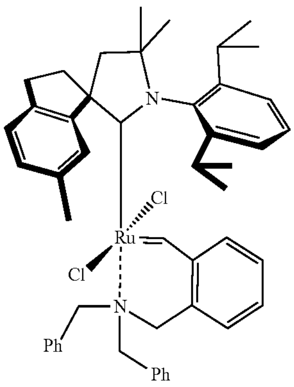 4c/57% | $^1$H NMR (601 MHz, $CD_2Cl_2$) δ 18.35 (s, 1H), 8.75-6.00 (m, 20H), 4.40-2.00 (m, 16H), 1.70-1.00 (m, 16H), 0.60-0.05 (m, 3H). $^{13}$C NMR (151 MHz, $CD_2Cl_2$) δ 314.7, 313.7, 269.7, 268.2, 149.3, 148.8, 145.6, 141.7, 136.9, 136.1, 135.8, 134.8, 134.1, 133.1, 132.5, 131.3, 129.7, 129.4, 129.1, 128.6, 128.3, 127.4, 126.6, 126.1, 124.2, 79.1, 72.6, 60.8, 58.5, 57.4, 53.2, 40.0, 38.8, 34.2, 33.8, 31.9, 31.5, 29.9, 29.6, 29.2, 28.8, 28.2, 27.9, 27.3, 26.6, 25.3, 24.9, 21.7. HR-MS (ESI) m/z calculated for C49H56ClN2Ru [M − Cl]$^+$: 809.3180; found: 809.3184. HR-MS (ESI) m/z calculated for C49H56Cl2N2NaRu [M + Na]$^+$: 867.2764; found: 867.2772. |
| 4. 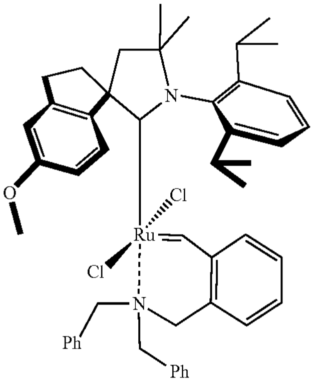 4d/63% | $^1$H NMR (601 MHz, $CD_2Cl_2$) δ 18.40 (s, 1H), 8.80-6.00 (m, 20H), 4.45-2.00 (m, 16H), 1.80-1.00 (m, 16H), 0.60-0.05 (m, 3H). $^{13}$C NMR (151 MHz, $CD_2Cl_2$) δ 315.2, 314.9, 269.8, 268.0, 161.0, 150.7, 149.2, 148.8, 137.0, 136.0, 135.7, 134.6, 133.3, 133.1, 132.5, 131.3, 129.7, 129.0, 128.5, 128.2, 127.4, 127.3, 126.5, 126.1, 112.2, 111.5, 109.4, 108.8, 78.9, 71.7, 60.6, 58.5, 57.3, 55.6, 53.4, 40.2, 39.1, 34.5, 31.7, 31.4, 29.8, 29.6, 28.8, 28.2, 27.8, 27.2, 26.7, 25.5, 25.3, 24.9. HR-MS (ESI) m/z calculated for C49H56ClN2ORu [M − Cl]$^+$: 825.3129; found: 825.3130. HR-MS (ESI) m/z calculated for C49H56Cl2N2NaORu [M + Na]$^+$: 883.2713; found: 883.2714. |
| 5. 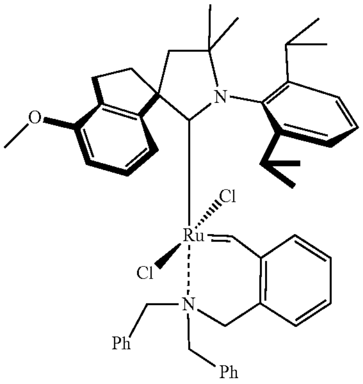 4e/49% | $^1$H NMR (601 MHz, $CD_2Cl_2$) δ 18.34 (s, 1H), 8.50-6.00 (m, 20H), 4.40-2.00 (m, 16H), 1.70-0.90 (m, 16H), 0.60-0.05 (m, 3H). $^{13}$C NMR (151 MHz, $CD_2Cl_2$) δ 314.3, 313.3, 269.2, 267.5, 156.3, 149.4, 148.8, 144.0, 136.8, 136.4, 136.1, 135.7, 134.6, 133.1, 132.6, 131.4, 129.7, 129.1, 128.4, 128.3, 128.2, 127.5, 127.4, 127.0, 126.6, 126.1, 125.5, 110.0, 79.0, 73.3, 61.1, 60.4, 58.3, 57.4, 55.7, 53.1, 51.0, 40.0, 38.8, 31.8, 31.2, 29.8, 29.1, 28.8, 28.2, 27.4, 26.7, 25.3, 24.9. HR-MS (ESI) m/z calculated for C49H57N2ORu [M − 2Cl + H]$^+$: 791.3522; found: 791.3531. HR-MS (ESI) m/z calculated for C49H56Cl2N2NaORu [M + Na]$^+$: 883.2713; found: 883.2720. |

TABLE 3-continued

| Compounds of general formula 4 obtained in Example 3 | |
|---|---|
| Product: Structure/ Identifier/ Yield | Analytical data |
| 6. 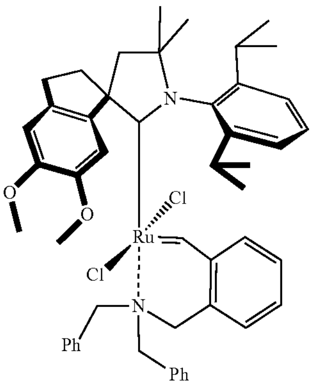 4f/43% | $^{1}H$ NMR (601 MHz, $CD_2Cl_2$) δ 18.42 (s, 1H), 8.60-6.00 (m, 19H), 4.40-2.10 (m, 19H), 1.70-0.90 (m, 16H), 0.60-0.05 (m, 3H).<br>$^{13}C$ NMR (151 MHz, $CD_2Cl_2$) δ 315.5, 313.9, 270.3, 268.4, 150.5, 149.4, 148.9, 147.5, 141.1, 137.0, 135.9, 135.7, 134.6, 133.1, 132.4, 131.4, 129.7, 129.1, 128.5, 128.3, 127.5, 127.4, 126.6, 126.1, 116.9, 116.1, 107.4, 79.0, 72.7, 61.2, 60.5, 58.5, 57.4, 56.9, 56.0, 52.9, 40.1, 39.1, 34.2, 31.8, 29.8, 28.9, 28.2, 27.8, 27.2, 26.7, 25.3, 24.8.<br>HR-MS (ESI) m/z calculated for C50H58ClN2O2Ru [M − Cl]$^+$: 855.3235; found: 855.3235.<br>HR-MS (ESI) m/z calculated for C50H58Cl2N2NaO2Ru [M + Na]$^+$: 913.2819; found: 913.2818. |
| 7. 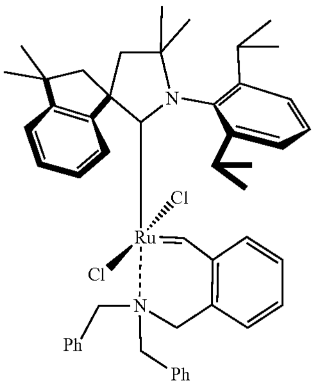 4g/46% | $^{1}H$ NMR (601 MHz, $CD_2Cl_2$) δ 18.28 (s, 1H), 9.50-6.00 (m, 21H), 4.80-2.20 (m, 10H), 2.10-0.90 (m, 23H), 0.60-0.05 (m, 3H).<br>$^{13}C$ NMR (151 MHz, $CD_2Cl_2$) 8 312.7, 268.5, 155.9, 149.6, 148.6, 143.3, 136.5, 136.4, 135.6, 134.8, 132.9, 132.8, 131.6, 129.8, 132.6, 131.4, 129.7, 129.1, 128.4, 128.3, 128.2, 127.5, 127.4, 129.3, 128.7, 128.4, 128.3, 128.1, 127.7, 127.6, 126.7, 126.0, 122.8, 79.3, 71.8, 61.2, 58.3, 57.7, 52.3, 48.9, 44.2, 34.7, 33.0, 29.9, 29.6, 28.5, 28.2, 27.8, 26.5, 26.1, 25.3, 24.6.<br>HR-MS (ESI) m/z calculated for C50H58ClN2Ru [M − Cl]$^+$: 823.3337; found: 823.3336.<br>HR-MS (ESI) m/z calculated for C50H58Cl2N2NaRu [M + Na]$^+$: 881.2921; found: 881.2919. |
| 8. 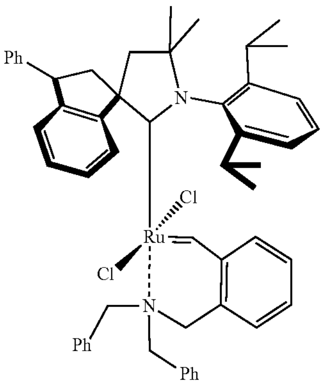 4h/23% | $^{1}H$ NMR (601 MHz, $CD_2Cl_2$) δ 19.00-18.10 (m, 1H), 9.50-6.00 (m, 26H), 5.10-2.10 (m, 12H), 1.70-0.90 (m, 16H), 0.60-0.05 (m, 3H).<br>$^{13}C$ NMR (151 MHz, $CD_2Cl_2$) δ 312.5, 312.2, 267.6, 266.3, 149.3, 148.5, 148.0, 147.1, 146.4, 144.8, 144.2, 136.7, 136.4, 135.4, 134.6, 132.8, 132.5, 131.4, 130.1, 129.9, 129.7, 129.5, 128.9, 128.5, 128.3, 127.7, 127.1, 126.7, 126.3, 125.4, 80.0, 79.5, 72.8, 72.5, 62.7, 62.0, 58.8, 58.5, 57.8, 57.4, 51.9, 50.5, 50.3, 49.8, 49.2, 46.5, 32.4, 30.8, 30.2, 29.9, 29.2, 28.8, 28.4, 28.1, 27.5, 27.1, 26.7, 26.4, 25.2, 24.8.<br>HR-MS (ESI) m/z calculated for C54H58ClN2Ru [M − Cl]$^+$: 871.3338; found: 871.3336.<br>HR-MS (ESI) m/z calculated for C54H58Cl2N2NaRu [M + Na]$^+$: 929.2922; found: 929.2922. |

TABLE 3-continued

Compounds of general formula 4 obtained in Example 3

| Product: Structure/ Identifier/ Yield | Analytical data |
|---|---|
| 9. 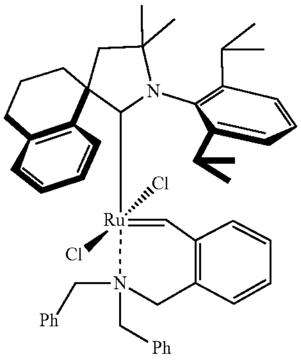 4i/88% | $^{1}H$ NMR (601 MHz, $CD_2Cl_2$) δ 18.37 (s, 1H), 9.20-5.80 (m, 21H), 4.80-2.10 (m, 12H), 2.10-0.90 (m, 19H), 0.60-0.05 (m, 3H). $^{13}C$ NMR (151 MHz, $CD_2Cl_2$) δ 314.4, 269.8, 149.7, 148.9, 148.6, 142.8, 138.5, 137.0, 136.6, 135.8, 135.4, 133.0, 132.6, 131.5, 129.8, 129.5, 129.2, 128.8, 128.5, 128.4, 128.2, 127.4, 127.0, 126.1, 125.5, 79.8, 66.4, 60.6, 58.5, 57.6, 53.2, 34.3, 32.0, 31.2, 30.1, 29.6, 29.2, 29.0, 27.8, 26.0, 25.6, 24.7, 21.4. HR-MS (ESI) m/z calculated for C49H56ClN2Ru [M − Cl]$^+$: 809.3180; found: 809.3180. |
| 10. 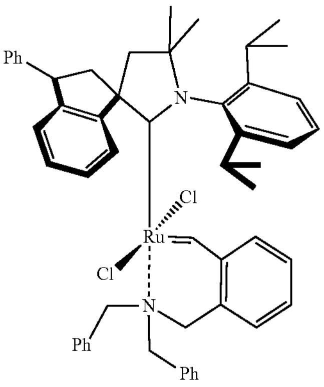 4j/56% | Due to the presence of many isomers, NMR spectra are very complex and the signals are broad. Only characteristic shifts for benzylidene protons and carbene carbons were given. $^{1}H$ NMR (601 MHz, $CD_2Cl_2$) δ 18.79, 18.22, 18.07, 17.93. $^{13}C$ NMR (151 MHz, $CD_2Cl_2$) δ 317.9, 316.04, 269.4, 268.2. HR-MS (ESI) m/z calculated for C46H50Cl2N2NaRu [M + Na]$^+$: 825.2293; found: 825.2304. |
| 11. 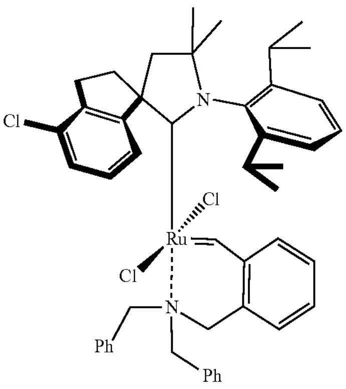 4aa/86% | $^{1}H$ NMR (601 MHz, $CD_2Cl_2$) δ 18.28 (s, 1H), 8.70-6.10 (m, 20H), 4.30-2.10 (m, 12H), 1.60-1.00 (m, 17H), 0.50-0.15 (m, 3H). $^{13}C$ NMR (151 MHz, $CD_2Cl_2$) δ 314.0, 268.3, 149.2, 148.8, 148.7, 146.5, 144.9, 136.8, 136.1, 135.7, 134.6, 133.0, 132.5, 131.7, 131.5, 130.6, 129.9, 129.3, 128.6, 128.5, 128.3, 127.6, 127.3, 126.6, 126.2, 79.2, 73.8, 60.6, 58.3, 57.6, 38.2, 34.0, 31.8, 28.6, 28.4, 27.5, 26.7, 25.3, 24.9. HR-MS (ESI) m/z calculated for C48H54ClN2Ru [M − 2Cl + H]$^+$: 795.3023; found: 795.3023. HR-MS (ESI) m/z calculated for C48H53Cl3N2NaRu [M + Na]$^+$: 887.2215; found: 887.2214. |

Following the same general procedure of Example 3, the following auxiliary complexes 3 (comparative compounds) were prepared for the purpose of providing a fair comparison with the (pre)catalysts of the embodiments described herein.

TABLE 4

| Auxiliary complexes of formula 3 obtained in Example 3 | |
|---|---|
| Product: Structure/ Identifier/ Yield | Analytical data |
| 12. 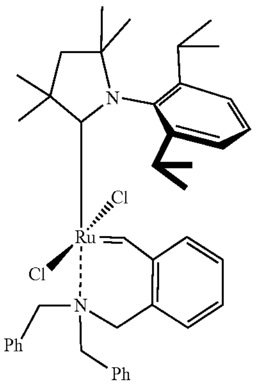 3m/75% | $^{1}H$ NMR (601 MHz, $CD_2Cl_2$) δ 18.51 (s, 1H), 8.43 (d, J = 7.0 Hz, 2H), 7.70-7.05 (m, 12H), 7.00-6.35 (m, 6H), 6.30-6.00 (m, 2H), 5.20-2.45 (br m, 9H), 2.32 (d, J = 12.4 Hz, 1H), 2.02 (br, 2H), 1.80-0.70 (m, 16H), 0.70-0.10 (m, 3H). $^{13}C$ NMR (151 MHz, $CD_2Cl_2$) δ 315.5, 268.8, 148.6, 148.4, 145.4, 136.6, 136.3, 135.9, 135.0, 132.8, 131.2, 129.8, 129.5, 129.3, 128.5, 127.6, 127.3, 126.5, 126.3, 78.7, 64.7, 64.5, 57.9, 47.6, 33.4, 29.6, 28.6, 28.0, 27.5, 27.1, 25.1, 24.8. HR-MS (ESI) m/z calculated for C47H54Cl2N2NaRu [M + Na]+: 841.2607; found: 841.2622. |
| 13. 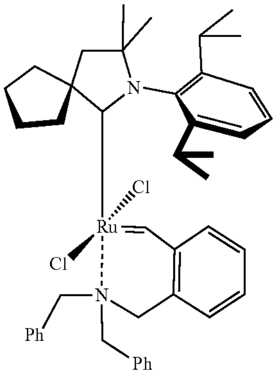 3n/65% | $^{1}H$ NMR (601 MHz, $CD_2Cl_2$) δ 18.55 (s, 1H), 7.59 (t, J = 7.7 Hz, 1H), 7.54 (br, 3H), 7.36 (br, 4H), 7.33 (td, J = 7.4, 1.3 Hz, 1H), 7.04 (td, J = 7.4, 1.2 Hz, 1H), 6.92 (br, 3H), 6.80 (d, J = 7.5 Hz, 1H), 6.64 (br, 2H), 6.38 (dd, J = 7.8, 1.4 Hz, 1H), 4.80-3.10 (m, 7H), 3.10-1.60 (m, 10H), 1.50-0.75 (m, 16H), 0.37 (br, 3H). $^{13}C$ NMR (151 MHz, $CD_2Cl_2$) δ 310.5, 268.0, 148.8, 148.2, 136.5, 135.3, 132.6, 132.1, 129.7, 129.1, 128.6, 128.4, 128.1, 127.9, 126.2, 79.4, 68.2, 61.6, 59.4, 57.4, 50.6, 41.4, 38.3, 30.8, 29.2, 28.7, 27.3, 26.8, 24.8. HR-MS (ESI) m/z calculated for C44H55Cl2N2Ru [M + H]+: 783.2786; found: 783.2780. HR-MS (ESI) m/z calculated for C44H54Cl2N2NaRu [M + Na]+: 805.2606; found: 805.2616. |
| 14. 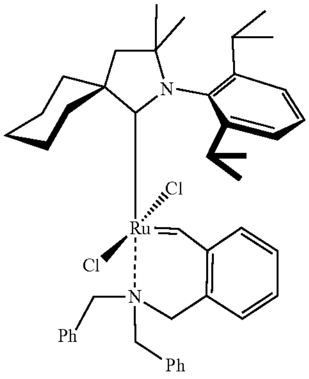 | $^{1}H$ NMR (601 MHz, $CD_2Cl_2$) δ 18.69 (s, 1H), 7.85-7.20 (m, 9H), 7.20-6.90 (m, 4H), 6.85 (d, J = 7.5 Hz, 1H), 6.71 (br, 2H), 6.41 (dd, J = 7.8, 1.4 Hz, 1H), 4.60-4.00 (m, 3H), 3.80-3.05 (m, 4H), 3.00-2.45 (m, 3H), 2.55 (s, 2H), 2.05-1.55 (m, 4H), 1.50-1.05 (m, 16H), 1.05-0.80 (m, 3H), 0.60-0.10 (m, 3H). $^{13}C$ NMR (151 MHz, $CD_2Cl_2$) δ 311.3, 270.0, 148.7, 148.4, 136.4, 135.1, 132.6 (br), 132.2, 129.7, 129.3, 128.6, 128.3, 128.1 (br), 126.2, 79.3, 63.6, 61.1 (br), 59.6, 57.2 (br), 44.7, 36.8 (br), 33.2 (br), 31.6 (br), 29.8 (br), 29.2 (br), 28.4 (br), 27.4 (br), 26.8 (br), 25.9, 24.8 (br), 23.7 (br), 23.4 (br). HR-MS (ESI) m/z calculated for C45H56Cl2N2NaRu [M + Na]+: 819.2763; found: 819.2785. |

Example 4

Preparation of (pre)catalysts of general formula 4 (variants of formula $4_2$), starting from precursor 1b

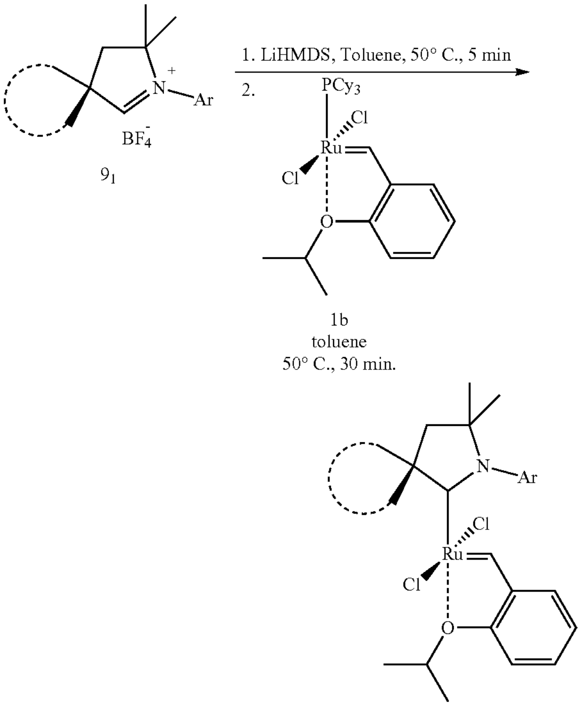

$9_1$ $4_2$

Dry deoxygenated toluene (8 mL) was added under argon to the respective salt of formula $9_1$—CAAC precursor (2.0 mmol, 2 molar eq.). The mixture was heated to 50° C. and a solution of LiHMDS in toluene (1 M, 2.0 mL, 2.0 mmol, 2 molar eq.) was added. After 5 minutes, complex 1b (0.601 g, 1.0 mmol, 1 molar eq.) was added in a solid form. The reaction was carried out at 50° C. for 30 min. The reaction mixture was cooled to room temperature. From this moment, all operations were carried out without a protective argon atmosphere. The reaction mixture was filtered through a Celite pad which was then washed with toluene. The solvent was evaporated and the residue was dissolved in $CH_2Cl_2$ and an excess of n-heptane was added (in the case of (pre) catalysts: 4k, 4n, 4p, 4q, 4ab, 3r) or an excess of methanol (in the case of (pre)catalysts: 4l, 4m, 4o, 4r, 4s, 4t, 3p). $CH_2Cl_2$ was slowly removed in vacuo. Initially precipitating impurities were removed by filtration. After removing all impurities, the product began to crystallize. The obtained crystalline product was filtered off and washed with n-heptane (in the case of (pre)catalysts: 4k, 4n, 4p, 4q, 4ab, 3r) or with methanol (in the case of (pre)catalysts: 4l, 4m, 4o, 4r, 4s, 4t, 3p). It was dried under high vacuum to produce a green crystalline solid as the respective (pre)catalysts of general formula 4 (variants of formula $4_2$).

TABLE 5

Compound of general formula 4 obtained in Example 4

| Product: Structure/ Identifier/ Yield | Analytical data |
|---|---|
| 1 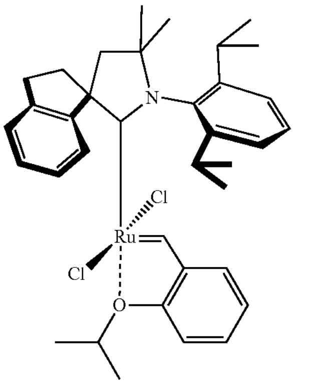 4k/81% | $^1H$ NMR (601 MHz, $CD_2Cl_2$) δ 16.44 (s, 1H), 7.96 (dd, J = 7.1, 1.5 Hz, 1H), 7.66-7.61 (m, 1H), 7.55-7.45 (m, 3H), 7.36-7.24 (m, 3H), 6.88-6.79 (m, 3H), 4.91-4.83 (m, 1H), 3.80-3.72 (m, 1H), 3.34 (ddd, J = 13.0, 10.4, 3.8 Hz, 1H), 3.22-3.14 (m, 1H), 3.14-3.06 (m, 2H), 2.74 (d, J = 12.5 Hz, 1H), 2.44-2.34 (m, 2H), 1.46 (s, 3H), 1.36 (s, 3H), 1.34 (d, J = 6.6 Hz, 3H), 1.30 (d, J = 6.6 Hz, 3H), 1.23 (d, J = 6.1 Hz, 3H), 1.16 (d, J = 6.1 Hz, 3H), 0.81 (d, J = 6.5 Hz, 3H), 0.59 (d, J = 6.3 Hz, 3H). $^{13}C$ NMR (151 MHz, $CD_2Cl_2$) δ 296.2, 296.0, 265.0, 153.3, 149.1, 148.8, 147.8, 143.8, 143.7, 141.5, 136.9, 132.0, 131.1, 130.0, 128.9, 126.4, 126.2, 125.6, 124.5, 123.8, 122.4, 113.6, 78.1, 75.4, 71.8, 39.2, 34.4, 31.4, 29.4, 28.7, 27.9, 27.7, 26.3, 24.8 (2C), 21.8, 21.6. HR-MS (ESI) m/z calculated for C36H45ClNORu $[M - Cl]^+$: 644.2234; found: 644.2231. HR-MS (ESI) m/z calculated for C36H45Cl2NNaORu $[M + Na]^+$: 702.1818; found: 702.1814. |

TABLE 5-continued

| Compound of general formula 4 obtained in Example 4 | |
|---|---|
| Product:<br>Structure/<br>Identifier/<br>Yield | Analytical data |
| 2.<br>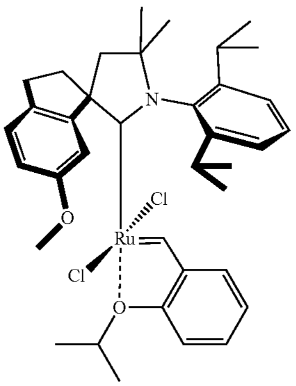<br>4l/82% | $^{1}$H NMR (601 MHz, $CD_2Cl_2$) δ 16.46 (s, 1H), 7.63 (t, J = 7.7 Hz, 1H), 7.61 (d, J = 2.4 Hz, 1H), 7.55-7.45 (m, 3H), 7.21 (dd, J = 8.2, 1.1 Hz, 1H), 6.91-6.79 (m, 4H), 4.90 (sept, J = 6.0 Hz, 1H), 3.90-3.89 (m, 3H), 3.62-3.54 (m, 1H), 3.35 (ddd, J = 12.6, 10.4, 4.1 Hz, 1H), 3.18-3.07 (m, 3H), 2.69 (d, J = 12.5 Hz, 1H), 2.46-2.36 (m, 2H), 1.45 (s, 3H), 1.37 (s, 3H), 1.33 (d, J = 6.8 Hz, 3H), 1.30 (d, J= 6.6 Hz, 3H), 1.27 (d, J = 6.4 Hz, 3H), 1.21 (d, J = 6.1 Hz, 3H), 0.82 (d, J = 6.5 Hz, 3H), 0.59 (d, J = 6.2 Hz, 3H).<br>$^{13}$C NMR (151 MHz, $CD_2Cl_2$) δ 296.3, 265.3, 158.4, 153.3, 149.3, 148.9, 143.8, 142.8, 139.8, 136.9, 131.1, 130.0, 126.4, 126.2, 125.0, 123.8, 122.4, 116.4, 116.3, 113.7, 78.2, 75.5, 72.2, 56.2, 53.3, 39.4, 33.4, 31.6, 29.4, 28.7, 28.0, 27.7, 26.2, 24.9, 24.8, 21.8, 21.7.<br>HR-MS (ESI) m/z calculated for C37H47ClNO2Ru [M − Cl]$^{+}$: 674.2340; found: 674.2360.<br>HR-MS (ESI) m/z calculated for C37H47Cl2NNaO2Ru [M + Na]$^{+}$: 732.1924; found: 732.1944. |
| 3.<br>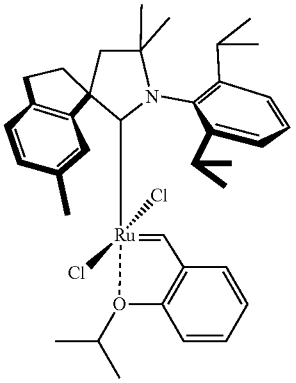<br>4m/74% | $^{1}$H NMR (601 MHz, $CD_2Cl_2$) δ 16.48 (s, 1H), 7.87 (s, 1H), 7.63 (t, J = 7.8 Hz, 1H), 7.54-7.45 (m, 3H), 7.20 (d, J = 7.7 Hz, 1H), 7.13-7.10 (m, 1H), 6.88-6.79 (m, 3H), 4.88 (sept, J = 6.1 Hz, 1H), 3.61 (ddd, J = 16.0, 10.3, 5.8 Hz, 1H), 3.32 (ddd, J = 13.0, 10.4, 4.3 Hz, 1H), 3.19-3.07 (m, 3H), 2.70 (d, J = 12.5 Hz, 1H), 2.43-2.35 (m, 5H), 1.45 (s, 3H), 1.37 (s, 3H), 1.33 (d, J = 6.7 Hz, 3H), 1.31 (d, J = 6.6 Hz, 3H), 1.22 (d, J = 6.1 Hz, 3H), 1.17 (d, J = 6.1 Hz, 3H), 0.82 (d, J = 6.6 Hz, 3H),0.59 (d, J = 6.3 Hz, 3H).<br>$^{13}$C NMR (151 MHz, $CD_2Cl_2$) 8 296.3, 265.6, 153.3, 149.3, 148.9, 144.8, 143.8, 141.2, 136.9, 135.1, 132.7, 131.1, 130.0, 129.6, 126.4, 126.2, 124.2, 123.8, 122.4, 113.6, 78.3, 75.4, 71.8, 53.5, 39.0, 33.9, 31.6, 29.4, 28.7, 28.0, 27.6, 26.2, 24.9, 24.8, 21.7, 21.6 (2C).<br>HR-MS (ESI) m/z calculated for C37H47ClNORu [M − Cl]$^{+}$: 658.2391; found: 658.2390.<br>HR-MS (ESI) m/z calculated for C37H47Cl2NNaORu [M + Na]+: 732.1924; found: 732.1944. |
| 4.<br>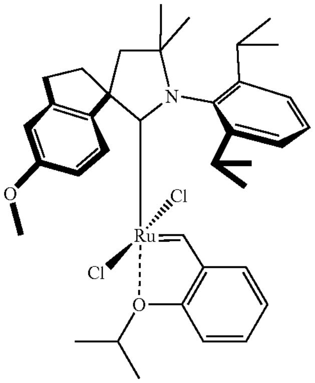<br>4n/84% | $^{1}$H NMR (601 MHz, $CD_2Cl_2$) δ 16.49 (s, 1H), 7.89-7.84 (m, 1H), 7.63 (t, J = 7.8 Hz, 1H), 7.52 (ddd, J = 8.3, 7.1, 1.9 Hz, 1H), 7.49 (dd, J = 7.8, 1.6 Hz, 1H), 7.47 (dd, J = 7.8, 1.6 Hz, 1H), 6.89-6.79 (m, 5H), 4.89 (sept, J = 6.1 Hz, 1H), 3.84 (s, 3H), 3.70 (ddd, J = 16.4, 10.3, 6.2 Hz, 1H), 3.30 (ddd, J = 12.9, 10.4, 3.8 Hz, 1H), 3.17-3.05 (m, 3H), 2.68 (d, J = 12.5 Hz, 1H), 2.43-2.35 (m, 2H), 1.44 (s, 3H), 1.35 (s, 3H), 1.33 (d, J = 6.7 Hz, 3H), 1.29 (d, J = 6.6 Hz, 3H), 1.26 (d, J = 6.1 Hz, 3H), 1.19 (d, J = 6.1 Hz, 3H), 0.81 (d, J = 6.5 Hz, 3H), 0.58 (d, J = 6.3 Hz, 3H).<br>$^{13}$C NMR (151 MHz, $CD_2Cl_2$) δ 296.3, 265.7, 161.2, 153.3, 149.9, 149.2, 148.9, 143.8, 136.9, 133.1, 131.1, 130.0, 126.4, 126.2, 123.8, 122.4, 113.7, 112.2, 109.0, 78.1, 75.4, 71.0, 56.0, 39.5, 34.5, 31.4, 29.4, 28.7, 27.9, 27.6, 26.3, 24.9, 24.8, 21.7, 21.6.<br>HR-MS (ESI) m/z calculated for C37H47ClNO2Ru [M − Cl]$^{+}$: 674.2340; found: 674.2342.<br>HR-MS (ESI) m/z calculated for C37H47Cl2NNaO2Ru [M + Na]$^{+}$: 732.1924; found: 732.1924. |

TABLE 5-continued

Compound of general formula 4 obtained in Example 4

| Product: Structure/ Identifier/ Yield | Analytical data |
|---|---|
| 5. 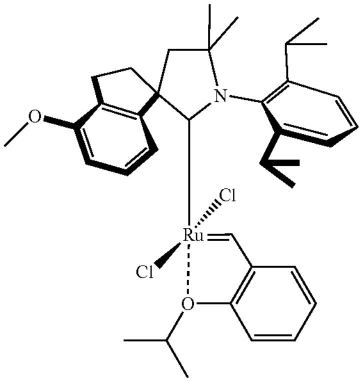 4o/92% | $^{1}H$ NMR (601 MHz, $CD_2Cl_2$) δ 16.44 (s, 1H), 7.63 (t, J = 7.7 Hz, 1H), 7.56-7.44 (m, 4H), 7.28 (t, J = 7.8 Hz, 1H), 6.88-6.78 (m, 4H), 4.88 (sept, J = 6.1 Hz, 1H), 3.89 (s, 3H), 3.62 (ddd, J = 16.5, 10.1, 6.2 Hz, 1H), 3.34 (ddd, J = 13.4, 10.1, 3.6 Hz, 1H), 3.14-3.04 (m, 3H), 2.74 (d, J = 12.6 Hz, 1H), 2.42-2.34 (m, 2H), 1.45 (s, 3H), 1.35-1.32 (m, 6H), 1.30 (d, J = 6.6 Hz, 3H), 1.27 (d, J = 6.1 Hz, 3H), 1.20 (d, J = 6.1 Hz, 3H), 0.80 (d, J = 6.5 Hz, 3H), 0.59 (d, J = 6.3 Hz, 3H). $^{13}C$ NMR (151 MHz, $CD_2Cl_2$) δ 296.0, 264.6, 156.4, 153.3, 149.1, 148.9, 143.8, 143.5, 137.0, 135.6, 131.1, 130.0, 127.2, 126.4, 126.2, 124.0, 123.8, 122.4, 113.7, 110.1, 78.2, 75.4, 72.3, 55.9, 53.7, 39.4, 31.3 (2C), 29.4, 28.7, 27.9, 27.8, 26.4, 24.9, 24.8, 21.7, 21.6. HR-MS (ESI) m/z calculated for C37H47ClNO2Ru [M − Cl]$^+$: 674.2340; found: 674.2358. HR-MS (ESI) m/z calculated for C37H47Cl2NNaO2Ru [M + Na]$^+$: 732.1924; found: 732.1943. |
| 6. 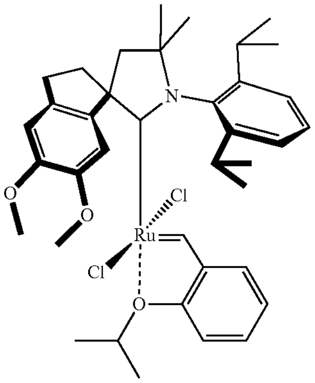 4p/67% | $^{1}H$ NMR (601 MHz, $CD_2Cl_2$) δ 16.50 (s, 1H), 7.63 (t, J = 7.8 Hz, 1H), 7.60 (s, 1H), 7.53 (ddd, J = 8.3, 7.1, 1.9 Hz, 1H), 7.48 (ddd, J = 14.5, 7.8, 1.6 Hz, 2H), 6.89-6.80 (m, 4H), 4.90 (sept, J = 6.0 Hz, 1H), 3.95 (s, 3H), 3.87 (s, 3H), 3.62-3.54 (m,1H), 3.28 (ddd, J = 13.0, 10.4, 4.1 Hz, 1H), 3.18-3.06 (m, 3H), 2.67 (d, J = 12.5 Hz, 1H), 2.43-2.35 (m, 2H), 1.44 (s, 3H), 1.37 (s, 3H), 1.33 (d, J = 6.6 Hz, 3H), 1.29 (d, J = 6.6 Hz, 3H), 1.25 (d, J = 6.1 Hz, 3H), 1.21 (d, J = 6.1 Hz, 3H), 0.83 (d, J = 6.6 Hz, 3H), 0.58 (d, J = 6.3 Hz, 3H). $^{13}C$ NMR (151 MHz, $CD_2Cl_2$) δ 296.6, 266.2, 153.4, 150.8, 149.4, 148.9, 147.6, 143.9, 140.4, 136.8, 132.4, 131.1, 130.0, 126.4, 126.2, 123.8, 122.4, 115.7, 113.7, 107.4, 78.2, 75.4, 72.0, 56.7, 56.5, 53.1, 39.4, 34.2, 31.7, 29.4, 28.7, 28.0, 27.5, 26.2, 24.9, 24.7, 21.7, 21.6. HR-MS (ESI) m/z calculated for C38H49ClNO3Ru [M − Cl]$^+$: 704.2446; found: 704.2441. HR-MS (ESI) m/z calculated for C38H49Cl2NNaO3Ru [M + Na]$^+$: 762.2030; found: 762.2023. |
| 7. 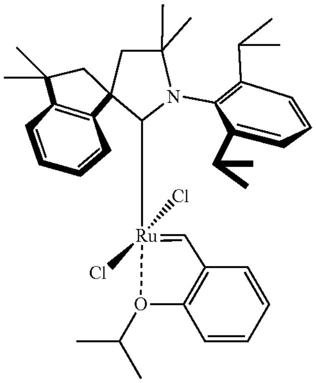 4q/58% | $^{1}H$ NMR (601 MHz, $CD_2Cl_2$) δ 16.41 (s, 1H), 8.44 (d, J = 7.6 Hz, 1H), 7.64 (t, J = 7.7 Hz, 1H), 7.56-7.45 (m, 3H), 7.38-7.33 (m, 1H), 7.32-7.24 (m, 2H), 6.92-6.84 (m, 2H), 6.83-6.79 (m, 1H), 4.97-4.87 (m, 1H), 3.72 (d, J = 12.5 Hz, 1H), 3.27 (sept, J = 6.0 Hz, 1H), 3.06 (sept, J = 6.5 Hz, 1H), 2.66-2.60 (m, 1H), 2.58-2.51 (m, 1H), 2.16 (d, J = 12.5 Hz, 1H), 1.60 (s, 3H), 1.45 (s, 3H), 1.41 (s,3H),1.38-1.24 (m, 15H), 0.83 (d, J = 6.6 Hz, 3H), 0.58 (d, J = 6.3 Hz, 3H). $^{13}C$ NMR (151 MHz, $CD_2Cl_2$) δ 296.0, 264.9, 155.5, 153.4, 149.8, 148.7, 143.7, 142.3, 137.0, 131.1, 130.8, 130.0, 128.8, 126.7, 126.6, 126.2, 123.9, 122.5, 122.4, 113.7, 78.6, 75.5, 71.0, 52.4, 49.8, 44.5, 34.6, 32.7, 32.5, 29.6, 29.5, 28.7, 28.2, 28.0, 26.5, 25.9, 25.0, 24.6, 22.2, 21.8. HR-MS (ESI) m/z calculated for C38H49ClNORu [M − Cl]$^+$: 672.2548; found: 672.2542. HR-MS (ESI) m/z calculated for C38H49Cl2NNaORu [M + Na]$^+$: 730.2131; found: 730.2127. |

TABLE 5-continued

| Compound of general formula 4 obtained in Example 4 | |
|---|---|
| Product: Structure/ Identifier/ Yield | Analytical data |
| 8. 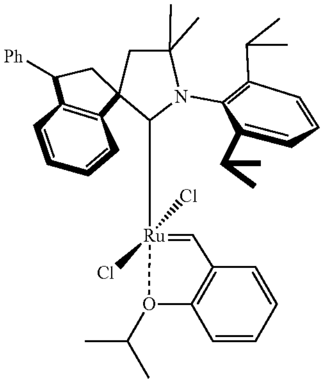 4r/60% | $^{1}$H NMR (601 MHz, $CD_2Cl_2$) δ 16.40 (s, 1H), 8.41 (d, J = 7.0 Hz, 1H), 7.67 (t, J = 7.7 Hz, 1H), 7.60-7.47 (m, 5H), 7.39 (t, J = 7.7 Hz, 2H), 7.30 (t, J = 7.4 Hz, 2H), 7.28-7.22 (m, 1H), 6.98-6.91 (m, 2H), 6.88 (t, J = 7.3 Hz, 1H), 6.85-6.81 (m, 1H), 5.03 (sept, J = 6.1 Hz, 1H), 4.49 (dd, J = 11.2, 6.6 Hz, 1H), 4.16 (t, J = 11.6 Hz, 1H), 3.45-3.35 (m, 1H), 3.02 (sept, J = 6.4 Hz, 1H), 2.83 (dd, J = 12.0, 6.7 Hz, 1H), 2.70 (d, J = 12.6 Hz, 1H), 2.40 (d, J = 12.6 Hz, 1H), 1.51 (d, J = 6.0 Hz, 3H), 1.47 (d, J = 6.1 Hz, 3H), 1.45 (s, 3H), 1.42 (s, 3H), 1.36 (d, J = 6.6 Hz, 3H), 1.27 (d, J = 6.6 Hz, 3H), 0.72 (dd, J = 6.3, 2.6 Hz, 6H).<br>$^{13}$C NMR (151 MHz, $CD_2Cl_2$) δ 295.0, 263.8, 153.4, 149.49, 148.4 (2C), 145.8, 144.1, 143.4, 137.4, 131.3, 130.1, 129.9, 129.0, 128.7, 128.1, 127.3, 126.9, 126.5, 126.4, 125.2, 123.9, 122.4, 113.7, 78.9, 75.6, 71.7, 50.4, 49.4, 49.2, 31.6, 29.6, 29.5, 28.9, 27.5, 26.4, 24.8, 24.7, 22.5, 22.1.<br>HR-MS (ESI) m/z calculated for C42H49ClNORu [M − Cl]$^{+}$: 720.2549; found: 720.2570. |
| 9. 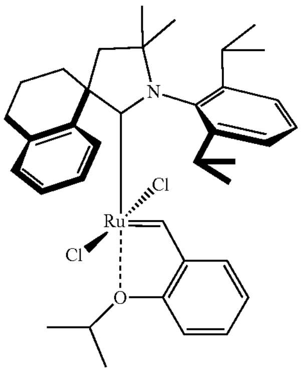 4s/39% | $^{1}$H NMR (601 MHz, $CD_2Cl_2$) δ 16.53 (s, 1H), 8.02 (dd, J = 7.6, 1.8 Hz, 1H), 7.63 (t, J = 7.8 Hz, 1H), 7.55-7.44 (m, 3H), 7.28-7.18 (m, 2H), 7.17-7.11 (m, 1H), 6.90-6.76 (m, 3H), 4.84 (sept, J = 5.8 Hz, 1H), 3.65-3.55 (m, 1H), 3.35-3.22 (m, 2H), 3.20-3.10 (m, 1H), 2.81-2.74 (m, 1H), 2.68 (d, J = 12.9 Hz, 1H), 2.61-2.55 (m, 1H), 2.15-2.08 (m, 1H), 2.00-1.94 (m, 1H), 1.81-1.69 (m, 1H), 1.46 (s, 3H), 1.43 (s, 3H), 1.34-1.28 (m, 6H), 1.23 (d, J = 6.1 Hz, 3H), 1.14 (d, J = 6.1 Hz, 3H), 0.83 (d, J = 6.6 Hz, 3H), 0.56 (d, J = 6.3 Hz, 3H).<br>$^{13}$C NMR (151 MHz, $CD_2Cl_2$) δ 296.9, 296.8, 266.1, 153.4, 149.8, 148.7, 144.0, 142.1, 137.4, 137.2, 135.0, 131.2, 130.0, 128.7, 127.8, 126.7, 126.1, 125.8, 124.0, 122.3, 113.8, 79.0, 75.4, 65.7, 53.7, 34.1, 32.6, 31.0, 29.6, 29.3, 28.4 (2C), 25.8, 25.1, 24.5, 21.8, 21.7 (2C).<br>HR-MS (ESI) m/z calculated for C37H47ClNORu [M − Cl]$^{+}$: 658.2391; found: 658.2398.<br>HR-MS (ESI) m/z calculated for C37H47Cl2NNaORu [M + Na]$^{+}$: 716.1975; found: 716.1979. |
| 10. 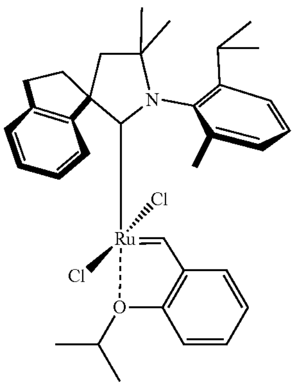 4t/44% | Isomers A:B mixture = 1:0.3<br>$^{1}$H NMR (601 MHz, $CD_2Cl_2$) δ [16.33 (s, A), 16.21 (s, B), 1H], [7.93-7.89 (m, B), 7.83-7.77 (m, A), 1H], 7.58-7.46 (m, A + B, 3H), 7.36-7.24 (m, A + B, 4H), 6.90-6.80 (m, A + B, 3H), 4.92-4.82 (m, A + B, 1H), [3.94-3.80 (m, A), 3.80-3.72 (m,B), 1H], [3.42 (ddd, J = 13.2, 10.1, 3.3 Hz, A), 3.28 (ddd, J = 13.5, 10.3, 3.6 Hz, B), 1H], 3.22-3.14 (m, A + B, 1H), 3.12-3.04 (m, A + B, 1H), [2.81 (d, J = 12.5 Hz, B), 2.75 (d, J = 12.6 Hz, A), 1H],<br>2.46-2.32 (m, A + B, 5H), [1.52 (s, B), 1.48 (s, A), 3H], [1.40 (s, A), 1.39 (s,B), 3H], [1.35 (d, J = 6.7 Hz, B), 1.32 (d, J = 6.6 Hz, A), 3H], [1.23 (d, J = 6.1 Hz,A), 1.20 (d, J = 6.1 Hz, B), 3H], [1.16 (d, J = 6.1 Hz, A), 1.14 (d, J = 6.1 Hz, B), 3H], [0.81 (d, J = 6.6 Hz, B), 0.61 (d, J = 6.4 Hz, A), 3H].<br>Main isomer A:<br>$^{13}$C NMR (151 MHz, $CD_2Cl_2$) δ 298.8, 264.3, 152.9, 149.3, 144.6, 138.7, 138.6, 131.2, 130.2, 129.6, 128.8, 126.4, 125.6, 124.6, 123.9, 122.4, 113.6, 78.5, 75.4, 71.8, 54.1, 39.8, 34.1, 30.8, 29.3, 27.4, 27.1, 24.4, 21.7, 21.6.<br>HR-MS (ESI) m/z calculated for C34H41Cl2NNaORu [M + Na]$^{+}$: 674.1504; found: 674.1515. |

TABLE 5-continued

| Compound of general formula 4 obtained in Example 4 | |
|---|---|
| Product: Structure/ Identifier/ Yield | Analytical data |
| 11. 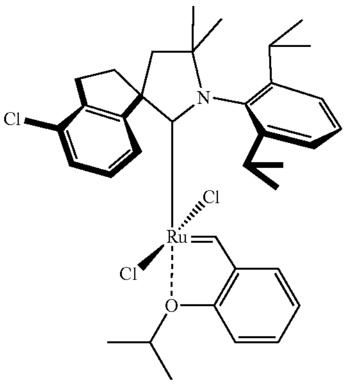 4ab/60% | $^1$H NMR (601 MHz, $CD_2Cl_2$) δ 16.37 (s, 1H), 7.83 (d, J = 7.5 Hz, 1H), 7.64 (t, J = 7.8 Hz, 1H), 7.55-7.45 (m, 3H), 7.32 (dd, J = 7.9, 0.9 Hz, 1H), 7.27 (t, J = 7.7 Hz, 1H), 6.89-6.83 (m, 2H), 6.82-6.79 (m, 1H), 4.90 (sept, J = 5.9 Hz, 1H), 3.80 (ddd, J = 16.8, 10.1, 6.6 Hz, 1H), 3.38 (ddd, J = 13.4, 10.2, 3.5 Hz, 1H), 3.20 (ddd, J = 16.9, 10.3, 3.3 Hz, 1H), 3.11-3.02 (m, 2H), 2.73 (d, J = 12.5 Hz, 1H), 2.44 (d, J = 12.7 Hz, 1H), 2.43-2.38 (m, 1H), 1.46 (s, 3H), 1.36-1.33 (m, 6H), 1.30 (d, J = 6.6 Hz,3H), 1.29 (d, J = 6.1 Hz, 3H), 1.21 (d, J = 6.2 Hz, 3H), 0.80 (d, J = 6.5 Hz, 3H), 0.59 (d, J = 6.3 Hz, 3H). $^{13}$C NMR (151 MHz, $CD_2Cl_2$) δ 296.1, 263.8, 153.4, 149.1, 148.9, 145.7, 144.2, 143.8, 137.0, 131.3, 130.6, 130.3, 130.1, 128.7, 127.5, 126.4, 126.3, 123.9, 122.5, 113.7, 78.2, 75.6, 72.7, 38.8, 34.1, 31.2, 29.4, 28.8, 27.9, 27.8, 26.4, 24.9, 24.8, 21.8, 21.7. HR-MS (ESI) m/z calculated for C36H44Cl2NORu [M − Cl]$^+$: 678.1842; found: 678.1841. HR-MS (ESI) m/z calculated for C36H44Cl3NNaORu [M + Na]$^+$: 736.1426; found: 736.1425. |

Following the same general procedure as in Example 4, the following auxiliary complexes 3 (comparative compounds) were prepared for the purpose affair comparison with the (pre)catalysts of the embodiments described herein.

TABLE 6

| Auxiliary complexes of formula 3 obtained in Example 4 | |
|---|---|
| Product: Structure/ Identifier/ Yield | Analytical data |
| 12. 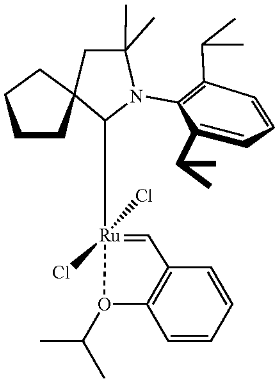 3p/97% | $^1$H NMR (601 MHz, $CD_2Cl_2$) δ 16.37 (s, 1H), 7.63 (t, J = 7.8 Hz, 1H), 7.55 (ddd, J = 8.4, 7.3, 1.7 Hz, 1H), 7.46 (d, J = 7.8 Hz, 2H), 6.98 (d, J = 8.3 Hz, 1H), 6.88 (td, J = 7.4, 0.8 Hz, 1H), 6.82 (dd, J = 7.6, 1.7 Hz, 1H), 5.14 (sept, J = 6.0 Hz, 1H), 3.48-3.40 (m, 2H), 2.95 (sept, J = 6.6 Hz, 2H), 2.20 (s, 2H), 2.17-2.08 (m, 4H), 1.92-1.82 (m, 2H), 1.73 (d, J = 6.1 Hz, 6H), 1.33 (s, 6H), 1.26 (d, J = 6.7 Hz, 6H), 0.66 (d, J = 6.4 Hz, 6H). $^{13}$C NMR (151 MHz, $CD_2Cl_2$) δ 293.9, 265.3, 153.3, 148.9, 143.2, 137.2, 131.0, 130.0, 126.2, 123.9, 122.5, 113.7, 78.6, 75.5, 67.6, 39.5, 30.0, 29.0, 26.8, 26.8, 24.7, 22.5. HR-MS (ESI) m/z calculated for C32H45ClNORu [M − Cl]$^+$: 596.2233; found: 596.2228. HR-MS (ESI) m/z calculated for C32H45Cl2NNaORu [M + Na]$^+$: 654.1817; found: 654.1816. |
| 13. 3r/82% | $^1$H NMR (601 MHz, $CD_2Cl_2$) δ 16.55 (s, 1H), 8.09-8.05 (m, 1H), 7.65 (t, J = 7.8 Hz, 1H), 7.53 (ddd, J = 8.6, 7.4, 1.7 Hz, 1H), 7.51-7.48 (m, 2H), 7.28-7.21 (m, 3H), 6.89 (d, J = 8.3 Hz, 1H), 6.87-6.83 (m, 1H), 6.79 (dd, J = 7.6, 1.8 Hz, 1H), 4.93 (sept, J = 6.1 Hz, 1H), 3.31 (d, J = 13.0 Hz, 1H), 3.17 (sept, J = 6.5 Hz, 1H), 3.03 (sept, J = 6.6 Hz, 1H), 2.60 (s, 3H), 2.58 (s, 3H), 2.27 (d, J = 13.0 Hz, 1H), 1.46 (d, J = 6.1 Hz, 3H), 1.41 (s, 3H), 1.36 (d, J = 6.1 Hz, 3H), 1.30 (d, J = 6.6 Hz, 3H), 1.27-1.25 (m, 6H), 0.71 (d, J= 6.4 Hz, 3H), 0.68 (d, J = 6.4 Hz, 3H). $^{13}$C NMR (151 MHz, $CD_2Cl_2$) δ 295.9, 267.0, 153.3, 149.3, 148.8, 143.6, 141.0, 139.6, 137.5, 133.5, 131.5, 131.3, 130.1, 127.9, 126.5, 126.0, 124.2, 122.3, 113.8, 79.4, 75.4, 63.9, 48.4, 30.9, 29.9, 29.4 (2C), 28.9, 27.2, 27.0, 26.3, 24.8, 24.4, 22.3 (2C). |

TABLE 6-continued

| Auxiliary complexes of formula 3 obtained in Example 4 | |
|---|---|
| Product: Structure/ Identifier/ Yield | Analytical data |
| | HR-MS (ESI) m/z calculated for C36H47Cl2NNaORu [M + Na]+: 704.1974; found: 704.1964. |

Example 5

Preparation of (Pre)Catalysts of General Formula 4 (Variants of Formula $4_3$), Starting from precursor M10.

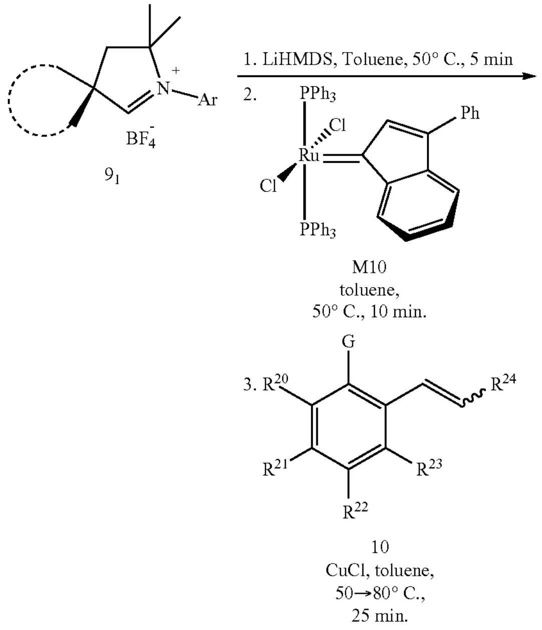

$9_1$ M10 10

-continued

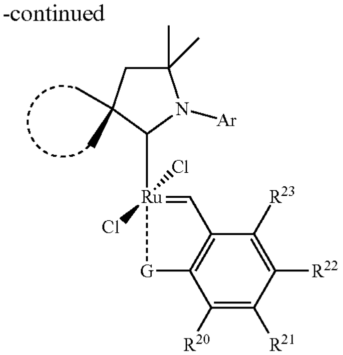

$4_3$

General Synthesis Procedure

Dry deoxygenated toluene (10 mL) was added under argon to the respective salt of formula $9_1$—CAAC precursor (2.0 mmol, 2 molar eq.). The mixture was heated to 50° C. and a solution of LiHMDS in toluene (1 M, 2.0 mL, 2.0 mmol, 2 molar eq.) was added. After 5 minutes, a solid complex of formula M10 (0.887 g, 1.0 mmol, 1 molar eq.) was added. The reaction was carried out for 10 minutes and the respective compound of general formula 10 (styrene derivative or β-substituted styrene derivative; 1.2 mmol, 1.2 molar eq.) and CuCl (0.346 g, 3.5 mmol, 3.5 molar eq.) were added. The reaction mixture was heated to 80° C. (heating time: 10 min). The reaction was carried out for 25 minutes at a temperature of 80° C. The reaction mixture was cooled to room temperature. From this moment, all operations were carried out without a protective argon atmosphere. The crude product was isolated by silica gel column chromatography (eluent: toluene). The green fraction was collected and concentrated to dryness. The residue was dissolved in ethyl acetate and filtered off. The solvent was evaporated, the residue was dissolved in $CH_2Cl_2$ and excess methanol was added. $CH_2Cl_2$ was slowly removed in vacuo. Initially precipitating impurities were removed by filtration. After removing all impurities, the product began to crystallize. The resulting crystalline product was filtered off and washed with methanol. It was dried under high vacuum to produce a green crystalline solid as the corresponding (pre)catalysts of general formula 4 (variants of formula $4_3$).

TABLE 7

| Compounds of general formula 4 obtained in Example 5 | |
|---|---|
| Product: Structure/ Identifier/ Yield | Analytical data |
| 1. | $^1$H NMR (601 MHZ, $CD_2Cl_2$) δ 16.45 (s, 1H), 8.41 (dd, J = 9.1, 2.7 Hz, 1H), 7.95 (d, J = 7.0 Hz, 1H), 7.72 (t, J = 7.8 Hz, 1H), 7.64 (d, J = |

TABLE 7-continued

Compounds of general formula 4 obtained in Example 5

| Product: Structure/ Identifier/ Yield | Analytical data |
|---|---|
| 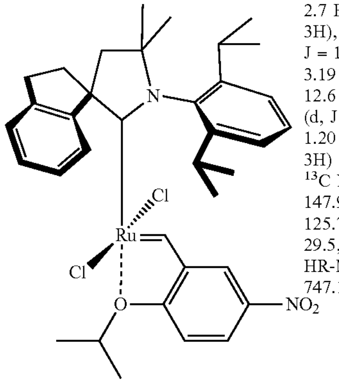 4u/51% | 2.7 Hz, 1H), 7.53 (ddd, J = 17.2, 7.8, 1.6 Hz, 2H), 7.36-7.25 (m, 3H), 6.96 (d, J = 9.0 Hz, 1H), 4.98 (sept, J = 6.1 Hz, 1H), 3.73 (ddd, J = 16.4, 10.2, 6.2 Hz, 1H), 3.33 (ddd, J = 13.1, 10.4, 3.9 Hz, 1H), 3.19 (ddd, J = 16.2, 10.3, 3.7 Hz, 1H), 3.12-3.04 (m, 2H), 2.75 (d, J = 12.6 Hz, 1H), 2.46-2.38 (m, 2H), 1.47 (s, 3H), 1.38 (s, 3H), 1.35 (d, J = 6.6 Hz, 3H), 1.31 (d, J = 6.6 Hz, 3H), 1.26 (d, J = 6.1 Hz, 3H), 1.20 (d, J = 6.1 Hz, 3H), 0.82 (d, J = 6.6 Hz, 3H), 0.59 (d, J = 6.3 Hz, 3H) <br> $^{13}C$ NMR (151 MHz, $CD_2Cl_2$) δ 290.4, 262.4, 157.6, 149.0, 148.7, 147.9, 143.3 (2C), 141.0, 136.6, 132.1, 130.4, 129.1, 126.6, 126.5, 125.7 (2C), 124.6, 118.2, 113.7, 78.7, 78.2, 71.9, 39.2, 34.4, 31.3, 29.5, 28.8, 27.8, 27.7, 26.2, 24.8 (2C), 21.7, 21.6. <br> HR-MS (ESI) m/z calculated for C36H44Cl2N2NaO3Ru $[M + Na]^+$: 747.1669; found: 747.1687. |
| 2. 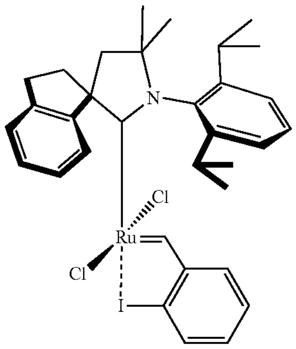 4v/24% | Isomer mixture—ratio 1:5.70 (chemical shifts for benzylidene protons: 18.04 ppm and 17.71 ppm, respectively). <br> Main isomer: <br> $^1H$ NMR (601 MHz, $CD_2Cl_2$) δ 17.71 (s, 1H), 7.55-7.10 (m, 9H), 6.79 (dd, J= 7.5, 1.6 Hz, 1H), 6.55 (dd, J = 7.7, 1.6 Hz, 1H), 4.82 (dt, J = 18.3, 9.5 Hz, 1H), 4.37 (dd, J = 12.9, 7.9 Hz, 1H), 3.76 (sept, J = 6.3 Hz, 1H), 3.45-3.40 (m, 1H), 2.89 (d, J = 12.8 Hz, 1H), 2.67 (ddd, J = 12.9, 10.8, 9.3 Hz, 1H), 2.46-2.39 (m, 1H), 2.31 (d, J = 12.7 Hz, 1H), 1.85 (s, 3H), 1.76 (d, J = 6.3 Hz, 3H), 1.28 (s,3H), 1.24 (d, J = 6.6 Hz, 3H), 1.11 (d, J = 6.6 Hz, 3H), 0.63 (d, J = 6.6 Hz, 3H). <br> $^{13}C$ NMR (151 MHz, $CD_2Cl_2$) δ 299.7, 259.6, 160.6, 148.8, 148.6, 147.6, 141.9, 138.4, 135.9, 134.5, 131.5, 131.4, 130.4, 129.9, 128.9, 127.3, 126.7, 126.4, 125.8, 124.9, 96.3, 79.6, 72.3, 39.5, 34.4, 31.1, 29.6, 28.9, 28.1, 27.7, 26.2, 24.7 (2C). <br> HR-MS (ESI) m/z calculated for C33H38ClINRu $[M - Cl]^+$: 712.0781; found: 712.0785. <br> Isomer mixture. Ratio difficult to determine due to the broad, overlapping signals |
| 3. 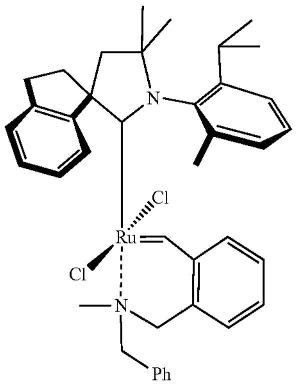 4w/52% | Isomer mixture. Ratio difficult to determine due to the broad, overlapping signals <br> $^1H$ NMR (601 MHz, $CD_2Cl_2$) δ [18.52 (br s), 18 (s), 1H)], 7.65-7.58 (m, 1H), 7.53-6.78 (m, 14H), 6.60-6.50 (m, 1H), 4.30-2.60 (m, 8H), 2.50-2.20 (m, 2H), 1.90-1.60 (m, 3H), 1.52-1.18 (m, 14H), 1.05-0.30 (m, 6H). <br> $^{13}C$ NMR (151 MHz, $CD_2Cl_2$) δ 311.5, 268.7, 149.4 (2C), 148.8 (2C), 148.5, 148.4, 148.0, 147.8, 142.3, 142.1, 136.2, 134.8, 132.7, 132.6, 132.0, 129.8, 129.7, 129.2, 129.1, 128.5 (2C), 128.4, 128.3, 128.2 (2C), 126.6, 126.5, 126.1 (2C), 125.4 (2C), 124.5 (2C), 79.0, 73.0, 72.9, 53.1, 43.3, 34.4, 34.3, 31.7, 29.7, 29.6, 28.5, 28.4, 28.3, 27.6, 27.4, 26.5, 26.4, 25.2, 25.1, 24.9, 24.7. <br> HR-MS (ESI) m/z calculated for C42H50Cl2N2NaRu $[M + Na]^+$: 777.2292; found: 777.2314. |

TABLE 7-continued

Compounds of general formula 4 obtained in Example 5

| Product: Structure/ Identifier/ Yield | Analytical data |
|---|---|
| 4. 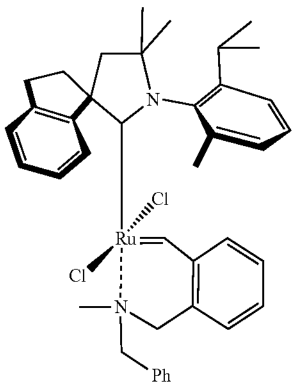 4x/29% | Due to the presence of many isomers, NMR spectra are very complex and the signals are broad. Only characteristic shifts for benzylidene protons and carbene carbons were given. $^1$H NMR (601 MHz, $CD_2Cl_2$) δ 19.02, 19.01, 18.52, 18.50, 18.40, 17.35. $^{13}$C NMR (151 MHz, $CD_2Cl_2$) δ 316.3, 315.0, 314.6, 268.2, 268.0, 267.8. HR-MS (ESI) m/z calculated for C42H49ClN3Ru [M − Cl + $CH_3CN$]$^+$: 732.2661; found: 732.2678. |
| 5. 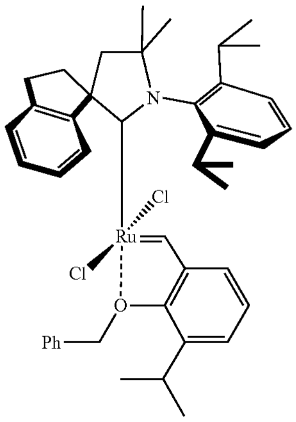 4ac/44% | $^1$H NMR (601 MHz, $CD_2Cl_2$) δ 16.47 (s, 1H), 7.78 (d, J = 7.7 Hz, 1H), 7.65 (t, J = 7.8 Hz, 1H), 7.53-7.46 (m, 3H), 7.32-7.27 (m, 3H), 7.26-7.24 (m, 2H), 7.21-7.17 (m, 2H), 7.17-7.13 (m, 1H), 6.96 (t, J = 7.6 Hz, 1H), 6.60 (dd, J = 7.5, 1.6 Hz, 1H), 5.35-5.32 (m, 1H), 5.22 (d, J = 13.2 Hz, 1H), 3.55 (ddd, J = 16.5, 9.7, 7.2 Hz, 1H), 3.38 (ddd, J = 13.0, 9.7, 3.4 Hz, 1H), 3.20-3.00 (m, 4H), 2.75 (d, J = 12.6 Hz, 1H), 2.38 (d, J = 12.6 Hz, 1H), 2.31 (ddd, J = 12.9, 9.8, 7.3 Hz, 1H), 1.48 (s, 3H), 1.36 (s, 3H), 1.33 (t, J = 6.8 Hz, 6H), 1.14 (d, J = 6.8 Hz, 3H), 1.11 (d, J = 6.8 Hz, 3H), 0.78 (d, J = 6.5 Hz, 3H), 0.67 (d, J = 6.3 Hz, 3H). $^{13}$C NMR (151 MHz, $CD_2Cl_2$) δ 296.0, 263.3, 153.7, 148.9, 148.8, 147.2, 147.1, 142.6, 140.8, 137.4, 137.2, 130.6, 130.1, 129.8, 129.0, 128.8, 127.7, 126.8, 126.5, 126.3, 125.9, 125.8, 124.7, 120.6, 78.2, 77.3, 72.0, 39.7, 34.3, 30.9, 29.4, 28.8, 28.6, 27.7, 27.4, 26.5, 25.1, 25.0, 24.4, 24.1. HR-MS (ESI) m/z calculated for C43H51Cl2NNaORu [M + Na]$^+$: 792.2289; found: 792.2292. |

Example 6

Preparation of (Pre)Catalysts of General Formula 4 (Variants of Formula $4_4$), in which Neutral Ligand L is Phosphine

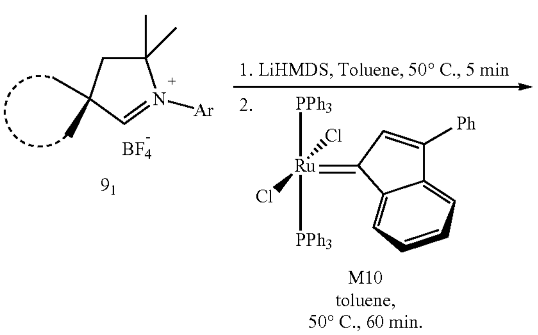

$9_1$

G

-continued

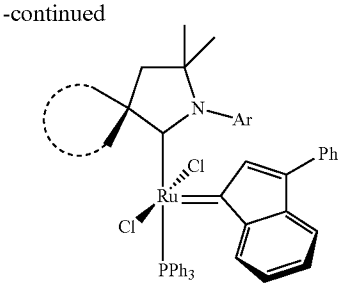

$4_4$

General Synthesis Procedure

Dry deoxygenated toluene (13 mL) was added under argon to the corresponding salt of formula $9_1$—CAAC precursor (2.25 mmol, 1.5 molar eq.). The mixture was heated to 40° C. and a solution of LiHMDS in toluene (1 M, 2.25 mL, 2.25 mmol, 1.5 molar eq.) was added. After 10 minutes, a solid complex of formula M10 (1.33 g, 1.5 mmol, 1 molar eq.) was added. The reaction was carried out for 60 minutes. The reaction mixture was cooled to room temperature. From this moment, all operations were carried out without a protective argon atmosphere. The reaction mixture was filtered through a Celite layer, which was then washed with toluene. The solvent was evaporated and the residue was extracted with $Et_2O$. Excess n-heptane was added to the extract. $Et_2O$ was slowly removed in vacuo. Initially precipitating impurities were removed by filtration. After removing all impurities, the product began to crystallize. The resulting crystalline product was filtered off and washed with n-heptane. It was dried under high vacuum to produce a red-brown crystalline solid as the respective (pre)catalyst of general formula 4 (variant of formula $4_4$).

TABLE 8

Compounds of formula 4 obtained in Example 6

| Product: Structure/ Identifier/ Yield | Analytical data |
|---|---|
| 1. 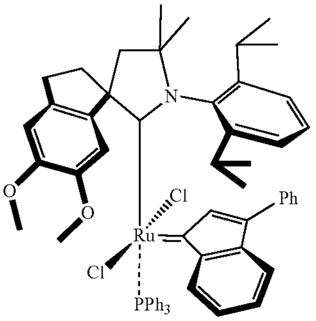 4y/57% | Isomer mixture<br>$^{1}$H NMR (601 MHz, $CD_2Cl_2$) δ 7.80-6.50 (m, 29H), 6.40-5.90 (m, 1H), 4.00-3.25 (m, 6H), 3.20-1.90 (m, 4H), 1.80-0.86 (m, 22H).<br>$^{13}$C NMR (151 MHz, $CD_2Cl_2$) δ 295.7, 295.3, 295.3, 272.7, 272.4, 272.1, 271.8, 197.2, 178.5, 163.2, 150.4, 149.9, 149.8, 149.5, 149.4, 149.3, 149.2 (2C), 149.0 (2C), 148.8, 147.2, 144.8 (2C), 143.1, 142.8, 142.8, 141.5, 140.7, 140.4, 140.1, 139.9, 139.1, 138.8 (2C), 137.7 (2C), 137.3, 137.2 (2C), 136.9 (2C), 136.7, 136.6, 135.1, 135.0 (3C), 134.4, 134.3, 133.8, 133.1, 132.5, 132.4 (3C), 131.9, 131.6, 129.9 (2C), 129.8, 129.5, 129.4, 129.3, 129.0 (2C), 128.7, 128.4, 128.0 (4C), 127.9, 127.4, 126.9, 126.8, 126.5, 125.6, 124.8 (2C), 124.3, 117.5, 116.4, 110.9, 109.1, 108.9, 108.3, 107.8, 107.0 (2C), 106.3, 81.3, 79.1, 78.9 (2C), 76.3, 75.2, 61.5, 57.7, 57.6, 56.8, 56.7, 56.5 (2C), 56.3, 55.9, 55.4, 55.3, 52.2, 51.3, 40.3, 39.4, 37.2, 36.4, 32.4, 32.3, 31.9, 31.6, 31.3, 30.7, 30.3 (2C), 30.1, 29.8, 29.7, 29.5, 29.4, 29.0, 28.8 (2C), 28.3, 28.2, 28.1 (2C), 27.0, 26.8 (2C), 26.7, 26.6, 26.1, 25.7, 25.1, 24.6, 23.7, 23.4, 22.8.<br>$^{31}$P NMR (243 MHz, $CD_2Cl_2$) δ 27.5, 25.6, 21.6. |

Example 7

Preparation of (Pre)Catalysts of General Formula 4 (Variants of Formula 4s), in which Neutral Ligand L is Sulfoxide

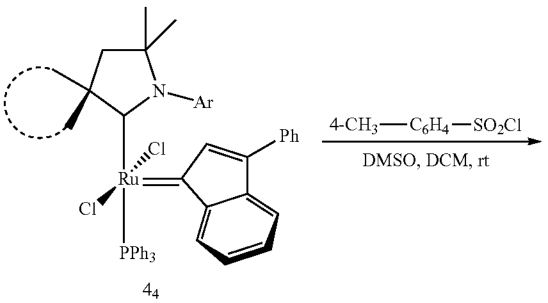

$4_4$

-continued

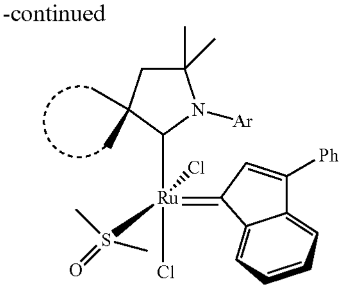

$4_5$

General Synthesis Procedure

A dry $CH_2Cl_2$ (5 ml), respective sulfoxide (2.0 mmol, 4 molar eq.) and tosyl chloride (0.25 mmol, 0.5 molar eq.) were added under argon to the corresponding complex of formula $4_4$ (0.5 mmol, 1 molar eq). The whole mixture was stirred for 90 minutes in room temperature. The reaction mixture was filtered through Celite and excess tert-butyl methyl ether was added. $CH_2Cl_2$ was removed slowly in vacuo. The resulting crystalline product was filtered off and washed with cold tert-butyl methyl ether. It was dried under high vacuum to yield a brown crystalline solid as the respective (pre)catalyst of formula 4 (variant of formula $4_5$).

-continued

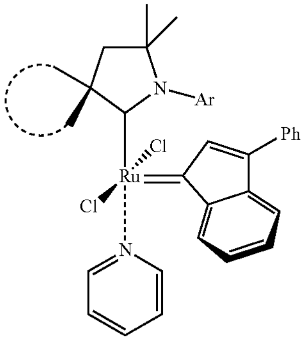

$4_5$

TABLE 9

Compounds of general formula 4 obtained in Example 7

| Product: Structure/ Identifier/ Yield | Analytical data |
|---|---|
| 1. 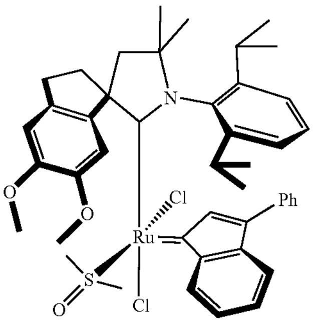 4z/62% | Due to the presence many isomers, NMR spectra are very complex and peaks are broad. Only main signals of $^{13}C$ NMR spectrum were given. $^{13}C$ NMR (151 MHz, $CD_2Cl_2$) δ 293.0, 265.7, 150.0, 149.6, 149.3, 148.7, 146.2, 142.5, 141.6, 139.1, 138.3, 137.5, 136.9, 135.3, 132.5, 132.4, 131.2, 131.1, 131.1, 130.2, 129.5, 129.0, 128.9, 127.3, 118.6, 111.8, 107.0, 80.2, 77.6, 58.1, 55.3, 52.1, 49.6, 48.5, 44.4, 39.5, 32.4, 31.2, 30.2, 30.1, 29.1, 28.6, 27.2, 26.6, 26.2, 25.8. HR-MS (ESI) m/z calculated for C39H46NO2RuS [M − 2C]−C6H8O + H]$^+$: 694.2297; found: 694.2298. |

Example 8

Preparation of (Pre)Catalysts of General Formula 4 (Variants of Formula $4_6$), in which Neutral Ligand L is Pyridine

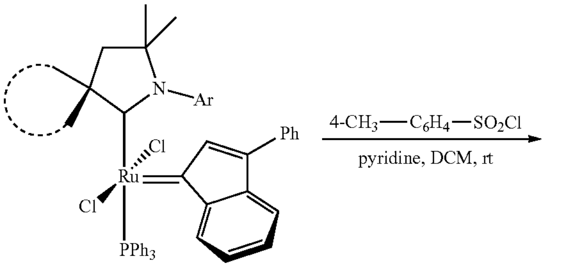

$4_4$

General Synthesis Procedure

Dry $CH_2Cl_2$ (5 mL), the appropriate pyridine (2.0 mmol, 4 molar equivalent) and tosyl chloride (0.25 mmol, 0.5 molar eq.) were added under argon to the appropriate complex of formula $4_4$ (0.5 mmol, 1 molar eq.), The mixture was stirred for 90 minutes in room temperature. The reaction mixture was filtered through Celite and excess heptane was added. $CH_2Cl_2$ was removed slowly in vacuo. Initially precipitating impurities were removed by filtration. After removing all impurities, the product began to crystallize. The mixture was cooled to −20° C. The resulting crystalline product was filtered off and washed with cold n-heptane. Dried under high vacuum to produce a brown crystalline solid as the corresponding (pre)catalyst of general formula 4 (variant of formula $4_6$).

TABLE 10

| Compounds of general formula 4 obtained in Example 8 | |
|---|---|
| Product: Structure/ Identifier/ Yield | Analytical data |
| 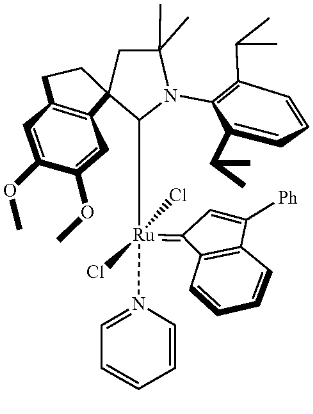 4ad/80% | Due to the complex $^{1}H$ NMR spectrum, only $^{13}C$ NMR spectrum was described. $^{13}C$ NMR (151 MHz, $CD_2Cl_2$) δ 303.0, 264.1, 158.8, 153.1, 151.1, 148.6, 148.0, 143.3, 142.8, 142.5, 141.6, 139.7, 137.7, 137.2, 135.7, 133.8, 133.1, 132.5, 132.4 (3C), 130.0, 129.5, 129.2 (2C), 129.1, 129.0, 128.5, 127.8, 127.4, 126.7, 126.5, 126.0, 125.6, 124.8, 123.7, 123.4, 117.9, 116.5, 107.9, 79.6, 71.0, 56.71, 56.34, 34.6, 32.4, 28.3, 27.5, 26.8, 25.8, 22.9, 14.4. |

Example 9

Preparation of (Pre)Catalysts of General Formula 4 (Variants of Formula $4_2$), Starting from (Pre)Catalysts of Formula $4_5$ (Complexes of General Formula 4, Wherein Neutral Ligand is Sulfoxide)

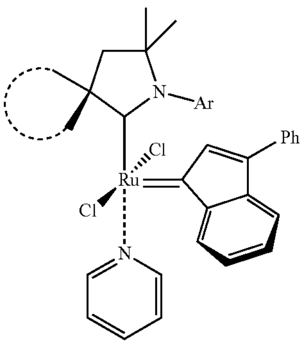

$4_5$

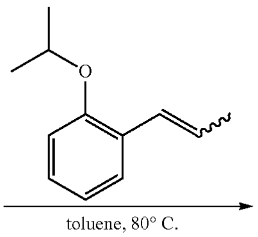

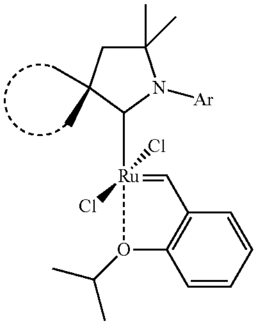

$4_2$

General Synthesis Procedure

Dry toluene (2 mL) and 2-isopropoxy-1-prop-2'-enylbenzene were added under argon to the respective (pre)catalyst of formula $4_5$ (0.2 mmol, 1 molar eq.). The reaction mixture was heated to 80° C. and the reaction was carried out for 30 minutes. The reaction mixture was cooled to room temperature. From this moment, all operations were carried out without a protective argon atmosphere. The crude product was isolated by column chromatography on silica gel (eluent: toluene). The green fraction was collected and concentrated to dryness. The residue was dissolved in $CH_2Cl_2$ and excess methanol was added. $CH_2Cl_2$ was slowly removed in vacuo. Initially precipitating impurities were removed by filtration. After removing all impurities, the product began to crystallize. The resulting crystalline product was filtered off and washed with methanol. It was dried under high vacuum to produce a green crystalline solid as the corresponding (pre)catalyst of Formula $4_2$.

TABLE 11

| Compounds of general formula 4 obtained in Example 8 | |
|---|---|
| Product: Structure/ Identifier/ Yield | Analytical data |
| 4p/40% | Analytical data in accordance with the analytical data as cited in Example 4 (position 6) |

Example 10

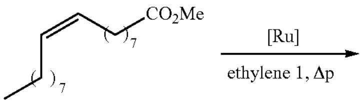

methyl oleate

-continued

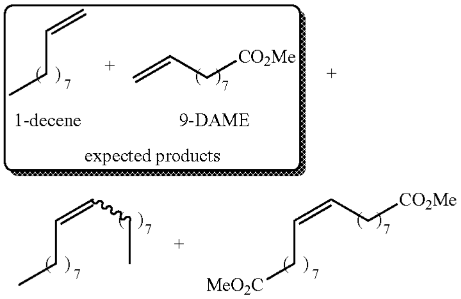

1-decene

9-DAME expected products side products

Cross metathesis reactions involving ethylene were carried out with methyl oleate having a purity >99%. The reactions were carried out according to the above-mentioned general procedure for carrying out the ethenolysis reaction. The results are shown in Table 12 below:

TABLE 12

Parameters of cross metathesis reaction involving methyl oleate and using compounds of formulas 3 and 4

| Catalyst (amount [ppm]) | Conversion [%] | 9-DAME yield [%] | 9-DAME selectivity [%] | $TON_{EFFECT}$ |
|---|---|---|---|---|
| 4a (1) | 59.6 | 57.4 | 96.3 | 574000 |
| 4a (0.5) | 43.3 | 42.4 | 98.0 | 848000 |
| 4a (0.25) | 31.7 | 31.4 | 99.0 | 1260000 |
| 4f (1) | 76.8 | 70.3 | 91.5 | 703000 |
| 4f (0.5) | 62.2 | 59.2 | 95.2 | 1180000 |
| 4f (0.25) | 45.4 | 43.9 | 96.7 | 1760000 |
| 4f (0.1) | 23.1 | 23.0 | 99.4 | 2300000 |
| 4aa (1) | 69.1 | 65.2 | 94.3 | 652000 |
| 4aa (0.5) | 58.7 | 56.6 | 96.5 | 1130000 |
| 4aa (0.25) | 41.5 | 40.7 | 98.0 | 1630000 |
| 4aa (0.1) | 23.3 | 23.0 | 98.9 | 2300000 |
| 4i (1) | 53.4 | 52.1 | 97.5 | 521000 |
| 4i (0.5) | 43.1 | 42.4 | 98.3 | 848000 |
| 4i (0.25) | 29.4 | 29.1 | 99.0 | 1164000 |
| 4k (1) | 63.9 | 60.7 | 95.0 | 607000 |
| 4k (0.5) | 46.1 | 45.2 | 98.0 | 904000 |
| 4k (0.25) | 32.2 | 32.0 | 99.4 | 1280000 |
| 4p (1) | 77.3 | 70.6 | 91.3 | 706000 |
| 4p (0.5) | 62.2 | 59.3 | 95.4 | 1190000 |
| 4p (0.25) | 45.5 | 44.2 | 97.2 | 1770000 |
| 4p (0.1) | 26.4 | 26.1 | 98.7 | 2610000 |
| 4ab (1) | 76.2 | 70.6 | 92.7 | 706000 |
| 4ab (0.5) | 59.3 | 57.0 | 96.1 | 1140000 |
| 4ab (0.25) | 45.5 | 44.5 | 97.8 | 1780000 |
| 4ab (0.1) | 26.1 | 25.9 | 99.3 | 2590000 |
| 4s (1) | 61.8 | 59.6 | 96.4 | 596000 |
| 4s (0.5) | 41.9 | 41.2 | 98.4 | 824000 |
| 4s (0.25) | 31.2 | 31.0 | 99.3 | 1240000 |
| 3j (1) | 41.0 | 37.8 | 92.2 | 378000 |
| 3j (0.5) | 25.2 | 23.6 | 93.5 | 472000 |
| 3j (0.25) | 15.6 | 15.1 | 96.6 | 604000 |
| 3k (1.0) | 42.7 | 40.7 | 95.4 | 407000 |
| 3k (0.5) | 26.3 | 25.6 | 97.3 | 512000 |
| 3l (1) | 37.0 | 36.8 | 99.4 | 368000 |
| 3l (0.5) | 26.2 | 26.0 | 99.6 | 520000 |
| 3l (0.25) | 15.6 | 15.6 | 99.7 | 624000 |

Example 11

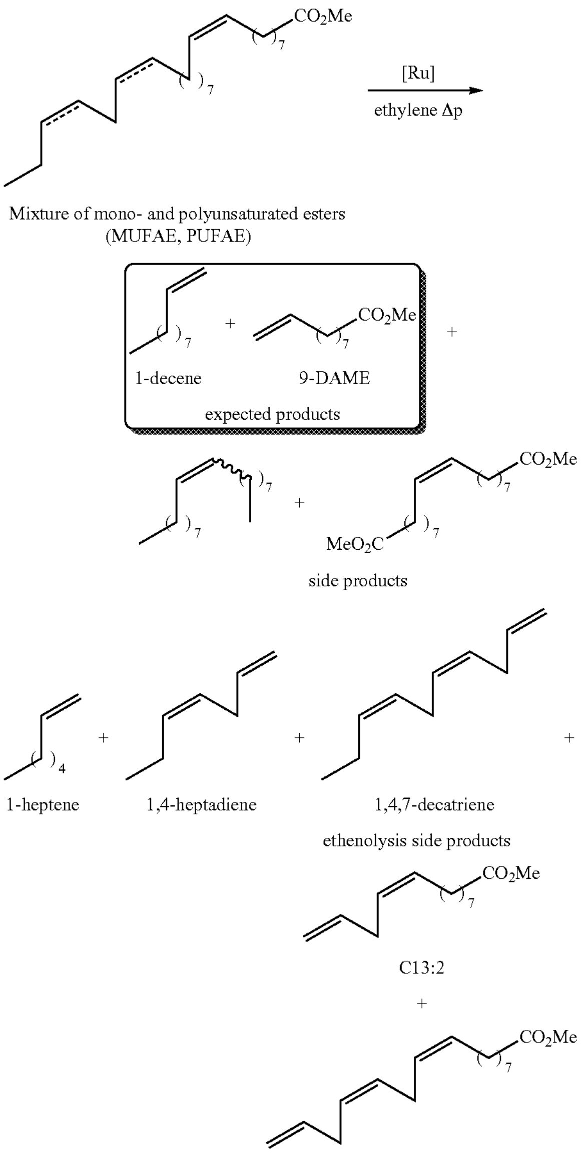

Mixture of mono- and polyunsaturated esters (MUFAE, PUFAE)

1-decene

9-DAME expected products side products 1-heptene 1,4-heptadiene 1,4,7-decatriene ethenolysis side products

C13:2

C16:3

Cross metathesis reactions involving ethylene were carried out with methyl esters derived from transesterification of high oleate sunflower oil having fatty acids profiles as presented below:

C16:0 2.24%,

C18:0 1.36%,

C18:1 93.09%,

C18:2 2.65%,

C18:3 0.34%.

The reactions were carried out according to the above-mentioned general procedure for carrying out the ethenolysis reaction. In the case of (pre)catalysts 4w and 4x the reactions were carried out at a temperature of 60° C. The results are provided in Table 13 below:

TABLE 13

| Parameters of cross metathesis reaction involving methyl esters derived from transesterification of high oleate sunflower oil and using compounds of formulas 3 and 4 | | | | |
|---|---|---|---|---|
| Catalyst (amount [ppm]) | Conversion [% | 9-DAME yield [%] | 9-DAME selectivity [%] | $TON_{EFFECT}$ |
| 4a (1) | 48.0 | 46.1 | 96.0 | 461000 |
| 4a (0.5) | 30.1 | 29.1 | 96.7 | 582000 |
| 4b (1) | 53.2 | 50.0 | 94.0 | 500000 |
| 4c (1) | 51.9 | 49.8 | 95.9 | 498000 |
| 4d (1) | 49.0 | 46.7 | 95.3 | 467000 |
| 4e (1) | 54.3 | 51.7 | 95.2 | 517000 |
| 4f (1) | 65.2 | 61.4 | 94.2 | 614000 |
| 4f (0.5) | 49.7 | 48.0 | 96.5 | 960000 |
| 4g (1) | 49.6 | 47.1 | 94.9 | 471000 |
| 4h (1) | 55.7 | 52.9 | 95.0 | 529000 |
| 4i (1) | 44.2 | 42.7 | 96.6 | 427000 |
| 4i (0.5) | 27.3 | 26.4 | 96.8 | 528000 |
| 4aa (1) | 60.5 | 57.6 | 95.2 | 576000 |
| 4j (1) | 33.1 | 28.8 | 87.1 | 288000 |
| 4k (1) | 52.4 | 50.2 | 95.8 | 502000 |
| 4k (0.5) | 31.9 | 30.9 | 96.9 | 618000 |
| 4l (1) | 56.4 | 53.5 | 94.9 | 535000 |
| 4m (1) | 53.4 | 51.3 | 96.0 | 513000 |
| 4n (1) | 49.2 | 47.1 | 95.7 | 471000 |
| 4o (1) | 56.2 | 53.8 | 95.7 | 538000 |
| 4p (1) | 66.1 | 62.3 | 94.2 | 623000 |
| 4p (0.5) | 50.4 | 48.2 | 95.6 | 964000 |
| 4q (1) | 53.2 | 50.8 | 95.5 | 508000 |
| 4r (1) | 55.5 | 52.8 | 95.1 | 528000 |
| 4s (1) | 49.6 | 48.0 | 96.8 | 480000 |
| 4s (0.5) | 30.5 | 29.6 | 97.2 | 592000 |
| 4ab (1) | 68.2 | 64.3 | 94.3 | 643000 |
| 4t (1) | 37.0 | 31.9 | 86.3 | 319000 |
| 4u (1) | 48.8 | 47.0 | 96.4 | 470000 |
| 4v (1) | 46.8 | 45.3 | 96.9 | 453000 |
| 4w (1) | 33.6 | 32.8 | 97.5 | 328000 |
| 4ac (1) | 50.3 | 48.6 | 96.6 | 486000 |
| 4x (1) | 36.1 | 32.1 | 88.9 | 321000 |
| 4y (1) | 42.4 | 41.0 | 96.8 | 410000 |
| 4z (1) | 42.8 | 41.3 | 96.4 | 413000 |
| 4ad (1) | 49.6 | 47.7 | 96.1 | 477000 |
| 3m (1) | 21.7 | 21.1 | 97.4 | 211000 |
| 3m (0.5) | 12.6 | 12.2 | 97.0 | 244000 |
| 3l (1) | 26.2 | 25.4 | 96.8 | 254000 |
| 3l (0.5) | 17.7 | 17.4 | 98.3 | 348000 |
| 3r (1) | 22.9 | 22.3 | 97.4 | 223000 |
| 3j (1) | 18.9 | 17.1 | 90.7 | 171000 |
| 3j (0.5) | 14.5 | 13.7 | 94.3 | 274000 |
| 3k (1) | 26.2 | 25.4 | 97.1 | 254000 |
| 3k (0.5) | 16.4 | 16.3 | 99.6 | 326000 |
| 3n (1) | 4.2 | 4.1 | 96.6 | 41000 |
| 3p (1) | 4.0 | 3.8 | 96.0 | 38000 |
| 3o (1) | 4.7 | 4.6 | 98.3 | 46000 |
| 3c (1) | 6.0 | 5.9 | 98.8 | 59000 |

Example 12

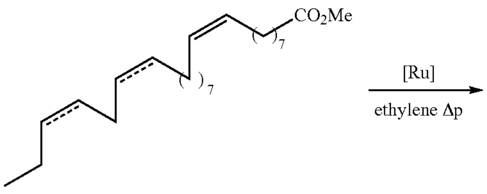

Mixture of mono- and polyunsaturated esters (MUFAE, PUFAE)

-continued

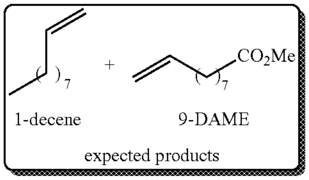

1-decene + 9-DAME expected products

+

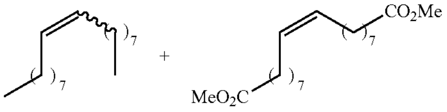

side products

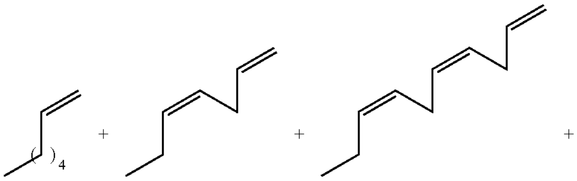

1-heptene + 1,4-heptadiene + 1,4,7-decatriene + ethenolysis side products

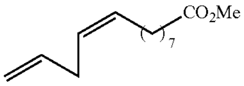

C13:2

+

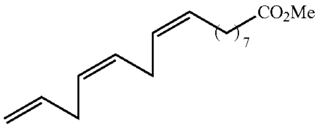

C16:3

Cross metathesis reactions involving ethylene were carried out with methyl esters derived from transesterification of rapeseed oil having fatty acids profile as presented below:

C16:0 2.03%,

C18:0 1.65%,

C18:1 68.55%,

C18:2 19.44%,

C18:3 7.87%.

Reactions were carried out according to above-mentioned general procedure for carrying out the ethenolysis reaction. The results are provided in Table 14 below:

TABLE 14

| Parameters of cross metathesis reaction involving methyl esters derived from transesterification of rapeseed oil and using compounds of formulas 3 and 4 | | | | |
|---|---|---|---|---|
| Catalyst (amount [ppm]) | Conversion [%] | 9-DAME yield [%] | 9-DAME selectivity [%] | $TON_{EFFECT}$ |
| 4a (1) | 50.7 | 42.1 | 83.0 | 421000 |
| 4a (0.5) | 30.0 | 23.0 | 76.8 | 460000 |
| 4e (1) | 56.8 | 47.8 | 84.1 | 478000 |
| 4d (1) | 52.5 | 43.6 | 83.0 | 436000 |
| 4b (1) | 51.0 | 41.9 | 82.1 | 419000 |
| 4c (1) | 50.3 | 41.4 | 82.3 | 414000 |
| 4f (1) | 66.1 | 56.6 | 85.7 | 566000 |
| 4f (0.5) | 37.3 | 29.5 | 79.1 | 590000 |
| 4g (1) | 55.6 | 46.6 | 83.9 | 466000 |
| 4h (1) | 55.5 | 46.4 | 83.6 | 464000 |
| 4aa (1) | 56.6 | 47.5 | 83.9 | 475000 |
| 4aa (0.5) | 42.0 | 33.7 | 80.2 | 674000 |

TABLE 14-continued

Parameters of cross metathesis reaction involving methyl esters derived from transesterification of rapeseed oil and using compounds of formulas 3 and 4

| Catalyst (amount [ppm]) | Conversion [%] | 9-DAME yield [%] | 9-DAME selectivity [%] | $TON_{EFFECT}$ |
|---|---|---|---|---|
| 4i (1) | 42.3 | 34.2 | 80.8 | 342000 |
| 4i (0.5) | 34.6 | 26.8 | 77.4 | 536000 |
| 4j (1) | 36.2 | 24.1 | 66.5 | 241000 |
| 4k (1) | 54.6 | 45.8 | 83.9 | 458000 |
| 4k (0.5) | 32.0 | 24.4 | 76.3 | 488000 |
| 4o (1) | 53.9 | 44.9 | 83.3 | 449000 |
| 4n (1) | 52.8 | 43.6 | 82.6 | 436000 |
| 4l (1) | 60.1 | 51.0 | 84.8 | 510000 |
| 4m (1) | 51.3 | 42.3 | 82.5 | 423000 |
| 4p (1) | 67.1 | 57.6 | 85.8 | 576000 |
| 4p (0.5) | 43.1 | 33.8 | 78.5 | 676000 |
| 4q (1) | 57.5 | 48.5 | 84.4 | 485000 |
| 4r (1) | 58.7 | 49.4 | 84.1 | 494000 |
| 4ab (1) | 61.1 | 52.1 | 85.2 | 521000 |
| 4ab (0.5) | 44.3 | 35.9 | 81.0 | 718000 |
| 4s (1) | 47.5 | 38.8 | 81.7 | 388000 |
| 4s (0.5) | 35.6 | 27.8 | 78.1 | 556000 |
| 4t (1) | 36.8 | 28.0 | 76.0 | 280000 |
| 3j (1) | 20.6 | 14.8 | 71.9 | 148000 |
| 3j (0.5) | 12.4 | 8.5 | 68.6 | 170000 |
| 3k (1) | 26.3 | 20.4 | 77.5 | 204000 |
| 3k (0.5) | 16.5 | 12.3 | 74.6 | 246000 |
| 3l (1) | 26.4 | 19.8 | 75.0 | 198000 |
| 3l (0.5) | 11.9 | 8.3 | 70.1 | 166000 |
| 3r (1) | 28.9 | 22.0 | 76.0 | 220000 |
| 3m (1) | 25.7 | 19.0 | 74.1 | 190000 |
| 3m (0.5) | 16.9 | 12.0 | 71.1 | 240000 |

The results presented in Examples 10-12 above confirm that the ruthenium (pre)catalysts containing the CAAC ligand described by the general formula 4 are much more effective than the catalysts known in the art, not only in the case of metathesis reaction carried out with model methyl oleate, but also in the case of readily available industrial raw materials. The TON values obtained for the compounds of the general formula 4 were even several times higher than the results obtained using the known comparative compounds.

The invention claimed is:

1. A compound of general Formula 4

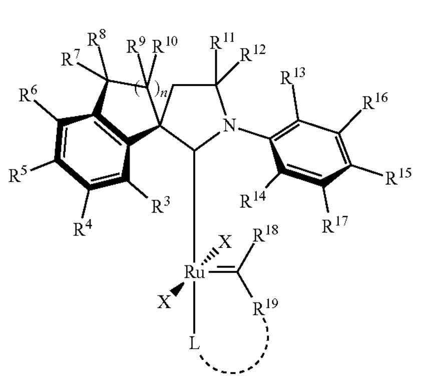

4 wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2$R', —$CH_2$NR'R", —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', wherein R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, wherein R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'''), amide group (—CONR'''R''''), formyl group (—CHO), ketone group (—COR'''), and hydroxamic group (—CON(OR''')(R'''')), wherein R''' and R'''' independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R" or R''' and R'''' are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R''' and R'''' are optionally linked to each other, X denotes halogen atom, and n is 1 or 2, wherein L and $R^{19}$ are optionally linked to each other.

2. The compound of general formula 4 according to claim 1, wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ are selected from the group comprising hydrogen atom, alkyl group $C_1$-$C_6$, alkoxy group $C_1$-$C_6$, halogen atom, and aryl group $C_6$-$C_{10}$, $R^{18}$ denotes hydrogen atom, $R^{19}$ denotes aryl group $C_6$-$C_{10}$ optionally substituted with at least one alkyl group $C_1$-$C_6$ or —$NO_2$, or $R^{18}$ and $R^{19}$ are optionally linked to each other thereby forming an aromatic polycyclic system, L denotes a neutral ligand selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, aryl group $C_6$-$C_{20}$, heteroaryl group $C_4$-$C_{20}$, alkoxy group $C_1$-$C_6$, or aralkyl group $C_7$-$C_{24}$, or halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, and X denote halogen atom, wherein L and $R^{19}$ are optionally linked to each other.

3. The compound of general formula 4 according to claim 1, wherein $R^3$, $R^9$, $R^{10}$, $R^{15}$, $R^{16}$, $R^{17}$ and $R^{18}$ denote hydrogen atom, $R^4$ denotes hydrogen atom, alkyl group $C_1$-$C_6$, or alkoxy group $C_1$-$C_6$, $R^5$ denotes hydrogen atom or alkoxy group $C_1$-$C_6$, $R^6$ denotes hydrogen atom, alkoxy group $C_1$-$C_6$ or halogen atom, $R^7$ and $R^8$ denote hydrogen atom, alkyl group $C_1$-$C_6$, or aryl group $C_6$-$C_{10}$, $R^{11}$ and $R^{12}$ denote alkyl group $C_1$-$C_6$, $R^{13}$ denotes alkyl group $C_1$-$C_6$, $R^{14}$ denotes alkyl group $C_1$-$C_6$, $R^{19}$ denotes aryl group $C_6$-$C_{10}$ optionally substituted with at least one alkyl group $C_1$-$C_6$ or —$NO_2$, or $R^{18}$ and $R^{19}$ are optionally linked to each other, forming an aromatic polycyclic system, L denotes a neutral ligand selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, aryl group $C_6$-$C_{20}$, heteroaryl group $C_4$-$C_{20}$, alkoxy group $C_1$-$C_6$, or aralkyl group $C_7$-$C_{24}$ or halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, X denote halogen atom, and wherein L and $R^{19}$ are optionally linked to each other.

4. The compound of general formula 4 according to claim 1, wherein $R^3$, $R^9$, $R^{10}$, $R^{15}$, $R^{16}$, $R^{17}$ and $R^{18}$ denote hydrogen atom, $R^4$ denotes hydrogen atom, methyl group or methoxy group, $R^5$ denotes hydrogen atom or methoxy group, $R^6$ denotes hydrogen atom, methoxy group or chlorine atom, $R^7$ and $R^8$ denote hydrogen atom, methyl group or phenyl group, $R^{11}$ and $R^{12}$ denote methyl group, $R^{13}$ denotes isopropyl group, $R^{14}$ denotes methyl group or isopropyl group, $R^{19}$ denotes benzyl group or phenyl group optionally substituted with isopropyl group or nitro group, or $R^{18}$ and $R^{19}$ together form phenylindenylidene group, L denotes a neutral ligand selected from the group comprising dibenzylamine, benzylmethylamine, isopropyl ether or benzyl ether, iodine atom, triphenylphosphine, dimethylsulfoxide, and pyridine, and X denotes chlorine atom, wherein L and $R^{19}$ are optionally linked to each other.

5. The compound of general formula 4 according to claim 1, which is selected from the group comprising the following compounds:

4a

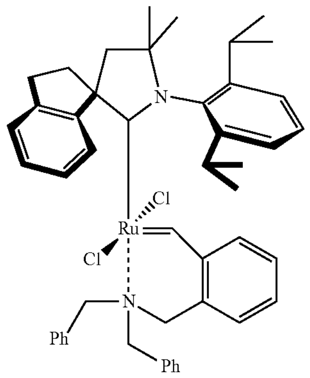

4b

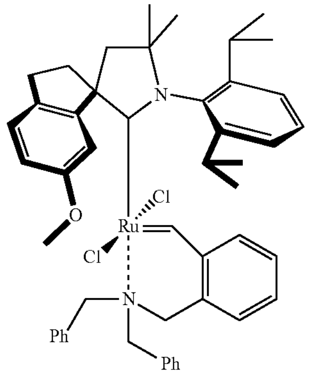

-continued
4c
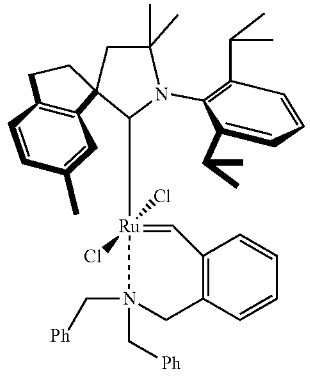
4d
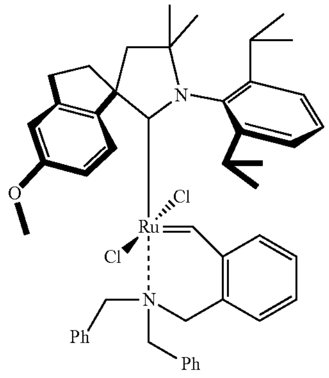
4e
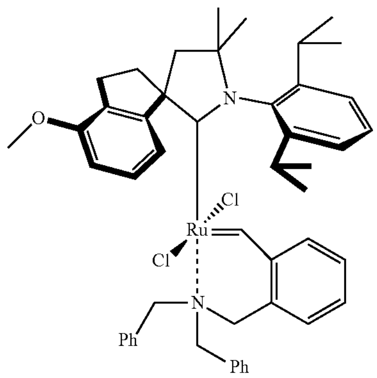
4f
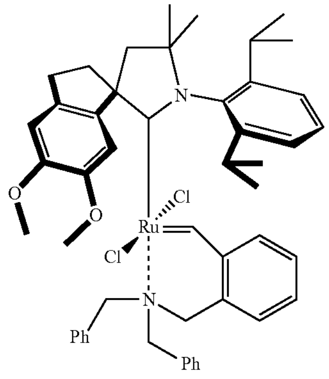
-continued
4g
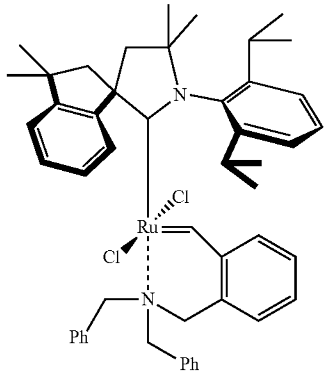
4h
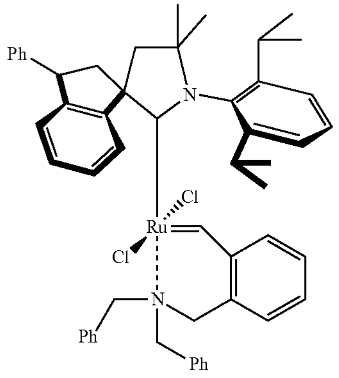
4i
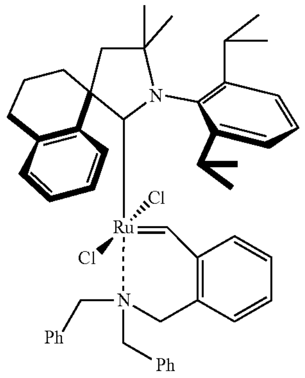
4j
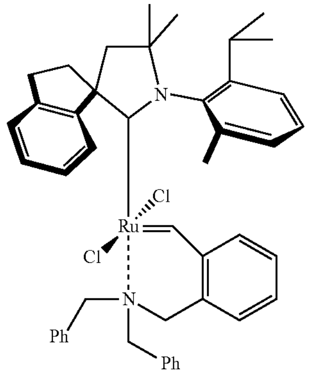

-continued
4aa
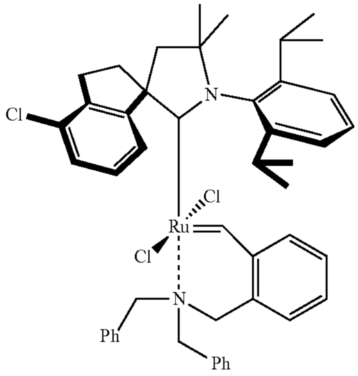
4k
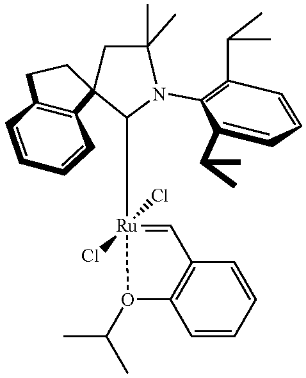
4l
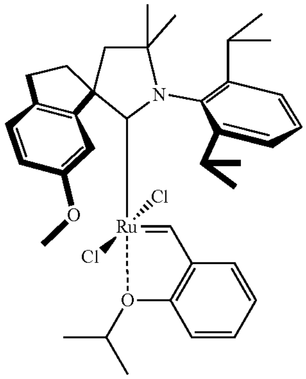
4m
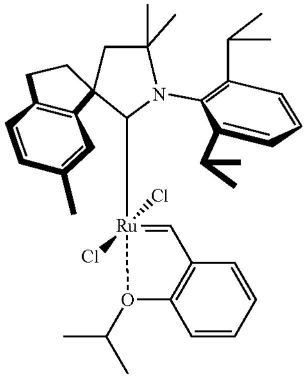
-continued
4n
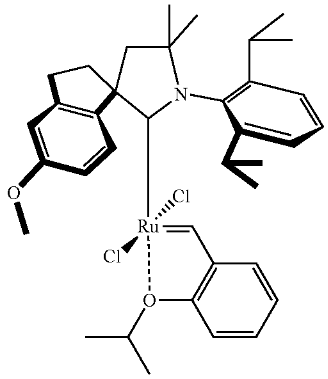
4o
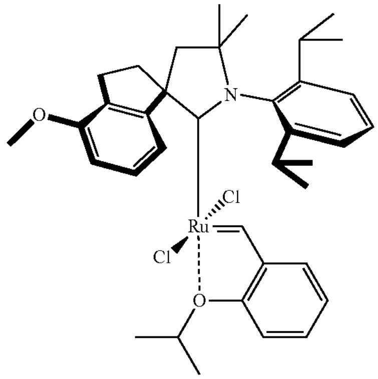
4p
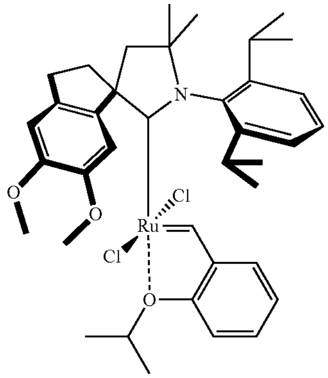
4q
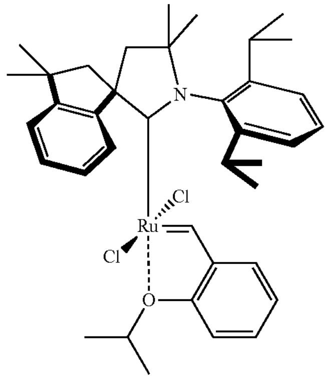

-continued
4r
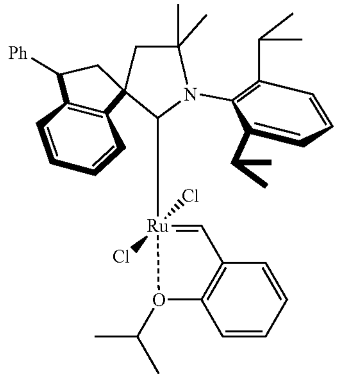
4s
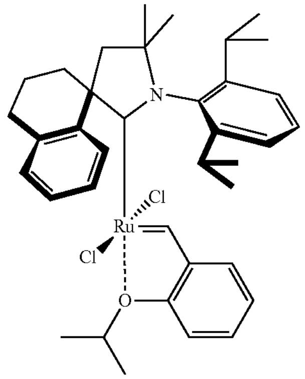
4t
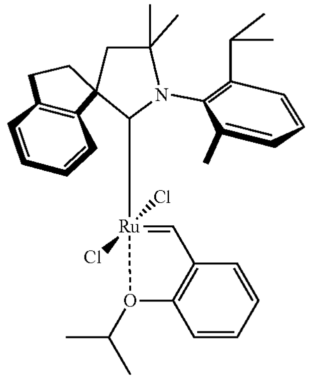
4ab
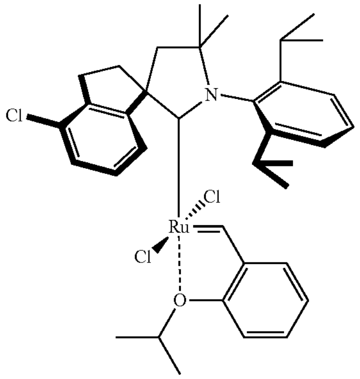
-continued
4u
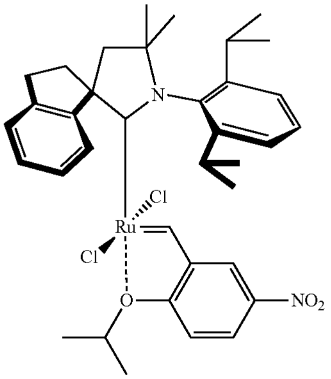
4v
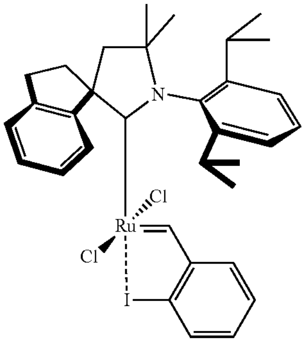
4w
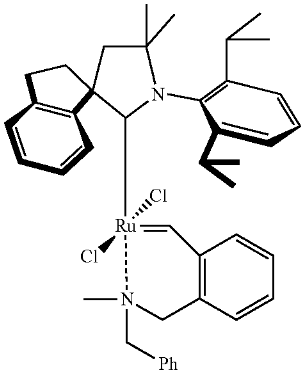
4x
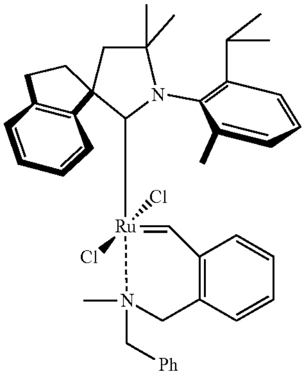

-continued

4ac

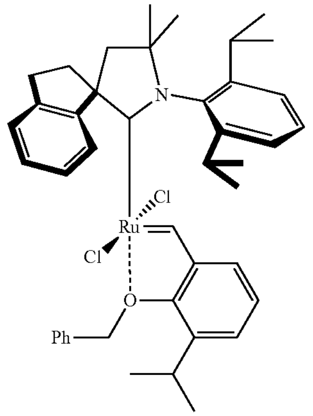

4y

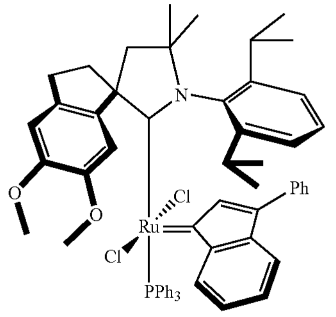

4z

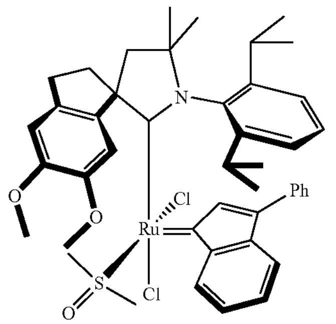

4ad

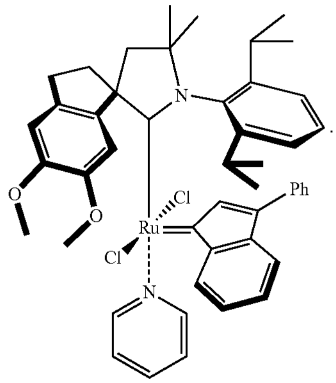

6. A method for preparing the compound of general formula 4,

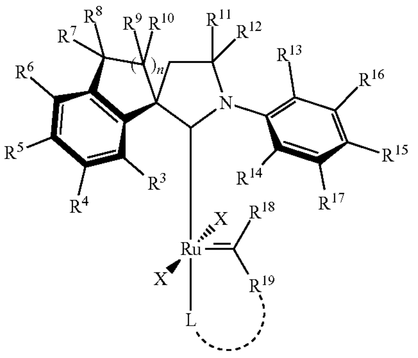

4 wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other denote an entity selected from the group comprising hydrogen atom, alkyl group $C_1$-$C_6$, cycloalkyl group $C_3$-$C_7$, alkoxy group $C_1$-$C_6$, aryl group $C_6$-$C_{20}$, heteroaryl group $C_4$-$C_{20}$, and halogen atom; wherein the entity is optionally substituted with one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, $R^{18}$ denotes hydrogen atom, $R^{19}$ denotes an entity selected from the group comprising aryl group $C_6$-$C_{20}$, heteroaryl group $C_4$-$C_{20}$, aralkyl group $C_7$-$C_{24}$, and alkenyl group $C_2$-$C_6$, wherein the entity is optionally substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —$CH_2$R', —$CH_2$NR'R", —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', in which R' and R" independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, in which R' and R" are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'"), amide group (—CONR'"R""), formyl group (—CHO), ketone group (—COR'"), and hydroxamic group (—CON(OR'")(R"")), wherein R'" and R"" independently are selected from the group comprising alkyl $C_1$-$C_{12}$, cycloalkyl $C_3$-$C_{12}$, aryl $C_6$-$C_{20}$, and heteroaryl $C_4$-$C_{20}$, wherein R' and R" or R'" and R"" are optionally linked to each other, or $R^{18}$ and $R^{19}$ are optionally linked to each other thereby forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$, and heteroaryloxy group $C_4$-$C_{24}$, L denotes a neutral ligand, connected with the ruthenium atom via a coordination bond from the heteroatom that forms a part of a compound selected from the group comprising —NR'$_3$, —PR'$_3$, —OR'$_2$, —SR'$_2$, —S(O)R'$_2$, halogen atom, and optionally substituted pyridine ($C_5H_4NR'$), in which R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), in which R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, X denotes halogen atom, and n is 1 or 2, wherein L and $R^{19}$ are optionally linked to each other, comprising:

(1) reacting a salt of general formula 9

9

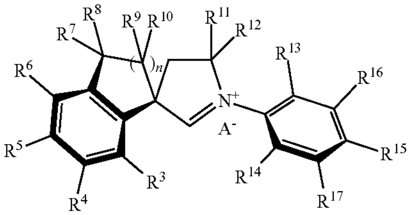

wherein $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$ independently of each other are an entity selected from the group comprising hydrogen atom, alkyl group $C_1$-$C_6$, cycloalkyl $C_3$-$C_7$, alkoxy group $C_1$-$C_6$, aryl group $C_6$-$C_{20}$, heteroaryl $C_4$-$C_{20}$, and halogen atom; wherein the entity is optionally substituted with at one or more moieties selected from the group comprising alkyl group $C_1$-$C_6$, cycloalkyl group $C_3$-$C_7$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, and halogen atom, A-denotes an anion selected from the group comprising halogen anion, $BF_4^-$, $PF_6^-$, $ClO_4^-$, $CF_3SO_2O^-$, and $HCl_2^-$ with a base selected from group comprising potassium bis(trimethylsilyl)amide, lithium bis(trimethylsilyl) amide, sodium bis(trimethylsilyl)amide, and lithium diisopropylamide;

(2) subsequently contacting the reaction product of (1) with a complex of general formula 1

1

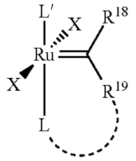

wherein $R^{18}$ denotes hydrogen atom, $R^{19}$ denotes a compound selected from the group comprising aryl group $C_6$-$C_{20}$, heteroaryl group $C_4$-$C_{20}$, aralkyl group $C_7$-$C_{24}$, and alkenyl group $C_2$-$C_6$ wherein $R^{19}$ optionally is substituted with one or more moieties selected from the group comprising alkyl group $C_1$-$C_6$, aryl group $C_6$-$C_{20}$, heteroaryl group $C_4$-$C_{20}$, aryloxy group $C_6$-$C_{24}$, heteroaryloxy group $C_4$-$C_{24}$, halogen atom, —OR', —CH$_2$R', —CH$_2$NR'R'', —SR', —S(O)R', —SO$_2$R', —SO$_2$NH$_2$, —SO$_2$NHR', —SO$_2$NR'R'', —NR'R'', —NO$_2$, —CN, —COOH, —COOR', —CONR'R'', —NR'C(O)R'', —NHC(O)R', —NR'C(O)OR'', —NHC(O)OR'', —CHO, and —COR', wherein R' and R'' independently are selected from the group comprising alkyl $C_1$-$C_6$, cycloalkyl $C_3$-$C_7$, aryl $C_6$-$C_{24}$, heteroaryl $C_4$-$C_{20}$, and aralkyl $C_7$-$C_{24}$, wherein R' and R'' are optionally substituted with one or more moieties selected from the group comprising alkyl $C_1$-$C_{12}$, alkoxy $C_1$-$C_{12}$, aryloxy $C_6$-$C_{24}$, heteroaryloxy $C_4$-$C_{24}$, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R'' or R''' and R'''' are optionally linked to each other, or $R^{18}$ and $R^{19}$ are optionally linked to each other, forming an aromatic polycyclic system, which may be substituted with one or more substituents selected from group comprising alkyl group $C_1$-$C_{25}$, cycloalkyl group $C_3$-$C_7$, aryl group $C_6$-$C_{24}$, heteroaryl group $C_4$-$C_{20}$, alkenyl group $C_2$-$C_{25}$, cycloalkenyl group $C_3$-$C_{25}$, alkoxy group $C_1$-$C_{25}$, aryloxy group $C_6$-$C_{24}$ and heteroaryloxy group $C_4$-$C_{24}$, L denotes a neutral ligand, connected with the ruthenium atom via coordination bond from the heteroatom that forms a part of a compound selected from the group comprising —NR'$_3$, —PR'$_3$, —OR'$_2$, —SR'$_2$, —S(O)R'$_2$, halogen atom, and optionally substituted pyridine ($C_5H_4NR'$), wherein R' independently is selected from the group comprising hydrogen atom, alkyl $C_1$-$C_{12}$, cycloalkyl $C_3$-$C_{12}$, aryl $C_6$-$C_{20}$, heteroaryl $C_4$-$C_{20}$, alkoxy $C_1$-$C_{12}$, aryloxy $C_6$-$C_{24}$, heteroaryloxy $C_4$-$C_{24}$, and halogen atom, wherein R' can be optionally substituted with one or more moieties selected from the group comprising alkyl group $C_1$-$C_6$, cycloalkyl group $C_3$-$C_{12}$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, aralkyl group $C_7$-$C_{24}$, halogen atom, ester group (—COOR'''), amide group (—CONR'''R''''), formyl group (—CHO), ketone group (—COR'''), and hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R''' and R'''' are optionally linked to each other, L' denotes the neutral ligand $P(R')_3$, wherein each substituent R' independently is selected from the group comprising alkyl group $C_1$-$C_{12}$, cycloalkyl group $C_3$-$C_{12}$, aryl group $C_6$-$C_{20}$, heteroaryl group $C_4$-$C_{20}$, alkoxy group $C_1$-$C_{25}$, aryloxy group $C_6$-$C_{24}$, and heteroaryloxy group $C_4$-$C_{24}$, wherein two substituents R' may be linked to each other thereby forming a heterocycloalkyl ring comprising a phosphorous atom as a ring atom, X denotes halogen atom, wherein L and $R^{19}$ are optionally linked to each other;

(3) optionally adding a compound of general formula 10

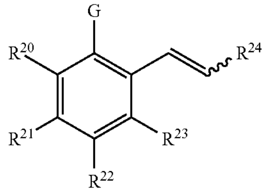

10 wherein $R^{20}$, $R^{21}$, $R^{22}$, $R^{23}$, $R^{24}$ independently are selected from the group comprising hydrogen atom, alkyl group $C_1$-$C_6$, aryl group $C_6$-$C_{20}$, heteroaryl group $C_4$-$C_{20}$, alkoxy group $C_1$-$C_6$, aryloxy group $C_6$-$C_{24}$, heteroaryloxy group $C_4$-$C_{24}$, halogen atom, —$CH_2$R', —SR', —S(O)R', —$SO_2$R', —$SO_2NH_2$, —$SO_2$NHR', —$SO_2$NR'R", —NR'R", —$NO_2$, —CN, —COOH, —COOR', —CONR'R", —NR'C(O)R", —NHC(O)R', —NR'C(O)OR", —NHC(O)OR", —CHO, and —COR', wherein R' and R" independently denote alkyl $C_1$-$C_5$, aryl $C_6$-$C_{24}$, wherein R' and R" are optionally linked to each other, $R^{24}$ denotes hydrogen atom or alkyl group $C_1$-$C_6$, G denotes halogen atom or substituent selected from group —OR', —SR', —NR'R", —$CH_2$NR'R" wherein R' and R" independently denote alkyl group $C_1$-$C_{25}$, cycloalkyl group $C_3$-$C_{12}$, alkoxy group $C_1$-$C_{25}$, aralkyl group $C_7$-$C_{24}$, aryl group $C_6$-$C_{20}$, heteroaryl group $C_4$-$C_{20}$, aryloxy group $C_6$-$C_{24}$, heteroaryloxy group $C_4$-$C_{24}$, which are optionally substituted with at least one alkyl $C_1$-$C_{12}$, alkoxy $C_1$-$C_{12}$, aryloxy $C_6$-$C_{24}$, heteroaryloxy $C_4$-$C_{24}$, halogen atom, ester group (—COOR'''), amide group (—CONR'''R''''), formyl group (—CHO), ketone group (—COR'''), hydroxamic group (—CON(OR''')(R'''')), wherein R''' and R'''' independently denote alkyl $C_1$-$C_{12}$, cycloalkyl $C_3$-$C_{12}$, aryl $C_6$-$C_{20}$, heteroaryl $C_4$-$C_{20}$, wherein R' and R" or R''' and R'''' are optionally linked to each other; and (4) optionally adding a copper (1) chloride or $ArSO_2Cl$, wherein Ar denotes aryl group $C_6$-$C_{20}$.

7. A method of olefin cross metathesis comprising reacting an olefin with a compound of claim 1 as (pre)catalyst and/or catalyst.

8. The method according to claim 7, wherein the olefin cross metathesis produces at least one compound comprising a terminal double bond C═C as a main product.

9. The method according to claim 7, wherein the olefin contacted during the cross metathesis reaction is ethylene.

10. The method according to claim 7, wherein the compound of claim 1 is used in amount not exceeding 1 ppm.

11. The method according to claim 10, wherein the compound of claim 1 is used in amount from 0.1 to 1 ppm.

12. The method according to claim 7, wherein the cross metathesis reaction is carried out without solvent or is carried out in the presence of an organic solvent selected from group comprising toluene, benzene, mesitylene, dichloromethane, dichloroethane, ethyl acetate, methyl acetate, tert-butyl-methyl ether, cyclopentyl-methyl ether, tetrahydrofuran, 2-methyltetrahydrofuran, dimethyl carbonate, cyclohexane, and mixtures thereof.

13. The method according to claim 7, wherein the cross metathesis reaction is carried out at a temperature within the range of from about 20 to about 150° C., and at a pressure within the range of from about 1 to about 50 bar.

* * * * *